United States Patent
Liu et al.

(10) Patent No.: US 9,637,454 B2
(45) Date of Patent: May 2, 2017

(54) FLUORINE SUBSTITUTED CYCLIC AMINE COMPOUNDS AND PREPARATION METHODS, PHARMACEUTICAL COMPOSITIONS, AND USES THEREOF

(71) Applicant: SHANGHAI INSTITUTE OF MATERIA MEDICA, CHINESE ACADEMY OF SCIENCES, Pudong, Shanghai (CN)

(72) Inventors: Hong Liu, Shanghai (CN); Haiyan Zhang, Shanghai (CN); Yu Zhou, Shanghai (CN); Yan Fu, Shanghai (CN); Hualiang Jiang, Shanghai (CN); Xican Tang, Shanghai (CN); Kaixian Chen, Shanghai (CN)

(73) Assignee: SHANGHAI INSTITUTE OF MATERIA MADICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 14/438,457

(22) PCT Filed: Oct. 17, 2013

(86) PCT No.: PCT/CN2013/085356
§ 371 (c)(1),
(2) Date: Apr. 24, 2015

(87) PCT Pub. No.: WO2014/063587
PCT Pub. Date: May 1, 2014

(65) Prior Publication Data
US 2015/0284331 A1 Oct. 8, 2015

(30) Foreign Application Priority Data
Oct. 26, 2012 (CN) .......................... 2012 1 0418613

(51) Int. Cl.
| | | |
|---|---|---|
| *C07D 211/32* | (2006.01) | |
| *C07D 405/06* | (2006.01) | |
| *C07D 451/04* | (2006.01) | |
| *C07D 211/38* | (2006.01) | |
| *A61K 45/06* | (2006.01) | |
| *C07D 211/34* | (2006.01) | |
| *C07D 471/08* | (2006.01) | |
| *C07D 491/107* | (2006.01) | |

(52) U.S. Cl.
CPC ............ *C07D 211/32* (2013.01); *A61K 45/06* (2013.01); *C07D 211/34* (2013.01); *C07D 211/38* (2013.01); *C07D 405/06* (2013.01); *C07D 451/04* (2013.01); *C07D 471/08* (2013.01); *C07D 491/107* (2013.01)

(58) Field of Classification Search
CPC ... C07D 211/32; C07D 211/34; C07D 211/38; C07D 405/06; C07D 451/04; C07D 471/08; C07D 491/107; A61K 31/454; A61K 45/06

USPC ............... 514/319, 309, 317, 321, 330, 331; 546/206, 124, 197, 227, 235, 237
See application file for complete search history.

(56) References Cited

U.S. PATENT DOCUMENTS

| | | | |
|---|---|---|---|
| 9,249,098 B2 * | 2/2016 | Cheng | .................. C07D 211/32 546/206 |
| 2005/0107432 A1 * | 5/2005 | Iimura | .................. A61K 31/445 514/323 |
| 2009/0069304 A1 | 3/2009 | Hayashi et al. | |
| 2012/0252842 A1 | 10/2012 | Bhat et al. | |

FOREIGN PATENT DOCUMENTS

| | | |
|---|---|---|
| CN | 1030752 A | 2/1989 |
| EP | 0296560 A2 | 12/1988 |
| EP | 1157989 A1 | 11/2001 |
| EP | 1209151 A1 | 5/2002 |
| JP | S6479151 A | 3/1989 |
| JP | H 09268176 A | 10/1997 |
| JP | 2000319258 A | 11/2000 |
| JP | 2001139547 A | 5/2001 |
| RU | 2009128 C1 | 3/1994 |
| RU | 2009126589 A | 1/2011 |

(Continued)

OTHER PUBLICATIONS

Dorward "Side reactions . . . " p. ix (2005).*
Kryger et al. "Structure of acetylcholine . . . " Structure v.7(3) p. 297-307 (1999).*
Lee et al. "Synthesis and biological . . . " Nuclear Md. Biol. v.27 pp. 741-744 (2000).*
Man et al. "fluoro-substituted . . . " Bioorg. Med. Chem. Lett., v.13, p. 3415-17 (2003).*
Patani et al. "Bioisosterism . . . " Chem Rev. v.96, pp. 3147-3176 (1996).*
Rampa et al. "Acetylcholinesterase . . . " J. Med. Chem. 44, pp. 3810-3820 (2001).*
Sugimoto et al. "Synthesis and structure . . . " J. Med. Chem. 38 pp. 4821-4829 (1995).*

(Continued)

*Primary Examiner* — Celia Chang
(74) *Attorney, Agent, or Firm* — Panitch Schwarze Belisario & Nadel LLP

(57) ABSTRACT

The present invention relates to the field of pharmaceutical chemistry and pharmacotherapeutics, and in particular to compounds of general formula I, racemates, R-isomers, S-isomers, and pharmaceutically acceptable salts thereof and their mixtures, and the preparation methods thereof and a pharmaceutical composition containing the compounds and uses thereof as an acetylcholine esterase inhibitor.

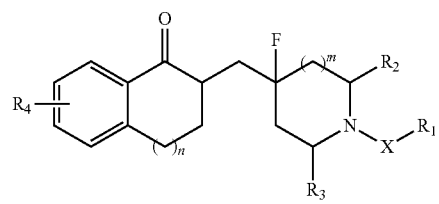

19 Claims, No Drawings

(56) References Cited

FOREIGN PATENT DOCUMENTS

| | | | |
|---|---|---|---|
| RU | 2478619 | C2 | 4/2013 |
| WO | 2007102392 | A1 | 9/2007 |
| WO | 2014008629 | * | 1/2014 |
| WO | 2014008629 | A1 | 1/2014 |
| WO | WO2014008629 | * | 1/2014 |

OTHER PUBLICATIONS

Improper Markush, Fed. Reg. v76(7) p. 7162-7175, slides 1, 64-67 (2011).*
Int'l Search Report issued on Jan. 23, 2014 in Int'l Application No. PCTCN2013/085356.
Extended Search Report issued Feb. 25, 2016 in EP Application No. 13849440.6.
Office Action issued on Apr. 8, 2016 in KR Application No. 10-2015-7008760.
Office Action issued Oct. 26, 2012 in RU Application No. 201210418613.8.
Office Action issued on Jun. 16, 2015 in JP Application No. 2015-538269.
Search report issued Oct. 26, 2012 in CN Application No. 2012-104186138.

* cited by examiner

FLUORINE SUBSTITUTED CYCLIC AMINE COMPOUNDS AND PREPARATION METHODS, PHARMACEUTICAL COMPOSITIONS, AND USES THEREOF

CROSS-REFERENCE TO RELATED APPLICATIONS

This application is a Section 371 of International Application No. PCT/CN2013/085356, filed Oct. 17, 2013, which was published in the Chinese language on May 1, 2014, under International Publication No. WO 2014/063587 A1 and the disclosure of which is incorporated herein by reference.

BACKGROUND OF THE INVENTION

Technical Field

The present invention relates to the field of medicinal chemistry and pharmacotherapeutics, in particular to a class of fluorosubstituted cyclic amine compounds, preparation thereof, pharmaceutical compositions containing such compounds, and uses thereof as acetylcholinesterase inhibitor, particularly for preparing medicaments for the treatment of Alzheimer's disease, Parkinson's disease, epilepsy or schizophrenia.

Background Art

With the rapid aging of society, the health status of the aged has received an increasing attention. Among numerous diseases that threaten the health of the aged, Alzheimer's disease (AD), also known as senile dementia, is the most common cause of dementia in the aged. AD is a progressive fatal neurodegenerative disease, the clinical manifestations of which are worsening of cognitive and memory functions, progressive decline of activities of daily life and a variety of neuropsychiatric symptoms and behavioral disorders. Incidence of AD in the aged is very high: nearly 50% of people affected by dementia suffer from Alzheimer's disease. When the patients are older than 85, the proportion will increase to 70%. Among the cause of death in the aged, AD ranks $4^{th}$, and lower than cardiovascular, cancer and cerebral apoplexy. Therefore, the study on the medicaments for treating AD has become one of the hotspots of new drug developments.

Reports from IMS Health (ims health) showed that, among the top 500 best-selling drugs in the world's seven major pharmaceutical markets, anti-senile dementia drug market has reached $ 6.41 billion in 2007 which is increased by 24.18% compared with the previous year. In 2008, anti-senile dementia drug market achieved an increase of 12.49% compared with the previous year and the market size reached $7.211 billion. The average annual growth rate of the last three years was about 23% and much higher than the average annual growth of global pharmaceutical market which is 5%-6%. "World Alzheimer Report 2010" showed that the total cost for the treatment of dementia reached $604 billion.

Thus, the anti-senile dementia drug market has great potential. However, "World Alzheimer Report 2011" published in 2012 showed that about 36 million people suffered from dementia, in which as many as three-quarters of patients were undiagnosed and unable to obtain the relevant treatment and care. In high-income countries, only 20-50% of dementia cases obtained primary care while only 10% in low and middle income countries.

At present, the medicaments for the treatment of senile dementia are as follows: (1) cholinesterase inhibitors: such as tacrine, donepezil, Huperzine A, galantamine, etc., a major cause of Alzheimer's Disease is the lack of choline thereby resulting in patients hypomnesia, disorientation, behavioral and personality changes, and so on. Therefore, the medicaments enhancing cholinergic effect play an important role in the treatment of senile dementia. (2) calcium antagonists: such as nimodipine, flunarizine hydrochloride and so on. (3) brain metabolism regulators: such as Nicergoline, Almitrine, piracetam and so on. (4) neuroprotective agents: such as cerebrolysin. Among the clinical medicaments for the treatment of senile dementia, acetylcholinesterase inhibitors (AchEI) with the accurate efficacy are widely used in clinical treatment.

Cholinesterase is a key enzyme in the biological nerve conduction. According to the specificity to catalyzed substrates, cholinesterase is divided into acetylcholinesterase (AChE) and butyrylcholinesterase. Acetylcholinesterase can catalyze the decomposition reaction of acetylcholine, thereby resulting in lack of acetylcholine and the failure of neural signal conduction and further leading to the decline of patients' cognitive function and loss of memory, and clinical manifestations are senile dementia symptoms. Acetylcholinesterase inhibitors can inhibit AChE activity, slow down the rate of hydrolysis of acetylcholine, improve the level of acetylcholine in the synaptic cleft and ensure the normal conduction of neural signals thereby playing a therapeutic effect on senile dementia.

Donepezil hydrochloride (E2020) disclosed in EP0296560A2 is the second generation acetylcholinesterase inhibitor, the treatment effect of which is reversible inhibition of acetylcholine hydrolysis caused by acetylcholinesterase (AChE) thereby increasing the acetylcholine content in receptor site. E2020, which was the second medicament approved by US FDA for the treatment of mild and moderate senile dementia, was developed by Eisai and Pfizer Limited and come into the market in 1997 in United States. E2020, which has been approved for marketing by more than 50 countries and regions including China, is a relatively safe and effective drug for the treatment of senile dementia and the preferred drug for treating mild and moderate senile dementia. The selective affinity of donepezil hydrochloride for acetylcholinesterase is 1250 times stronger than that for butyrylcholinesterase. Donepezil hydrochloride can obviously inhibit the cholinesterase in brain while butyrylcholinesterase mainly exists outside of the central nervous system. So E2020 has no effect on peripheral heart (myocardium) or the small intestine (smooth muscle) and has few side effects. Compared with tacrine, E2020 has better effects, higher selectivity and less toxicity for central nervous system. Therefore, E2020 has become first-line medicament for treating senile dementia in clinical and the global sales in 2010 reached $3.4 billion.

However, there is still a large gap between the overall development speed of anti-AD medicament studies and the market demand, and there are few of medicaments with confirmative efficacy. Medicaments on the market can not meet the needs of the patients. Therefore, more acetylcholinesterase inhibitors are needed to meet the market demand.

BRIEF SUMMARY OF THE INVENTION

Summary of the Invention

One object of the invention is to provide a fluoro-substituted cyclic amine compound as shown in general formula I, a pharmaceutically acceptable salt, a racemate, a R-isomer, a S-isomer thereof or a mixture thereof.

Another object of the invention is to provide a preparation method for the above fluoro-substituted cyclic amine compound as shown in general formula I.

Another object of the invention is to provide a pharmaceutical composition including therapeutically effective amount of one or more selected from the above fluoro-substituted cyclic amine compounds as shown in general formula I, pharmaceutically acceptable salts, racemates, R-isomers, S-isomers thereof or mixtures thereof.

Another object of the invention is to provide an acetylcholinesterase inhibitor including one or more selected from the above fluoro-substituted cyclic amine compounds as shown in general formula I, pharmaceutically acceptable salts, racemates, R-isomers, S-isomers thereof or mixtures thereof.

Another object of the invention is to provide a use of the above fluoro-substituted cyclic amine compounds as shown in general formula I, pharmaceutically acceptable salts, racemates, R-isomers, S-isomers thereof or mixtures thereof for preparing the medicaments for treating acetylcholinesterase-related nerve system diseases, such as Alzheimer's disease, Parkinson's disease, epilepsy, schizophrenia, and so on.

Another object of the invention is to provide a method for treating acetylcholinesterase-related nerve system diseases, such as Alzheimer's disease, Parkinson's disease, epilepsy, schizophrenia, etc. comprising administrating one or more selected from the above fluoro-substituted cyclic amine compounds as shown in general formula I, pharmaceutically acceptable salts, racemates, R-isomers, S-isomers thereof or mixtures thereof to a patient in need thereof.

DETAILED DESCRIPTION OF THE INVENTION

Based on above objects, the present invention provides a fluoro-substituted cyclic amine compound as shown in general formula I, a racemate, a R-isomer, a S-isomer and a pharmaceutically acceptable salt thereof or a mixture thereof:

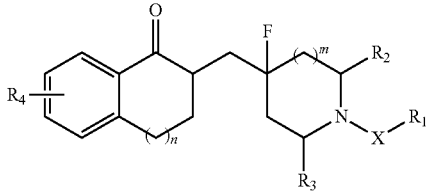

general formula I wherein,
m is an interger of 0-3; wherein m preferably is 0, 1 or 2.
n is an interger of 0-3; wherein n preferably is 0, 1 or 2.
X is (CH2)p, CO or SO2, wherein p is an interger of 0-3; X preferably is (CH2)p or CO, p preferably is 1 or 2.
$R_1$ is a substituted or unsubstituted $C_3$-$C_{10}$ cycloalkyl, a substituted or unsubstituted $C_3$-$C_{10}$ cycloalkenyl, a substituted or unsubstituted 3-12 membered heterocyclic group, a substituted or unsubstituted $C_6$-$C_{12}$ aryl; the substituent(s) of $R_1$ is 1, 2, 3, 4 or 5 same or different substituents independently selected from the group consisting of a halogen, a $C_1$-$C_6$ alkyl, a halogen substituted $C_1$-$C_6$ alkyl, a $C_1$-$C_6$ alkoxy, a $C_1$-$C_6$ alkoxycarbonyl, a halogen substituted $C_1$-$C_6$ alkoxy, a $C_2$-$C_6$ alkenyl, a $C_2$-$C_6$ alkynyl, a $C_3$-$C_8$ cycloalkyl, a cyano, a nitro, an amino, a hydroxyl, a hydroxymethyl, a carboxyl, a mercapto, a sulfonyl, a $C_6$-$C_{10}$ aryl and a 3-12 membered heterocyclic radical; or, two adjacent substituents of the $C_6$-$C_{12}$ aryl and carbon atom(s) of adjacent aromatic ring together form a $C_3$-$C_7$ cycloalkyl, a $C_3$-$C_7$ cycloalkenyl or a 3-7 membered heterocyclic radical; and each heterocyclic radical independently contains 1-4 heteroatoms selected from O, S or N;

preferably, $R_1$ is a substituted or unsubstituted $C^3$-$C^8$ cycloalkyl, or a substituted or unsubstituted $C_6$-$C_{12}$ aryl; the substituent(s) of $R_1$ is 1-5 same or different substituents independently selected from the group consisting of a halogen, a $C_1$-$C_6$ alkyl, a halogen substituted $C_1$-$C_6$ alkyl, a $C_1$-$C_6$ alkoxy, a $C_1$-$C_6$ alkoxycarbonyl, a halogen substituted $C_1$-$C_6$ alkoxy, a $C_2$-$C_6$ alkenyl, a $C_2$-$C_6$ alkynyl, a $C_3$-$C_8$ cycloalkyl, a cyano, a nitro, an amino, a hydroxyl, a hydroxymethyl, a carboxyl, a mercapto, a sulfonyl, a phenyl, a naphthyl and 3-12 membered heterocyclic radical; or two adjacent substituents of the $C_6$-$C_{12}$ aryl and carbon atom(s) of adjacent aromatic ring together form a $C_3$-$C_7$ cycloalkyl, a $C_3$-$C_7$ cycloalkenyl or a 3-7 membered heterocyclic radical; and the heterocyclic radical contains 1-3 heteroatoms selected from O, S or N;

more preferably, $R_1$ is a $C_3$-$C_8$ cycloalkyl, a substituted or unsubstituted phenyl or a substituted or unsubstituted naphthyl; the substituent(s) of $R_1$ is 1-5 same or different substituents independently selected from the group consisting of a halogen, a $C_1$-$C_6$ alkyl, a $C_1$-$C_6$ alkoxy, a halogen substituted $C_1$-$C_6$ alkoxy, a $C_1$-$C_6$ alkoxycarbonyl, a $C_2$-$C_6$ alkenyl, a $C_2$-$C_6$ alkynyl, a cyano, a nitro, an amino, a hydroxyl, a hydroxymethyl, a trifluoromethyl, a trifluoromethoxy, a carboxyl, a mercapto, a sulfonyl and a phenyl, or two adjacent substituents of the phenyl and carbon atoms of adjacent benzene ring together form

most preferably, $R_1$ is a cyclobutyl, a cyclopentyl, a cyclohexyl, a cycloheptyl or a substituted or unsubstituted phenyl, the substituent(s) of the substituented phenyl is 1-5 same or different substituents independently selected from a group consisting of a halogen, a nitro, a cyano, a trifluoromethyl, a trifluoroethyl, a trifluoropropyl, a trifluoromethoxy, a methyl, an ethyl, a propyl, an isopropyl, a butyl, a tert-butyl, a 2-methylpropyl, a phenyl, a methoxycarbonyl, an ethoxycarbonyl and a propoxycarbonyl, or two adjacent substituents of the phenyl and carbon atoms of adjacent benzene ring together form

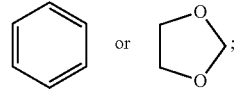

each of $R_2$ and $R_3$ is independently selected from a group consisting of a hydrogen, a carboxyl, a $C_1$-$C_4$ alkoxycarbonyl and a $C_1$-$C_4$ alkyl; or $R_2$ and $R_3$ together form a $C_1$-$C_4$ alkylidene;

preferably, each of $R_2$ and $R_3$ is independently selected from a group consisting of a hydrogen, a carboxyl, a methoxycarbonyl, an ethoxycarbonyl, a propoxycarbonyl, a methyl, an ethyl, a propyl, an isopropyl, a butyl and a 2-methylpropyl; or $R_2$ and $R_3$ together form a methylene, an ethylene or a propylene;

$R_4$ is 1-4 same or different substituents selected from a group consisting of a hydrogen, a halogen, a $C_1$-$C_6$ alkyl, a halogen substituted $C_1$-$C_6$ alkyl, a $C_1$-$C_6$ alkoxy, a halogen substituted $C_1$-$C_6$ alkoxy, a $C_2$-$C_6$ alkenyl, a $C_2$-$C_6$ alkynyl, a cyano, a nitro, an amino, a hydroxyl, a hydroxymethyl, a carboxyl, a mercapto, a sulfonyl, —O[($CH_2$)qO]r$R_5$, a phenyl and a 3-12 membered heterocyclic radical; wherein the heterocyclic radical contains 1-3 heteroatoms selected from O, S or N; $R_5$ is selected from a group consisting of a hydrogen, a halogen, a $C_1$-$C_6$ alkyl, a halogen substituted $C_1$-$C_6$ alkyl, a $C_2$-$C_6$ alkenyl, a $C_2$-$C_6$ alkynyl and a hydroxymethyl; q is 1, 2, 3 or 4; r is 1, 2, 3 or 4;

preferably, $R_4$ is 1-3 same or different substituents selected from a group consisting of a hydrogen, a halogen, a $C_1$-$C_6$ alkyl, a halogen substituted $C_1$-$C_6$ alkyl, a $C_1$-$C_6$ alkoxy, a halogen substituted $C_1$-$C_6$ alkoxy, a $C_2$-$C_6$ alkenyl, a $C_2$-$C_6$ alkynyl, a cyano, a nitro, an amino, a hydroxyl, a carboxyl and —O[($CH_2$)qO]r$R_5$; $R_5$ is selected from a group consisting of a hydrogen, a halogen, a $C_1$-$C_6$ alkyl and a halogen substituted $C_1$-$C_6$ alkyl; q is 1, 2 or 3; and r is 1, 2 or 3;

more preferably, $R_4$ is 1-2 same or different substituents selected from the group consisting of a hydrogen, a halogen, a $C_1$-$C_6$ alkyl, a $C_1$-$C_6$ alkoxy, a halogen substituted $C_1$-$C_6$ alkoxy, a hydroxyl and —O[($CH_2$)qO]r$R_5$; $R_5$ is selected from a $C_1$-$C_6$ alkyl or a halogen substituted $C_1$-$C_6$ alkyl; q is 1, 2 or 3; and r is 1, 2 or 3.

In the present invention, said halogen is F, Cl, Br or I.

The terms used in the present invention have general meanings as known by the skilled in the art, unless otherwise noted.

In the present invention, the term "$C_1$-$C_6$ alkyl" means a linear or branched alkyl having 1-6 carbon atoms, including but not limited to a methyl, an ethyl, a propyl, an isopropyl, a butyl, an isobutyl, a sec-butyl, a tert-butyl, a pentyl and a hexyl etc., preferably, an ethyl, a propyl, an isopropyl, a butyl, an isobutyl, a sec-butyl and a tert-butyl.

In the present invention, the term "$C_1$-$C_6$ alkoxy" means a linear or branched alkoxy having 1-6 carbon atoms, including but not limited to a methoxy, an ethoxy, a propoxy, an isopropoxy, a butoxy and the like.

In the present invention, the term "$C_2$-$C_6$ alkenyl" means a linear or branched alkenyl having 2-6 carbon atoms containing one double bond, including but not limited to an ethenyl, a propenyl, a butenyl, an isobutenyl, a pentenyl, a hexenyl and the like.

In the present invention, the term "$C_2$-$C_6$ alkynyl" means linear or branched alkynyl having 2-6 carbon atoms containing one triple bond, including but not limited to an ethynyl, a propynyl, a butyryl, an isobutylnyl, a pentynyl, a hexynyl and the like.

In the present invention, the term "$C_3$-$C_{10}$ cycloalkyl" means a cycloalkyl having 3-10 carbon atoms on the ring, including but not limited to a cyclopropyl, a cyclobutyl, a cyclopentyl, a cyclohexyl, a cycloheptyl, a cyclooctyl, a cyclodecyl and the like. The term "$C_3$-$C_8$ cycloalkyl", "$C_3$-$C_7$ cycloalkyl" and "$C_3$-$C_6$ cycloalkyl" have similar meanings.

In the present invention, the term "$C_3$-$C_{10}$ cycloalkenyl" means a cycloalkenyl having 3-10 carbon atoms on the ring, including but not limited to a cyclopropenyl, a cyclobutenyl, a cyclopentenyl, a cyclohexenyl, a cycloheptenyl, a cyclooctenyl and cyclodecenyl and the like. The term "$C_3$-$C_7$ cycloalkenyl" has similar meaning.

In the present invention, the term "$C_6$-$C_{12}$ aryl" means an aromatic cyclic group having 6-12 carbon atoms without heteroatom on the ring, such as a phenyl, a naphthyl and the like. The term "$C_6$-$C_{10}$ aryl" has similar meaning.

In the present invention, the term "3-12 membered heterocyclic radical" means saturated or unsaturated 3-12 membered cyclic group having 1-3 heteroatoms selected from O, S or N on the ring, such as dioxocyclopentyl and the like. The term "3-7 membered heterocyclic radical" has similar meaning.

In one preferred embodiment, above fluoro-substituted cyclic amine compounds as shown in general formula I are fluoro-substituted cyclic amine compounds as shown in general formula II:

general formula II

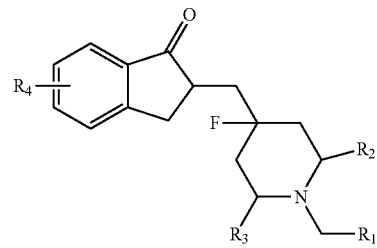

wherein, $R_1$ is

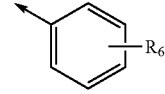

or a $C_3$-$C_{10}$ cycloalkyl, $R_6$ represents 1-5 substituents, and the substituent is independently selected from a group consisting of H, a halogen, a nitro, a cyano, a $C_1$-$C_6$ alkyl, a halogen substituted $C_1$-$C_6$ alkyl, a $C_1$-$C_6$ alkoxy, a halogen substituted $C_1$-$C_6$ alkoxy, a phenyl and a $C_1$-$C_6$ alkoxycarbonyl, or two adjacent $R_6$ and carbon atoms of adjacent benzene ring together form

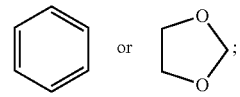

preferably, $R_1$ is

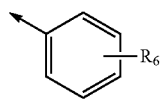

or a $C_3$-$C_7$ cycloalkyl, $R_6$ represents 1-5 substituents, and the substituent is independently selected from a group consisting of H, a halogen, a nitro, a cyano, a $C_1$-$C_4$ alkyl, a halogen substituted $C_1$-$C_4$ alkyl, a $C_1$-$C_4$ alkoxy, a halogen substituted $C_1$-$C_4$ alkoxy, a phenyl and a $C_1$-$C_4$ alkoxycarbonyl, or two adjacent $R_6$ and carbon atoms of adjacent benzene ring together form

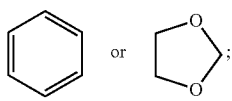 [SMILES: c1ccccc1 ; C1COCO1]

more preferably, $R_1$ is

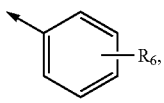

a cyclobutyl, a cyclopentyl, a cyclohexyl or a cycloheptyl, $R_6$ represents 1-5 substituents, and the substituent is independently selected from a group consisting of H, a halogen, a nitro, a cyano, —F, —Br, a trifluoromethyl, a trifluoroethyl, a trifluoropropyl, a methyl, an ethyl, a propyl, an isopropyl, a butyl, a 2-methylpropyl, a phenyl, a methoxycarbonyl, an ethoxycarbonyl and a propoxycarbonyl, or two adjacent $R_6$ and carbon atoms of adjacent benzene ring together form

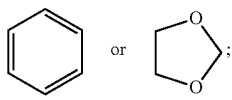 [SMILES: c1ccccc1 ; C1COCO1]

each of $R_2$ and $R_3$ is independently selected from a group consisting of a hydrogen, a carboxyl, a $C_1$-$C_4$ alkoxycarbonyl and a $C_1$-$C_4$ alkyl; or $R_2$ and $R_3$ together form a $C_1$-$C_4$ alkylidene;

preferably, each of $R_2$ and $R_3$ is independently selected from a group consisting of a hydrogen, a carboxyl, a methoxycarbonyl, an ethoxycarbonyl, a propoxycarbonyl, a methyl, an ethyl, a propyl, an isopropyl, a butyl and a 2-methylpropyl; or $R_2$ and $R_3$ together form a methylene, an ethylene or a propylene.

$R_4$ represents 1-4 substituents, and the substituent is independently selected from a group consisting of a hydrogen, a halogen, a $C_1$-$C_6$ alkyl, a halogen substituted $C_1$-$C_6$ alkyl, a $C_1$-$C_6$ alkoxy, a halogen substituted $C_1$-$C_6$ alkoxy, a $C_2$-$C_6$ alkenyl, a $C_2$-$C_6$ alkynyl, a cyano, a nitro, an amino, a hydroxy, an carboxyl and —O[($CH_2)_q$O]$_r$R$_5$; wherein $R_5$ is selected from a group consisting of a hydrogen, a halogen, a $C_1$-$C_6$ alkyl and a halogen substituted $C_1$-$C_6$ alkyl; q is 1, 2 or 3; and r is 1, 2 or 3;

preferably, $R_4$ represents 1-2 substituents, and the substituent is independently selected from a group consisting of a hydrogen, a halogen, a $C_1$-$C_6$ alkyl, a $C_1$-$C_6$ alkoxy, a halogen substituted $C_1$-$C_6$ alkoxy, a hydroxyl and —O[($CH_2)_q$O]$_r$R$_5$; wherein $R_5$ is selected from a $C_1$-$C_6$ alkyl or a halogen substituted $C_1$-$C_6$ alkyl; q is 1, 2 or 3; and r is 1, 2 or 3.

In more preferred embodiments of the present invention, the compounds as shown in general formula I in the present invention are the following specific compounds:

| No. | name | structure |
|---|---|---|
| DC1 | 2-((4-fluoro-1-(4-nitrobenzyl)piperidin-4-yl)methyl)-5,6-dimethoxy-2,3-dihydro-1H-inden-1-one | 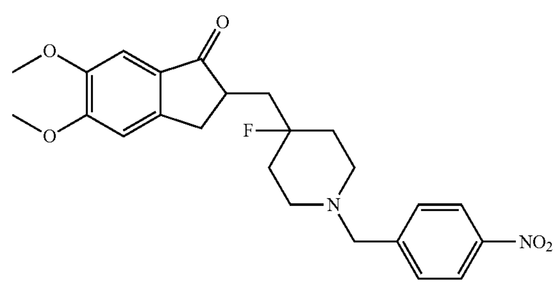 [SMILES: COc1cc2c(cc1OC)C(=O)C(CC1(F)CCN(Cc3ccc([N+](=O)[O-])cc3)CC1)C2] |
| DC3 | 2-((4-((5,6-dimethoxy-1-oxo-2,3-dihydro-1H-inden-2-yl)methyl)-4-fluoropiperidin-1-yl)methyl)benzonitrile | 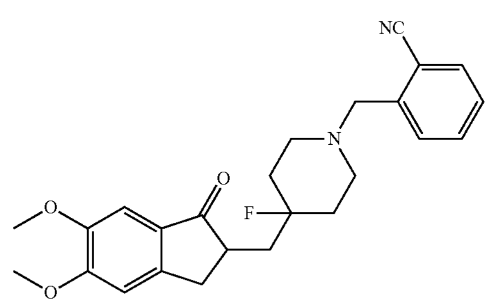 |

-continued

| No. | name | structure |
|---|---|---|
| DC4 | 2-((1-(3,5-dimethylbenzyl)-4-fluoropiperidin-4-yl)methyl)-5,6-dimethoxy-2,3-dihydro-1H-inden-1-one | 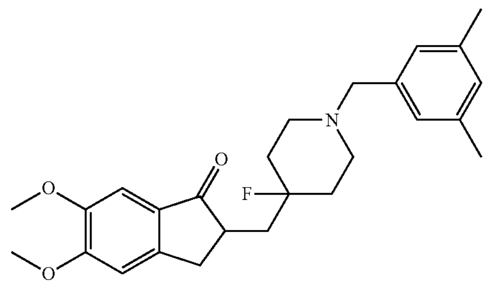 |
| DC5 | 2-((4-fluoro-1-(4-fluorobenzyl)piperidin-4-yl)methyl)-5,6-dimethoxy-2,3-dihydro-1H-inden-1-one | 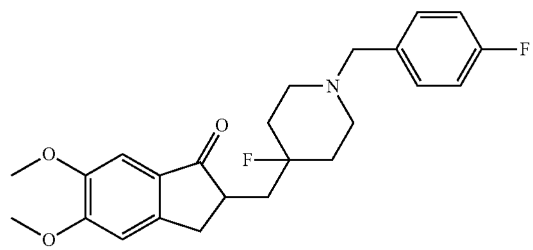 [SMILES: COc1cc2c(cc1OC)C(=O)C(CC1(F)CCN(Cc3ccc(F)cc3)CC1)C2] |
| DC6 | 2-((4-fluoro-1-(4-(trifluoromethoxy)benzyl)piperidin-4-yl)methyl)-5,6-dimethoxy-2,3-dihydro-1H-inden-1-one | 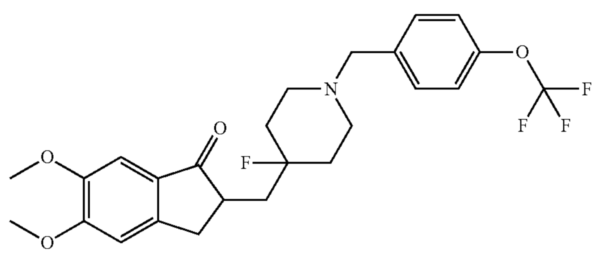 [SMILES: COc1cc2c(cc1OC)C(=O)C(CC1(F)CCN(Cc3ccc(OC(F)(F)F)cc3)CC1)C2] |
| DC7 | 2-((1-(4-(tert-butyl)benzyl)-4-fluoropiperidin-4-yl)methyl)-5,6-dimethoxy-2,3-dihydro-1H-inden-1-one | 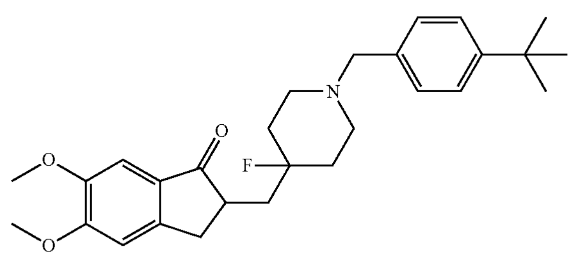 [SMILES: COc1cc2c(cc1OC)C(=O)C(CC1(F)CCN(Cc3ccc(C(C)(C)C)cc3)CC1)C2] |
| DC8 | 2-((4-fluoro-1-(2-fluoro-6-nitrobenzyl)piperidin-4-yl)methyl)-5,6-dimethoxy-2,3-dihydro-1H-inden-1-one | 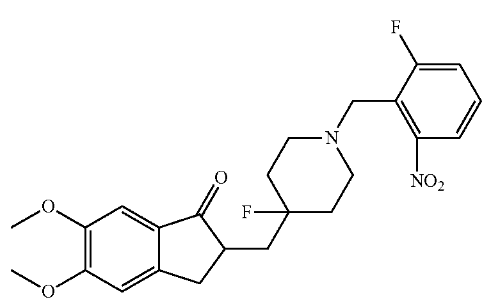 [SMILES: COc1cc2c(cc1OC)C(=O)C(CC1(F)CCN(Cc3c(F)cccc3[N+](=O)[O-])CC1)C2] |
| DC9 | 2-((1-((6-bromobenzo[d][1,3]dioxol-5-yl)methyl)-4-fluoropiperidin-4-yl)methyl)-5,6-dimethoxy-2,3-dihydro-1H-inden-1-one | 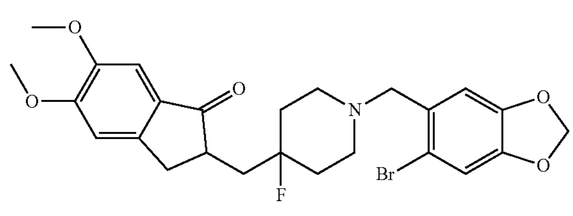 [SMILES: COc1cc2c(cc1OC)C(=O)C(CC1(F)CCN(Cc3cc4c(cc3Br)OCO4)CC1)C2] |

| No. | name | structure |
|---|---|---|
| DC10 | 2-((1-(2,4-difluorobenzyl)-4-fluoropiperidin-4-yl)methyl)-5,6-dimethoxy-2,3-dihydro-1H-inden-1-one | 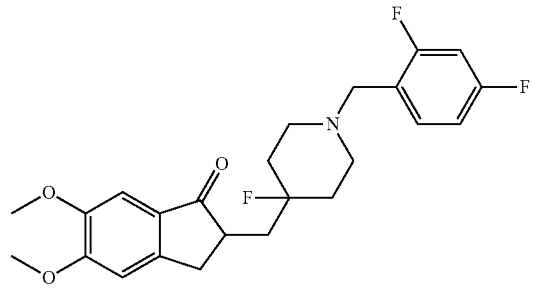 [SMILES: COc1cc2c(cc1OC)C(=O)C(CC1(F)CCN(Cc3ccc(F)cc3F)CC1)C2] |
| DC11 | 2-((1-(3-bromobenzyl)-4-fluoropiperidin-4-yl)methyl)-5,6-dimethoxy-2,3-dihydro-1H-inden-1-one | 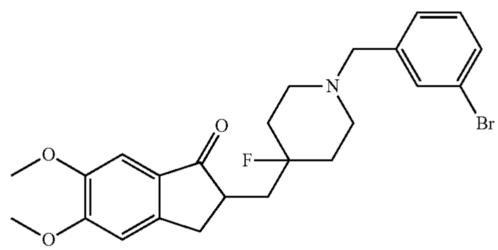 [SMILES: COc1cc2c(cc1OC)C(=O)C(CC1(F)CCN(Cc3cccc(Br)c3)CC1)C2] |
| DC12 | 2-((4-fluoro-1-(2,3,4-trifluorobenzyl)piperidin-4-yl)methyl)-5,6-dimethoxy-2,3-dihydro-1H-inden-1-one | 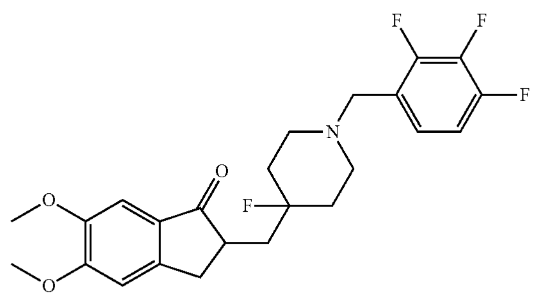 [SMILES: COc1cc2c(cc1OC)C(=O)C(CC1(F)CCN(Cc3ccc(F)c(F)c3F)CC1)C2] |
| DC13 | 3-((4-((5,6-dimethoxy-1-oxo-2,3-dihydro-1H-inden-2-yl)methyl)-4-fluoropiperidin-1-yl)methyl)benzonitrile | 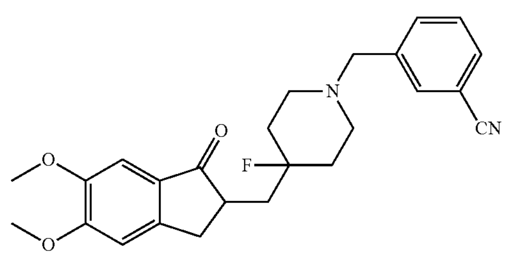 [SMILES: COc1cc2c(cc1OC)C(=O)C(CC1(F)CCN(Cc3cccc(C#N)c3)CC1)C2] |
| DC14 | 2-((1-(2-bromobenzyl)-4-fluoropiperidin-4-yl)methyl)-5,6-dimethoxy-2,3-dihydro-1H-inden-1-one | 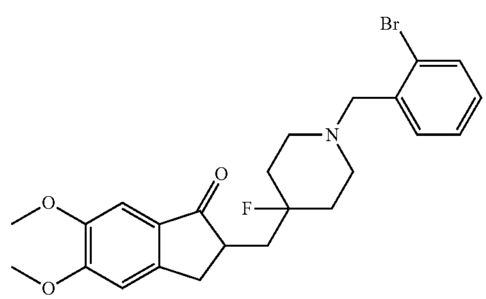 [SMILES: COc1cc2c(cc1OC)C(=O)C(CC1(F)CCN(Cc3ccccc3Br)CC1)C2] |

-continued

| No. | name | structure |
|---|---|---|
| DC15 | 2-((1-(4-bromo-2-fluorobenzyl)-4-fluoropiperidin-4-yl)methyl)-5,6-dimethoxy-2,3-dihydro-1H-inden-1-one | 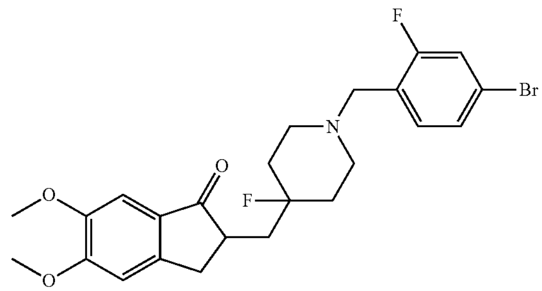 [SMILES: COc1cc2c(cc1OC)C(=O)C(CC1(F)CCN(Cc3ccc(Br)cc3F)CC1)C2] |
| DC16 | 2-((4-fluoro-1-(4-(trifluoromethyl)benzyl)piperidin-4-yl)methyl)-5,6-dimethoxy-2,3-dihydro-1H-inden-1-one | 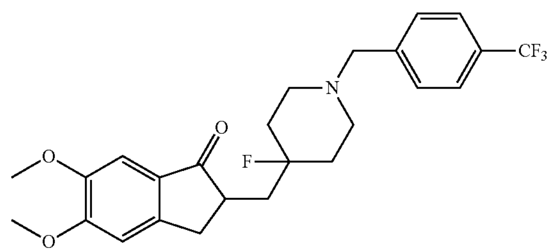 [SMILES: COc1cc2c(cc1OC)C(=O)C(CC1(F)CCN(Cc3ccc(C(F)(F)F)cc3)CC1)C2] |
| DC17 | 2-((4-fluoro-1-(2,4,5-trifluorobenzyl)piperidin-4-yl)methyl)-5,6-dimethoxy-2,3-dihydro-1H-inden-1-one | 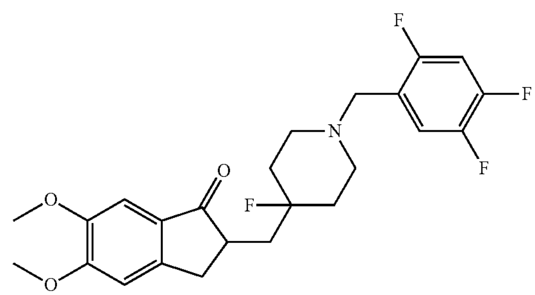 [SMILES: COc1cc2c(cc1OC)C(=O)C(CC1(F)CCN(Cc3cc(F)c(F)cc3F)CC1)C2] |
| DC18 | 2-((4-fluoro-1-(2-(trifluoromethyl)benzyl)piperidin-4-yl)methyl)-5,6-dimethoxy-2,3-dihydro-1H-inden-1-one | 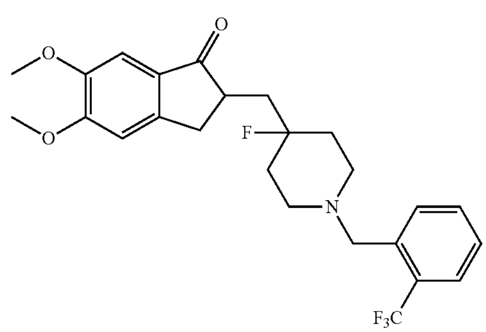 [SMILES: COc1cc2c(cc1OC)C(=O)C(CC1(F)CCN(Cc3ccccc3C(F)(F)F)CC1)C2] |
| DC19 | 2-((1-benzyl-4-fluoropiperidin-4-yl)methyl)-5,6-dimethoxy-2,3-dihydro-1H-inden-1-one | 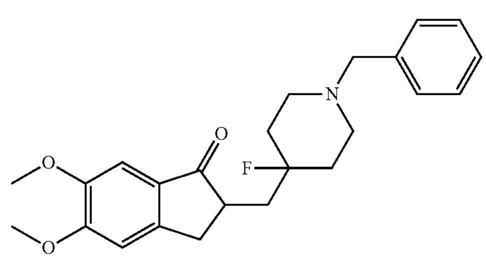 [SMILES: COc1cc2c(cc1OC)C(=O)C(CC1(F)CCN(Cc3ccccc3)CC1)C2] |

-continued

| No. | name | structure |
|---|---|---|
| DC20 | 2-((4-fluoro-1-(2-fluorobenzyl)piperidin-4-yl)methyl)-5,6-dimethoxy-2,3-dihydro-1H-inden-1-one | 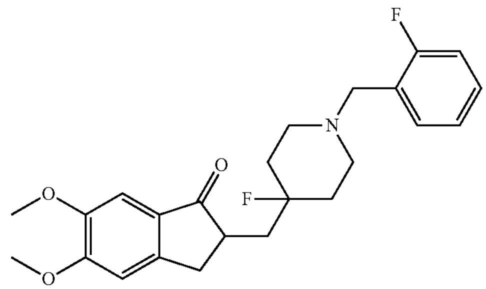 [SMILES: COc1cc2c(cc1OC)C(=O)C(CC1(F)CCN(Cc3ccccc3F)CC1)C2] |
| DC21 | 2-((4-fluoro-1-(3-fluorobenzyl)piperidin-4-yl)methyl)-5,6-dimethoxy-2,3-dihydro-1H-inden-1-one | 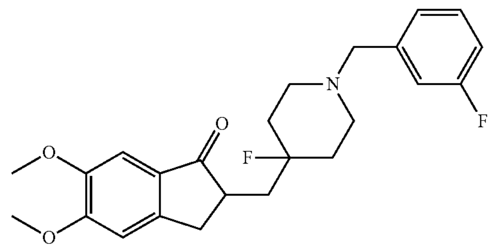 [SMILES: COc1cc2c(cc1OC)C(=O)C(CC1(F)CCN(Cc3cccc(F)c3)CC1)C2] |
| DC22 | 2-((1-(3,5-bis(trifluoromethyl)benzyl)-4-fluoropiperidin-4-yl)methyl)-5,6-dimethoxy-2,3-dihydro-1H-inden-1-one | 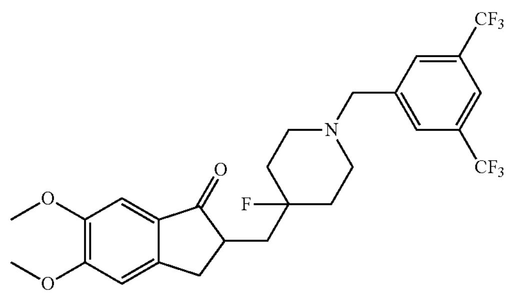 [SMILES: COc1cc2c(cc1OC)C(=O)C(CC1(F)CCN(Cc3cc(C(F)(F)F)cc(C(F)(F)F)c3)CC1)C2] |
| DC27 | 2-((1-(3,5-difluorobenzyl)-4-fluoropiperidin-4-yl)methyl)-5,6-dimethoxy-2,3-dihydro-1H-inden-1-one | 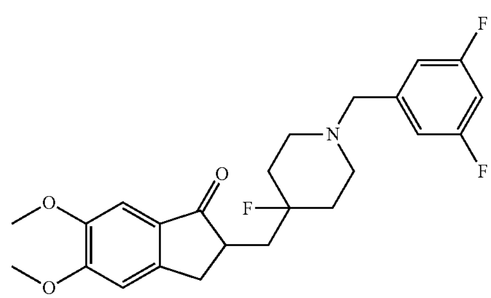 [SMILES: COc1cc2c(cc1OC)C(=O)C(CC1(F)CCN(Cc3cc(F)cc(F)c3)CC1)C2] |
| DC28 | 2-((4-fluoro-1-((perfluorophenyl)methyl)piperidin-4-yl)methyl)-5,6-dimethoxy-2,3-dihydro-1H-inden-1-one | 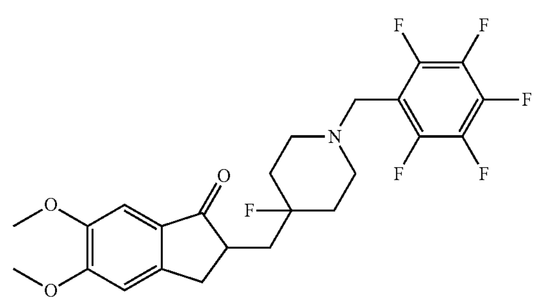 [SMILES: COc1cc2c(cc1OC)C(=O)C(CC1(F)CCN(Cc3c(F)c(F)c(F)c(F)c3F)CC1)C2] |

-continued

| No. | name | structure |
|---|---|---|
| DC29 | 2-((4-fluoro-1-(3-methylbenzyl)piperidin-4-yl)methyl)-5,6-dimethoxy-2,3-dihydro-1H-inden-1-one | 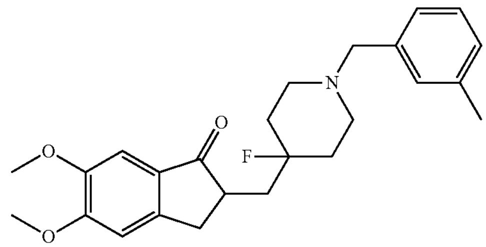 |
| DC30 | 2-((4-fluoro-1-(3-(trifluoromethyl)benzyl)piperidin-4-yl)methyl)-5,6-dimethoxy-2,3-dihydro-1H-inden-1-one | 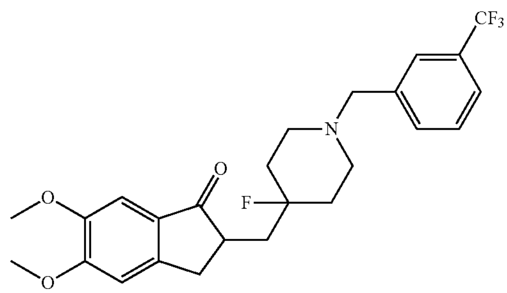 [SMILES: COc1cc2c(cc1OC)C(=O)C(CC1(F)CCN(Cc3cccc(C(F)(F)F)c3)CC1)C2] |
| DC31 | 2-((1-(cyclobutylmethyl)-4-fluoropiperidin-4-yl)methyl)-5,6-dimethoxy-2,3-dihydro-1H-inden-1-one | 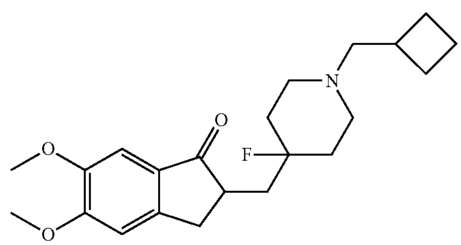 [SMILES: COc1cc2c(cc1OC)C(=O)C(CC1(F)CCN(CC3CCC3)CC1)C2] |
| DC32 | 2-((1-(cyclopentylmethyl)-4-fluoropiperidin-4-yl)methyl)-5,6-dimethoxy-2,3-dihydro-1H-inden-1-one | 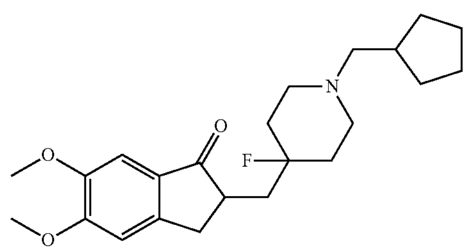 [SMILES: COc1cc2c(cc1OC)C(=O)C(CC1(F)CCN(CC3CCCC3)CC1)C2] |
| DC33 | 2-((1-(cyclohexylmethyl)-4-fluoropiperidin-4-yl)methyl)-5,6-dimethoxy-2,3-dihydro-1H-inden-1-one | 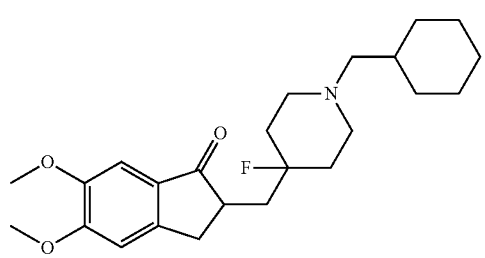 [SMILES: COc1cc2c(cc1OC)C(=O)C(CC1(F)CCN(CC3CCCCC3)CC1)C2] |
| DC34 | 2-((1-(cycloheptylmethyl)-4-fluoropiperidin-4-yl)methyl)-5,6-dimethoxy-2,3-dihydro-1H-inden-1-one | 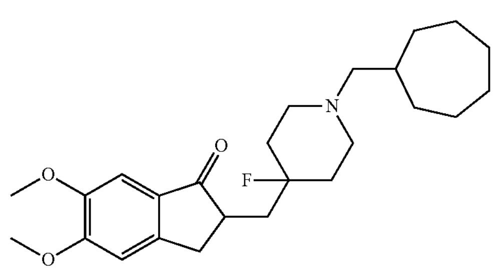 [SMILES: COc1cc2c(cc1OC)C(=O)C(CC1(F)CCN(CC3CCCCCC3)CC1)C2] |

| No. | name | structure |
|---|---|---|
| DC35 | 2-((4-fluoro-1-(2,3,5-trifluorobenzyl)piperidin-4-yl)methyl)-5,6-dimethoxy-2,3-dihydro-1H-inden-1-one | 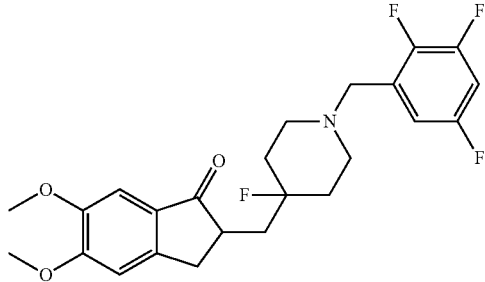 [SMILES: COc1cc2c(cc1OC)C(=O)C(CC1(F)CCN(Cc3cc(F)cc(F)c3F)CC1)C2] |
| DC36 | 2-((1-([1,1'-biphenyl]-4-yl-methyl)-4-fluoropiperidin-4-yl)methyl)-5,6-dimethoxy-2,3-dihydro-1H-inden-1-one | 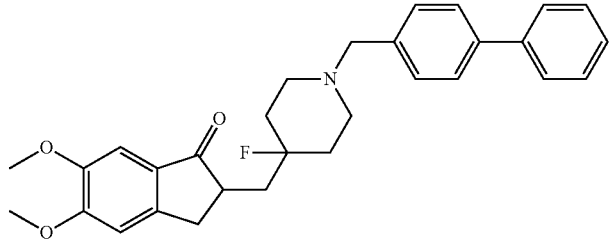 [SMILES: COc1cc2c(cc1OC)C(=O)C(CC1(F)CCN(Cc3ccc(-c4ccccc4)cc3)CC1)C2] |
| DC41 | 2-((3-fluoro-8-(4-nitrobenzyl)-8-azabicyclo[3.2.1]octan-3-yl)methyl)-5,6-dimethoxy-2,3-dihydro-1H-inden-1-one | 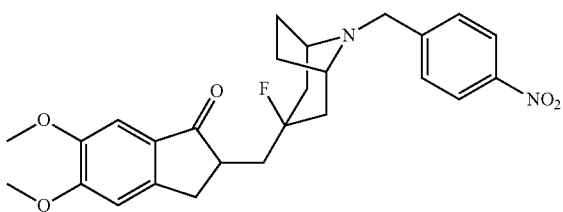 [SMILES: COc1cc2c(cc1OC)C(=O)C(CC1(F)CC3CCC(C1)N3Cc1ccc([N+](=O)[O-])cc1)C2] |
| DC43 | 2-((3-((5,6-dimethoxy-1-oxo-2,3-dihydro-1H-inden-2-yl)methyl)-3-fluoro-8-azabicyclo[3.2.1]octan-8-yl)methyl)benzonitrile | 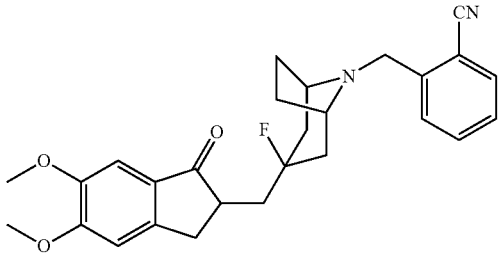 [SMILES: COc1cc2c(cc1OC)C(=O)C(CC1(F)CC3CCC(C1)N3Cc1ccccc1C#N)C2] |
| DC44 | 2-((8-(3,5-dimethylbenzyl)-3-fluoro-8-azabicyclo[3.2.1]octan-3-yl)methyl)-5,6-dimethoxy-2,3-dihydro-1H-inden-1-one | 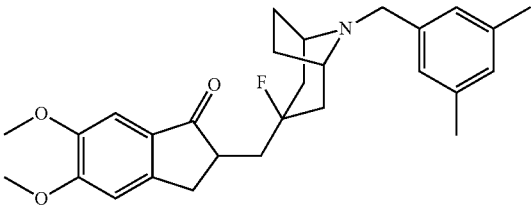 |
| DC45 | 2-((3-fluoro-8-(4-fluorobenzyl)-8-azabicyclo[3.2.1]octan-3-yl)methyl)-5,6-dimethoxy-2,3-dihydro-1H-inden-1-one | 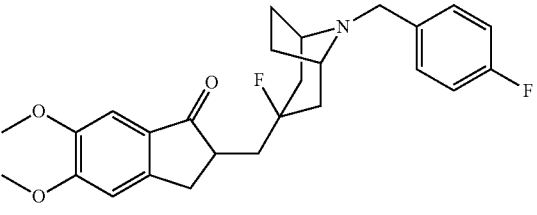 [SMILES: COc1cc2c(cc1OC)C(=O)C(CC1(F)CC3CCC(C1)N3Cc1ccc(F)cc1)C2] |

-continued

| No. | name | structure |
|---|---|---|
| DC47 | 2-((8-(4-(tert-butyl)benzyl)-3-fluoro-8-azabicyclo[3.2.1]octan-3-yl)methyl)-5,6-dimethoxy-2,3-dihydro-1H-inden-1-one | 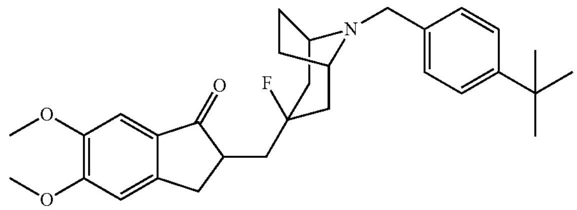 [SMILES: COc1cc2c(cc1OC)C(=O)C(CC1(F)CC3CCC(C1)N3Cc1ccc(C(C)(C)C)cc1)C2] |
| DC48 | 2-((3-fluoro-8-(2-fluoro-6-nitrobenzyl)-8-azabicyclo[3.2.1]octan-3-yl)methyl)-5,6-dimethoxy-2,3-dihydro-1H-inden-1-one | 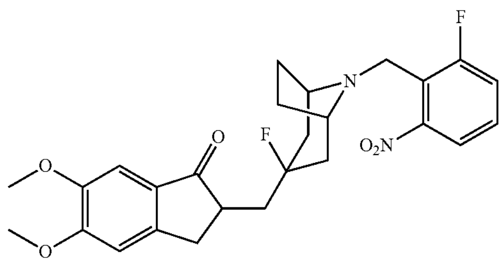 [SMILES: COc1cc2c(cc1OC)C(=O)C(CC1(F)CC3CCC(C1)N3Cc1c(F)cccc1[N+](=O)[O-])C2] |
| DC50 | methyl 4-((3-((5,6-dimethoxy-1-oxo-2,3-dihydro-1H-inden-2-yl)methyl)-3-fluoro-8-azabicyclo[3.2.1]octan-8-yl)methyl)benzoate | 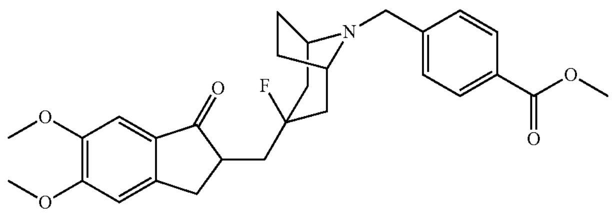 |
| DC51 | 2-((8-(3-bromobenzyl)-3-fluoro-8-azabicyclo[3.2.1]octan-3-yl)methyl)-5,6-dimethoxy-2,3-dihydro-1H-inden-1-one | 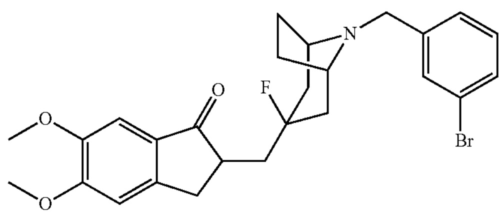 |
| DC52 | 2-(((3-fluoro-8-(2-nitrobenzyl)-8-azabicyclo[3.2.1]octan-3-yl)methyl)-5,6-dimethoxy-2,3-dihydro-1H-inden-1-one | 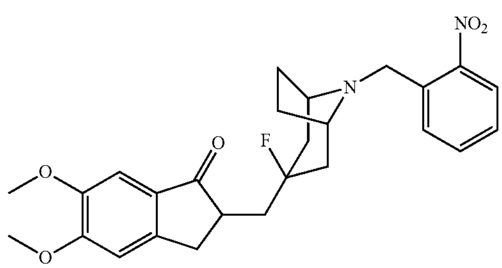 [SMILES: COc1cc2c(cc1OC)C(=O)C(CC1(F)CC3CCC(C1)N3Cc1ccccc1[N+](=O)[O-])C2] |
| DC54 | 2-((8-(2-bromobenzyl)-3-fluoro-8-azabicyclo[3.2.1]octan-3-yl)methyl)-5,6-dimethoxy-2,3-dihydro-1H-inden-1-one | 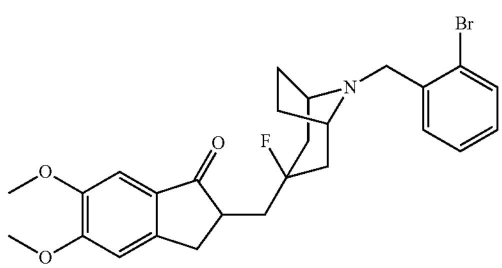 |

-continued

| No. | name | structure |
|---|---|---|
| DC57 | 2-((3-fluoro-8-(2,4,5-trifluorobenzyl)-8-azabicyclo[3.2.1]octan-3-yl)methyl)-5,6-dimethoxy-2,3-dihydro-1H-inden-1-one | 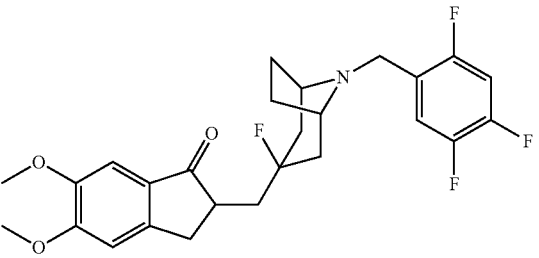 [SMILES: COc1cc2c(cc1OC)C(=O)C(CC1(F)CC3CCC(C1)N3Cc1cc(F)c(F)cc1F)C2] |
| DC59 | 2-((8-benzyl-3-fluoro-8-azabicyclo[3.2.1]octan-3-yl)methyl)-5,6-dimethoxy-2,3-dihydro-1H-inden-1-one | 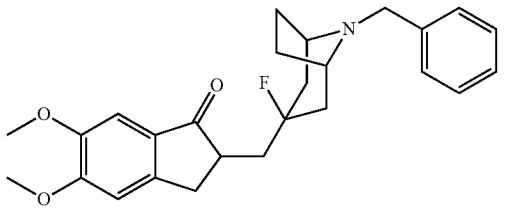 [SMILES: COc1cc2c(cc1OC)C(=O)C(CC1(F)CC3CCC(C1)N3Cc1ccccc1)C2] |
| DC60 | 2-((3-fluoro-8-(2-fluorobenzyl)-8-azabicyclo[3.2.1]octan-3-yl)methyl)-5,6-dimethoxy-2,3-dihydro-1H-inden-1-one | 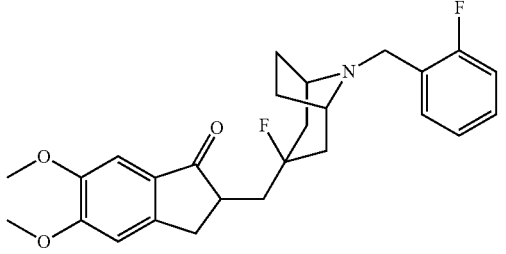 [SMILES: COc1cc2c(cc1OC)C(=O)C(CC1(F)CC3CCC(C1)N3Cc1ccccc1F)C2] |
| DC61 | 2-((3-fluoro-8-(3-fluorobenzyl)-8-azabicyclo[3.2.1]octan-3-yl)methyl)-5,6-dimethoxy-2,3-dihydro-1H-inden-1-one | 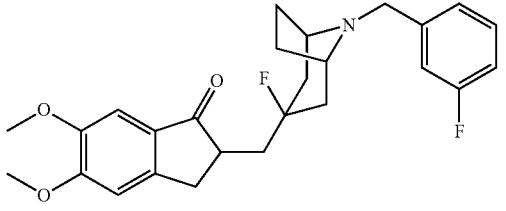 |
| DC68 | 2-((3-fluoro-8-((perfluorophenyl)methyl)-8-azabicyclo[3.2.1]octan-3-yl)methyl)-5,6-dimethoxy-2,3-dihydro-1H-inden-1-one | 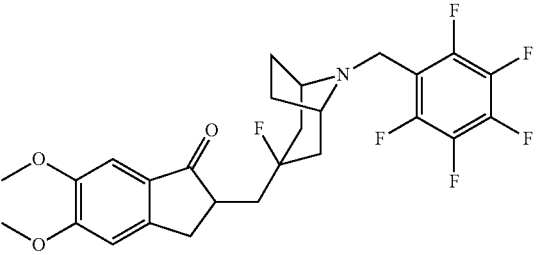 [SMILES: COc1cc2c(cc1OC)C(=O)C(CC1(F)CC3CCC(C1)N3Cc1c(F)c(F)c(F)c(F)c1F)C2] |
| DC69 | 2-((3-fluoro-8-(3-methylbenzyl)-8-azabicyclo[3.2.1]octan-3-yl)methyl)-5,6-dimethoxy-2,3-dihydro-1H-inden-1-one | 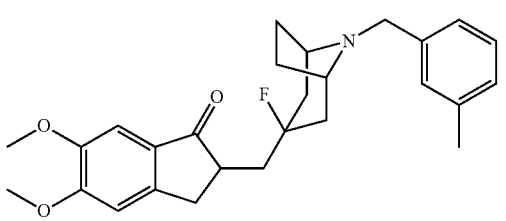 [SMILES: COc1cc2c(cc1OC)C(=O)C(CC1(F)CC3CCC(C1)N3Cc1cccc(C)c1)C2] |

-continued

| No. | name | structure |
|---|---|---|
| DC70 | 2-((3-fluoro-8-(3-(trifluoromethyl)benzyl)-8-azabicyclo[3.2.1]octan-3-yl)methyl)-5,6-dimethoxy-2,3-dihydro-1H-inden-1-one | 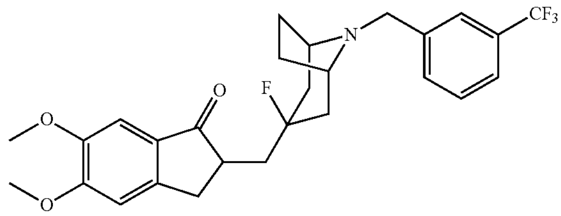 [SMILES: COc1cc2c(cc1OC)C(=O)C(CC1(F)CC3CCC(C1)N3Cc1cccc(C(F)(F)F)c1)C2] |
| DC75 | 2-((3-fluoro-8-(2,3,5-trifluorobenzyl)-8-azabicyclo[3.2.1]octan-3-yl)methyl)-5,6-dimethoxy-2,3-dihydro-1H-inden-1-one | 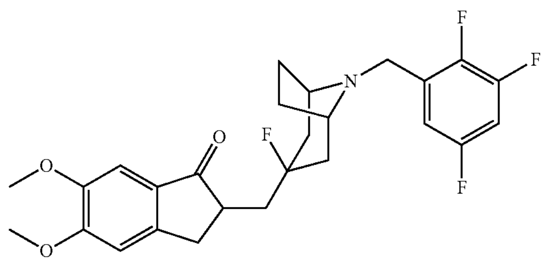 [SMILES: COc1cc2c(cc1OC)C(=O)C(CC1(F)CC3CCC(C1)N3Cc1cc(F)cc(F)c1F)C2] |
| DC76 | 2-((8-([1,1'-biphenyl]-4-ylmethyl)-3-fluoro-8-azabicyclo[3.2.1]octan-3-yl)methyl)-5,6-dimethoxy-2,3-dihydro-1H-inden-1-one | 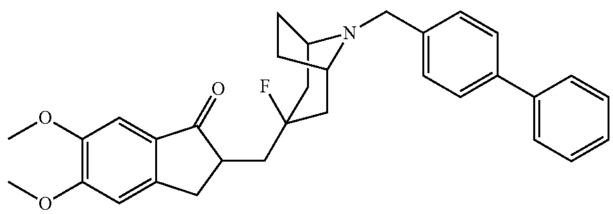 [SMILES: COc1cc2c(cc1OC)C(=O)C(CC1(F)CC3CCC(C1)N3Cc1ccc(-c3ccccc3)cc1)C2] |
| DC23 | 2-((1-benzoyl-4-fluoropiperidin-4-yl)methyl)-5,6-dimethoxy-2,3-dihydro-1H-inden-1-one | 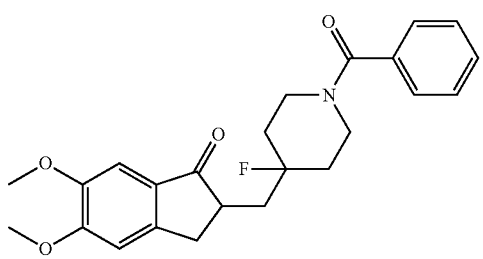 [SMILES: COc1cc2c(cc1OC)C(=O)C(CC1(F)CCN(C(=O)c3ccccc3)CC1)C2] |
| DC37 | 2-((4-((5,6-dimethoxy-1-oxo-2,3-dihydro-1H-inden-2-yl)methyl)-4-fluoropiperidin-1-yl)methyl)benzonitrile hydrochloride | 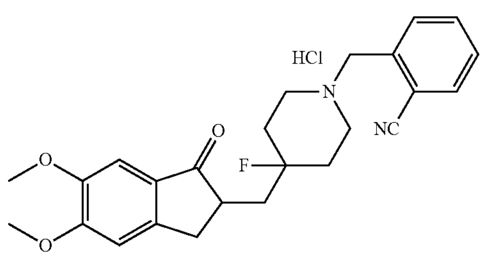 [SMILES: COc1cc2c(cc1OC)C(=O)C(CC1(F)CCN(Cc3ccccc3C#N)CC1)C2 ; Cl] |
| DC38 | 2-((4-fluoro-1-(3-fluorobenzyl)piperidin-4-yl)methyl)-5,6-dimethoxy-2,3-dihydro-1H-inden-1-one hydrochloride | 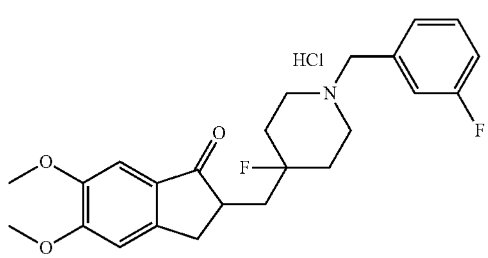 [SMILES: COc1cc2c(cc1OC)C(=O)C(CC1(F)CCN(Cc3cccc(F)c3)CC1)C2 ; Cl] |

-continued

| No. | name | structure |
|---|---|---|
| DC77 | 5,6-diethoxy-2-((4-fluoro-1-(2-fluorobenzyl)piperidin-4-yl)methyl)-2,3-dihydro-1H-inden-1-one | 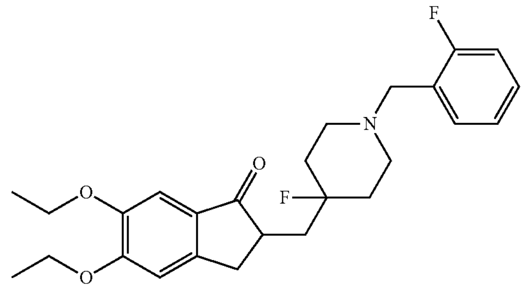 [SMILES: CCOc1cc2c(cc1OCC)C(=O)C(CC1(F)CCN(Cc3ccccc3F)CC1)C2] |
| DC78 | 2-((4-fluoro-1-(2-fluorobenzyl)piperidin-4-yl)methyl)-5,6-dipropoxy-2,3-dihydro-1H-inden-1-one | 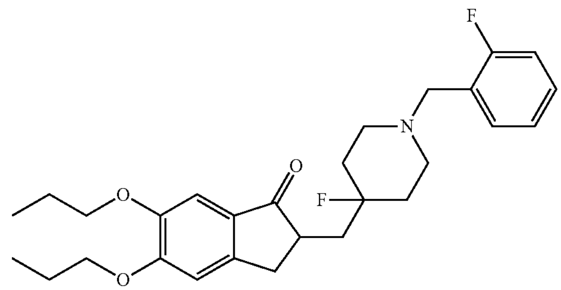 [SMILES: CCCOc1cc2c(cc1OCCC)C(=O)C(CC1(F)CCN(Cc3ccccc3F)CC1)C2] |
| DC79 | 5,6-bis(ethoxymethoxy)-2-((4-fluoro-1-(2-fluorobenzyl)piperidin-4-yl)methyl)-2,3-dihydro-1H-inden-1-one | 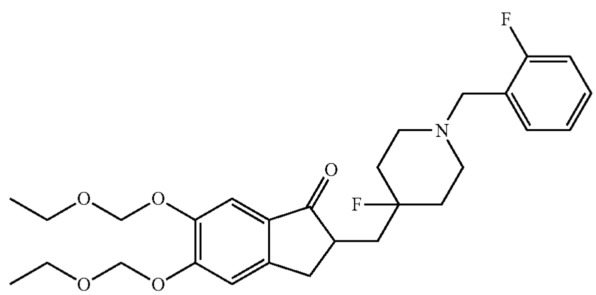 [SMILES: CCOCOc1cc2c(cc1OCOCC)C(=O)C(CC1(F)CCN(Cc3ccccc3F)CC1)C2] |
| DC103 | 2-((4-fluoro-1-(2-fluorobenzyl)piperidin-4-yl)methyl)-5,6-bis(2,2,2-trifluoroethoxy)-2,3-dihydro-1H-inden-1-one | 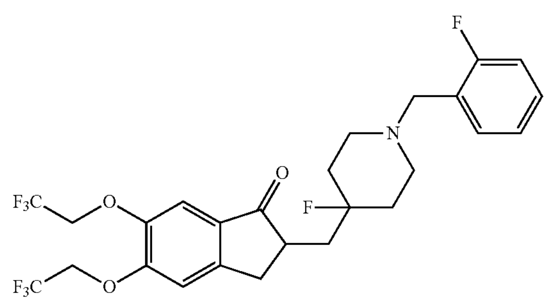 [SMILES: O=C1c2cc(OCC(F)(F)F)c(OCC(F)(F)F)cc2CC1CC1(F)CCN(Cc2ccccc2F)CC1] |
| DC104 | 5,6-bis(difluoromethoxy)-2-((4-fluoro-1-(2-fluorobenzyl)piperidin-4-yl)methyl)-2,3-dihydro-1H-inden-1-one | 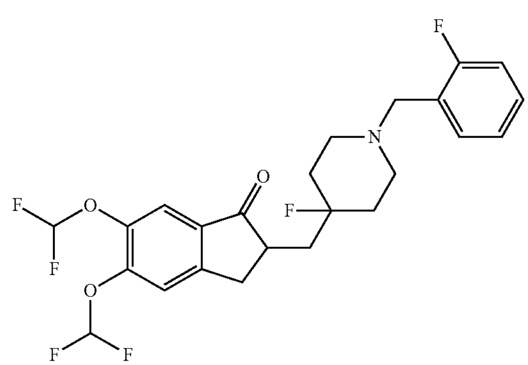 [SMILES: O=C1c2cc(OC(F)F)c(OC(F)F)cc2CC1CC1(F)CCN(Cc2ccccc2F)CC1] |

-continued

| No. | name | structure |
|---|---|---|
| DC105 | 5,6-bis(2,2-difluoroethoxy)-2-((4-fluoro-1-(2-fluorobenzyl)piperidin-4-yl)methyl)-2,3-dihydro-1H-inden-1-one | 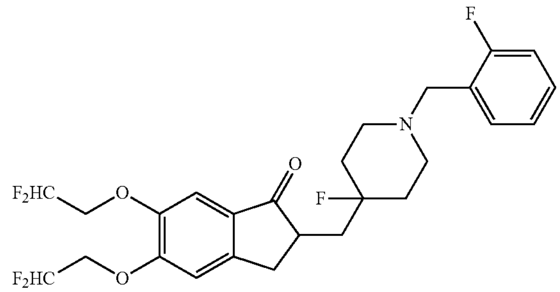 [SMILES: O=C1c2cc(OCC(F)F)c(OCC(F)F)cc2CC1CC1(F)CCN(Cc2ccccc2F)CC1] |
| DC106 | 5,6-dichloro-2-((4-fluoro-1-(2-fluorobenzyl)piperidin-4-yl)methyl)-2,3-dihydro-1H-inden-1-one | 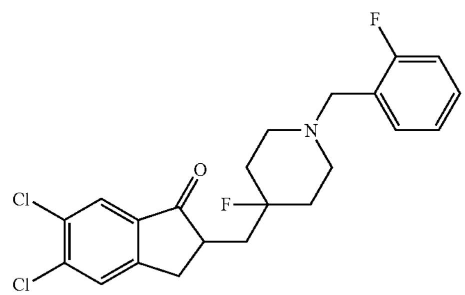 [SMILES: O=C1c2cc(Cl)c(Cl)cc2CC1CC1(F)CCN(Cc2ccccc2F)CC1] |
| DC107 | methyl 4-((5,6-dimethoxy-1-oxo-2,3-dihydro-1H-inden-2-yl)methyl)-4-fluoro-1-(2-fluorobenzyl)piperidine-2-carboxylate | 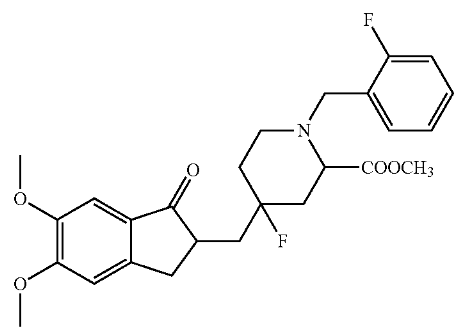 [SMILES: COC(=O)C1CC(F)(CC2Cc3cc(OC)c(OC)cc3C2=O)CCN1Cc1ccccc1F] |
| DC108 | 4-((5,6-dimethoxy-1-oxo-2,3-dihydro-1H-inden-2-yl)methyl)-4-fluoro-1-(2-fluorobenzyl)piperidine-2-carboxylic acid | 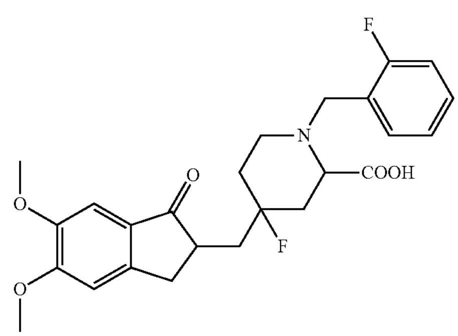 [SMILES: COc1cc2c(cc1OC)C(=O)C(CC1(F)CCN(Cc3ccccc3F)C(C(=O)O)C1)C2] |
| DC109 | 2-((4-fluoro-1-(2-fluorobenzyl)-2-methylpiperidin-4-yl)methyl)-5,6-dimethoxy-2,3-dihydro-1H-inden-1-one | 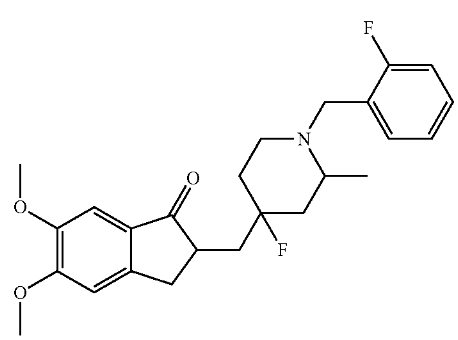 [SMILES: COc1cc2c(cc1OC)C(=O)C(CC1(F)CCN(Cc3ccccc3F)C(C)C1)C2] |

| No. | name | structure |
|---|---|---|
| DC110 | 2-((4-fluoro-1-phenethylpiperidin-4-yl)methyl)-5,6-dimethoxy-2,3-dihydro-1H-inden-1-one | 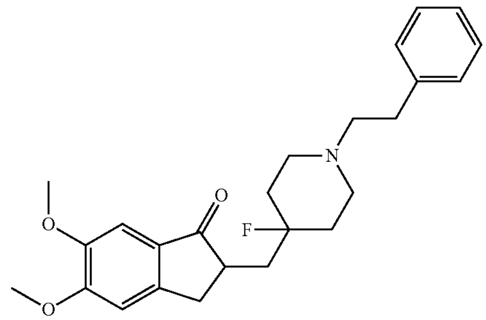 [SMILES: COc1cc2c(cc1OC)C(=O)C(CC1(F)CCN(CCc3ccccc3)CC1)C2] |
| DC111 | 2-((4-fluoro-1-(2-fluorophenethyl)piperidin-4-yl)methyl)-5,6-dimethoxy-2,3-dihydro-1H-inden-1-one | 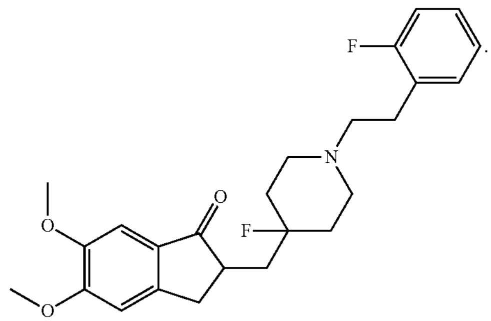 [SMILES: COc1cc2c(cc1OC)C(=O)C(CC1(F)CCN(CCc3ccccc3F)CC1)C2] |

The compounds of the present invention have asymmetric center, chiral axis and chiral plane, and can be presented in the form of racemates, R-isomer or S-isomers. For a skilled person in the art, a R-isomer and/or S-isomer can be obtained from a racemate using conventional technical means by resolution.

The present invention provides pharmaceutically acceptable salts of compounds as shown in general formula I, in particular conventional pharmaceutically acceptable salts obtained from the reaction of compounds as shown in general formula I with inorganic acid or organic acid. For example, conventional pharmaceutically acceptable salts can be obtained from the reaction of compounds as shown in general formula I with inorganic acid or organic acid, the inorganic acid includes hydrochloric acid, hydrobromic acid, sulfuric acid, nitric acid, amino sulfoacid, phosphoric acid and the like, and the organic acid includes citric acid, tartaric acid, lactic acid, pyruvic acid, acetic acid, benzenesulfonic acid, p-toluenesulfonic acid, methanesulfonic acid, naphthalenesulfonic acid, ethanesulfonic acid, naphthalene disulfonic acid, maleic acid, malic acid, malonic acid, fumaric acid, succinic acid, propionic acid, oxalic acid, trifluoroacetic acid, stearic acid, pamoic acid, hydroxy maleic acid, phenylacetic acid, benzoic acid, salicylic acid, glutamic acid, ascorbic acid, p-amino benzenesulfonic acid, 2-acetoxy-benzoic acid, isethionic acid and the like; or sodium salts, potassium salts, calcium salts, aluminum salts or ammonium salts from the reaction of compounds as shown in general formula I with inorganic base; or methylamine salts, ethylamine salts or ethanolamine salts from the reaction of compounds as shown in general formula I with organic base.

In another aspect of the present invention, a preparation method for compounds as shown in general formula I is provided, which is carried out according to the following scheme 1 or scheme 2.

Scheme 1:

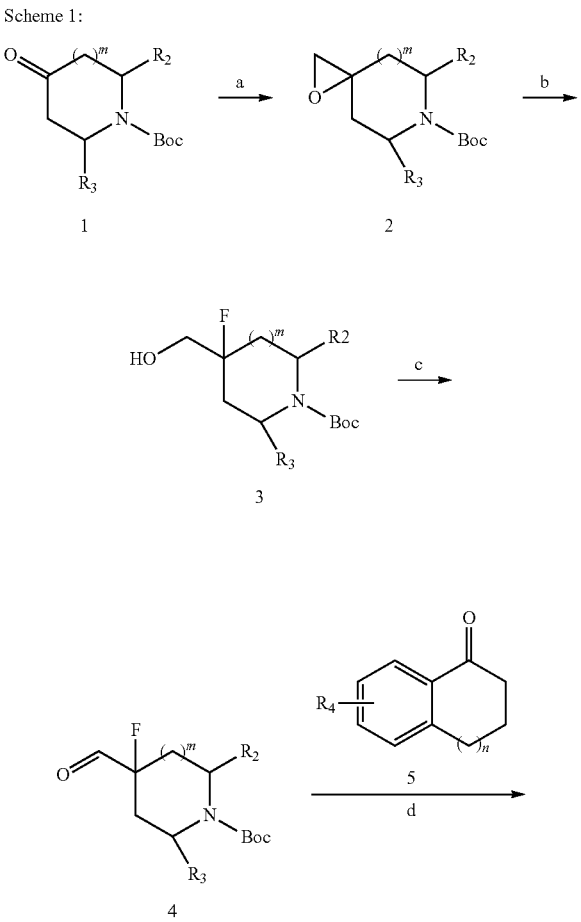

-continued

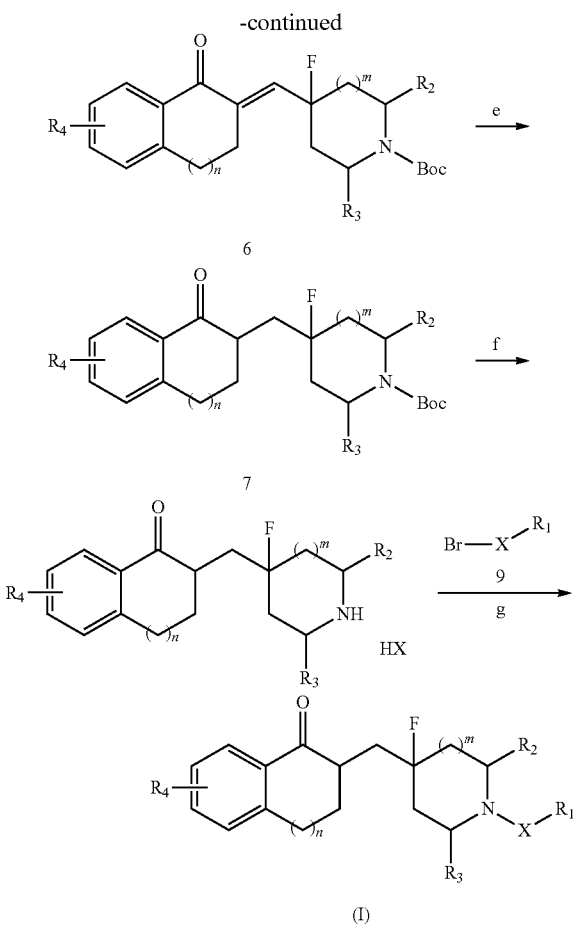

wherein the definitions of $R_1$, $R_2$, $R_3$, $R_4$, X, m and n are the same as those defined in general formula I.

Step a: Dimethylsulfoxide is added and heated with stirring. NaH is added and stirred. After cooling, trimethylsulfoxonium iodide is added, and then compound 1 is added to obtain epoxide 2; the heating temperature is 60-100° C.

Step b: Intermediate 2 is dissolved into an organic solvent and cooled to −10° C.~−40° C. 1-10 equivalents of hydrogen fluoride solution in pyridine is added and reacts until the raw materials disappear. Intermediate 3 can be obtained through isolation and purification; the organic solvent can be tetrahydrofuran, diethyl ether, dimethylformamide, glycol dimethyl ether, glycol diethyl ether, dioxane, ethanol, methanol, ethyl acetate, dichloromethane, or a mixture thereof.

Step c: Intermediate 3 is dissolved into an organic solvent and an oxidant is added for the oxidization of alcohol hydroxyl to aldehyde group to give intermediate 4; the organic solvent can be tetrahydrofuran, diethyl ether, dimethylformamide, glycol dimethyl ether, glycol diethyl ether, dioxane, ethanol, methanol, ethyl acetate, dichloromethane, or a mixture thereof; and said oxidant can be selected from a group consisting of PCC, PDC, Dess-Martin periodinane, Swern oxidant, $H_2O_2$, potassium permanganate, and manganese dioxide.

Step d: Intermediate 4 is dissolved into an organic solvent and compound 5 is added. Then a strong base is added until the raw materials disappear. Intermediate 6 can be obtained through isolation and purification; the organic solvent can be tetrahydrofuran, diethyl ether, dimethylformamide, glycol dimethyl ether, glycol diethyl ether, dioxane, ethanol, methanol, ethyl acetate, dichloromethane, or a mixture thereof; and the strong base is NaOH, KOH, sodium ethoxide or sodium methoxide.

Step e: Intermediate 6 is dissolved into an organic solvent and palladium on carbon is added. Then hydrogen gas is charged for reduction to obtain intermediate 7; the organic solvent can comprise tetrahydrofuran, diethyl ether, dimethylformamide, glycol dimethyl ether, glycol diethyl ether, dioxane, ethanol, methanol, ethyl acetate, dichloromethane.

Step f: Intermediate 7 is dissolved into an organic solvent and trifluoroacetic acid (TFA) or hydrochloric acid (HCl) in organic solvent is added to remove Boc protecting group to obtain intermediate 8; the organic solvent can be tetrahydrofuran, diethyl ether, dimethylformamide, glycol dimethyl ether, glycol diethyl ether, dioxane, ethanol, methanol, ethyl acetate, dichloromethane or a mixture thereof.

Step g: Intermediate 8 is dissolved into an organic solvent and compound 9 is added. Then a certain amount of base is added and stirred until the raw materials disappear to obtain final product; the organic solvent can be tetrahydrofuran, diethyl ether, dimethylformamide, glycol dimethyl ether, glycol diethyl ether, dioxane, ethanol, methanol, ethyl acetate, dichloromethane or a mixture thereof; and the base may be sodium acetate, NaOH, KOH, sodium ethoxide, sodium methoxide, sodium carbonate, potassium carbonate, triethylamine or diisopropylamine.

Scheme 2:

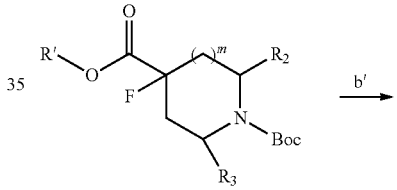

R' = H, $CH_3$, $C_2H_5$

1'

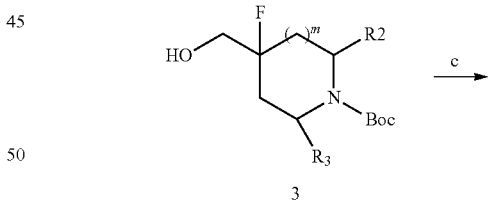

3

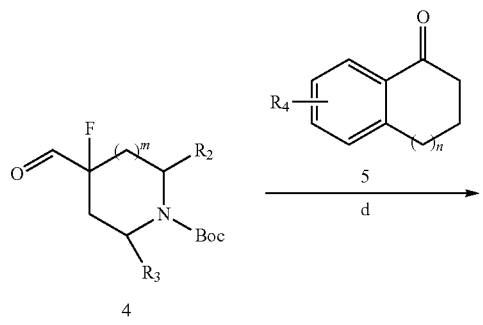

4

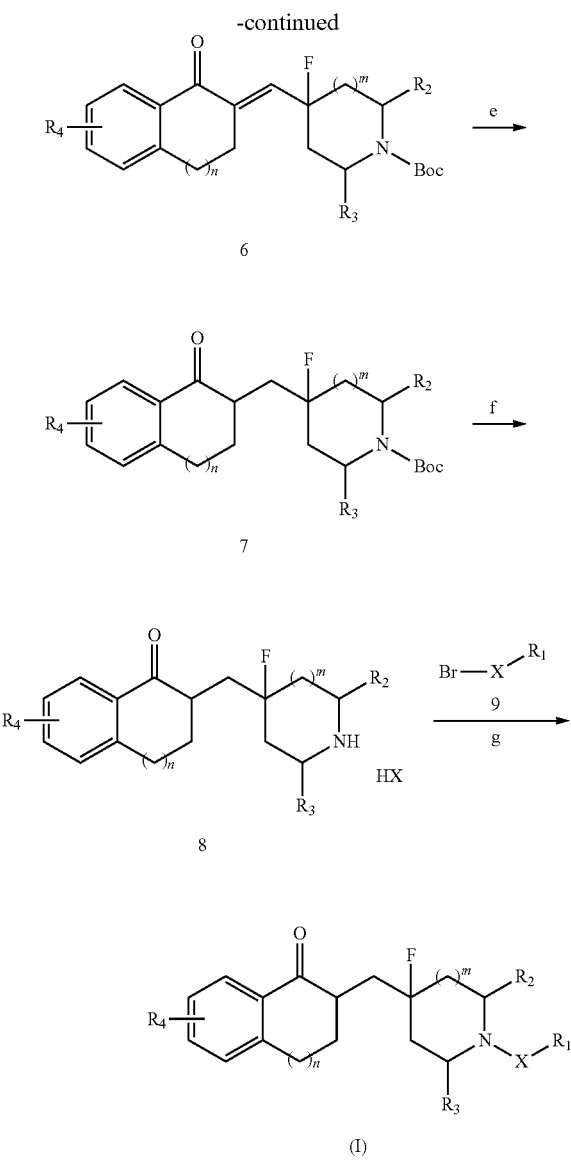

wherein the definitions of $R_1$, $R_2$, $R_3$, $R_4$, X, m and n are the same as those defined in above general formula I.

Step b': Compound 1' is reduced by a reductant to prepare intermediate 2; the reductant can be selected from sodium borohydride, potassium borohydride, lithium borohydride, lithium aluminium hydride ($LiAlH_4$).

Step c-g: The specific operations are identical with those in scheme 1.

In another aspect of the present invention, a pharmaceutical composition containing therapeutically effective amount of one or more of above compounds as shown in general formula I, pharmaceutically acceptable salts, enantiomers, diastereoisomer and racemates, and optionally one or more pharmaceutically acceptable carriers, excipients, adjuvants, auxiliary materials and/or diluents. The auxiliary material is, for example, odor agent, flavoring agent, sweetener and the like.

The pharmaceutical composition provided in the present invention preferably comprises 1-99% by weight of active ingredients, and the preferable proportion is that the compound as shown in general formula I as active ingredient occupies 65 wt %-99 wt % base on the total weight and the rest is pharmaceutically acceptable carriers, diluent or solution or salt solution.

The compounds and pharmaceutical compositions of the present invention may be provided in various forms, such as tablets, capsules, powders, syrups, solutions, suspensions, aerosols and the like, and may be present in a suitable solid or liquid carrier or diluent and suitable disinfector for injection or infusion.

The various dosage forms of pharmaceutical compositions of the present invention may be prepared according to conventional preparation methods in the pharmaceutical field. The unit dosage of formulation thereof comprises 0.05-200 mg of compound as shown in general formula I, preferably, the unit dosage of formulation thereof comprises 0.1 mg-100 mg of compound as shown in general formula I.

The compounds and pharmaceutical compositions of the present invention may be applied clinically to mammals, including humans and animals, through the administration route of mouth, nose, skin, lung, or gastrointestinal tract etc., most preferably through the mouth. Most preferably, a daily dose is 0.01-200 mg/kg of body weight, one-time use, or 0.01-100 mg/kg of body weight in divided doses. No matter how to administrate, the personal optimal dose should be determined according to the specific treatment. Generally, initial dose is a small dose and the dose is gradually increased until the most suitable dose is established.

Another aspect of the present invention is to provide an acetylcholinesterase inhibitor comprising one or more of above compounds as shown in general formula I, pharmaceutically acceptable salts, racemates, R-isomers, S-isomers thereof or a mixture thereof, and optional one or more pharmaceutically acceptable carriers, excipients, adjuvants, auxiliary materials and/or diluents.

The compounds and pharmaceutical compositions of the present invention can be used to treat or prevent acetylcholinesterase-related nerve system diseases, including but not limited to senile dementia, Parkinson's disease, epilepsy or schizophrenia and the like.

Therefor, another aspect of the present invention is to provide a use of above compounds as shown in general formula I, pharmaceutically acceptable salts, racemates, R-isomers, S-isomers thereof or a mixture thereof for the preparation of medicaments for the treatment of acetylcholinesterase-related nerve system diseases, such as Alzheimer's disease, Parkinson's disease, epilepsy, schizophrenia and so on.

Another aspect of the present invention is to provide a method for treating acetylcholinesterase-related nerve system diseases, such as Alzheimer's disease, Parkinson's disease, epilepsy, schizophrenia, etc. comprising administrating one or more of above compounds as shown in general formula I, pharmaceutically acceptable salts, racemates, R-isomers, S-isomers thereof or a mixture thereof to a patient in need thereof.

MODES FOR CARRYING OUT THE INVENTION

The present invention will be further illustrated in the following examples. These examples are intended to illustrate the invention, but not limit the invention in any way. The starting materials used in the present invention are purchased from the market unless otherwise indicated.

Example 1

Preparation of 2-((4-fluoro-1-(4-nitrobenzyl)piperidin-4-yl)methyl)-5,6-dimethoxy-2,3-dihydro-1H-inden-1-one (DC1)

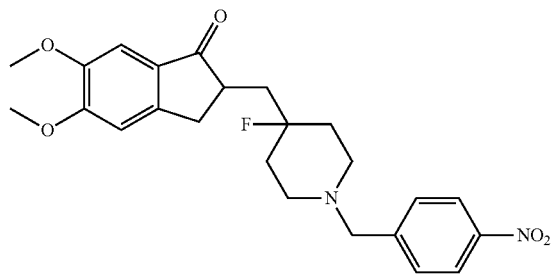 [SMILES: COc1cc2c(cc1OC)C(=O)C(CC1(F)CCN(Cc3ccc([N+](=O)[O-])cc3)CC1)C2]

1.1 synthesis of tert-butyl 1-oxa-6-azaspiro[2.5]octane-6-carboxylate

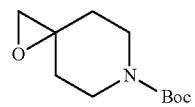

130 mL of dimethylsulfoxide (DMSO) was added to a 250 mL of eggplant-shaped flask and heated with stirring. 5 g of NaH solid was weighed and added to DMSO solution and then stirred for another 12 hours. Heating was stopped and the reaction mixture was cooled to room temperature. 25 g of trimethylsulfoxonium iodide was added and stirred at room temperature for 24 hours. 25 g of N-t-butoxycarbonyl-piperidone pre-dissolved in DMSO was added to the reaction mixture and stirred for another 12 hours. The reaction was monitored by thin layer chromatography (TLC). When the reaction was completed, 100-200 mL of water was added and the reaction mixture was extracted with 100 mL of ethyl acetate (EA) for three times. The organic layer was washed with 30 mL of saturated brine for three times, and then dried by a rotatory evaporator to obtain 28 g 1-oxa-6-azaspiro[2.5]octane-6-carboxylate as colorless liquid.

1.2 synthesis of tert-butyl 4-fluoro-4-(hydroxymethyl)piperidine-1-carboxylate

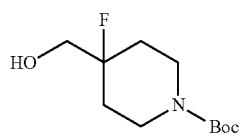

28 g of 1-oxa-6-azaspiro[2.5]octane-6-carboxylate was dissolved in 100 mL of dichloromethane (DCM) and cooled. 120 mL of 70% hydrogen fluoride solution in pyridine was added and reacted for another 12 hours. When the reaction was completed, 100 mL of water was added. The reaction mixture was extracted with 100 mL of DCM for three times and purified by chromatography on silica gel (petroleum ether (PE):ethyl acetate (EA)=4:1) and dried by a rotatory evaporator to obtain 21 g of 4-fluoro-4-(hydroxymethyl)piperidine-1-carboxylate as basically colorless liquid product.

1.3 synthesis of tert-butyl 4-fluoro-4-formylpiperidine-1-carboxylate

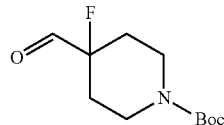 [SMILES: CC(C)(C)OC(=O)N1CCC(F)(C=O)CC1]

3.5 g of 4-fluoro-4-(hydroxymethyl)piperidine-1-carboxylate was dissolved in 20 mL of organic solvent and 16 g of Dess-Martin periodinane was added and stirred at room temperature for 14 hours. The reaction was completed. 50 mL of dichloromethane was added and water was added for extraction. The extraction phase was washed by saturated sodium bicarbonate solution and then dried by a rotatory evaporator to obtain tert-butyl 4-fluoro-4-formylpiperidine-1-carboxylate as white liquid.

1.4 synthesis of tert-butyl 4-((5,6-dimethoxy-1-oxo-1H-inden-2(3H)-ylidene)methyl)-4-fluoropiperidine-1-carboxylate

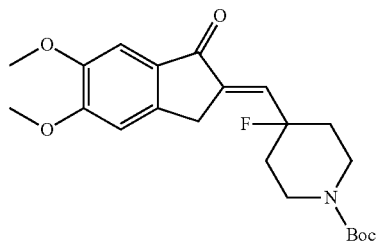 [SMILES: COc1cc2c(cc1OC)C(=O)/C(=C/C1(F)CCN(C(=O)OC(C)(C)C)CC1)C2]

tert-butyl 4-fluoro-4-formylpiperidine-1-carboxylate was dissolved in 25 mL of tetrahydrofuran and 1.4 g of 5,6-dimethoxyindanone and 1.8 g of sodium hydroxide were added. The colour of the reaction liquid changed from yellow to brown. After 12 hours, the reaction was completed. The reaction mixture was purified by column chromatography (PE:EA=4:1) to obtain 1.4 g of tert-butyl 4-((5,6-dimethoxy-1-oxo-1H-inden-2(3H)-ylidene)methyl)-4-fluoropiperidine-1-carboxylate as white solids.

1.5 synthesis of tert-butyl 4-((5,6-dimethoxy-1-oxo-2,3-dihydro-1H-inden-2-yl)methyl)-4-fluoropiperidine-1-carboxylate

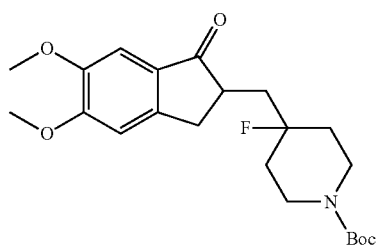 [SMILES: COc1cc2c(cc1OC)C(=O)C(CC1(F)CCN(C(=O)OC(C)(C)C)CC1)C2]

(E)-tert-butyl 4-((5,6-dimethoxy-1-oxo-1H-inden-2(3H)-ylidene)methyl)-4-fluoropiperidine-1-carboxylate was added to 50 mL of methanol and 300 mg of 5% palladium on carbon was added. A hydrogen balloon was installed to replace air for three times. The reaction mixture was stirred at 30° C. for 24-36 hours and filtered by celite. The filtrate was dried by a rotatory evaporator to obtain 1.3 g of tert-butyl 4-((5,6-dimethoxy-1-oxo-2,3-dihydro-1H-inden-2-yl)methyl)-4-fluoropiperidine-1-carboxylate as colorless liquid product.

1.6 synthesis of 2-((4-fluoropiperidin-4-yl)methyl)-5,6-dimethoxy-2,3-dihydro-1H-inden-1-one

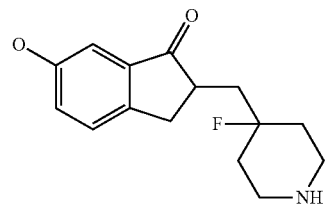 [SMILES: O=C1c2cc(O)ccc2CC1CC1(F)CCNCC1]

50 mL of dioxane solution was added to tert-butyl 4-((5,6-dimethoxy-1-oxo-2,3-dihydro-1H-inden-2-yl)methyl)-4-fluoropiperidine-1-carboxylate and 20 mL of hydrochloric acid saturated dioxane solution was added and stirred at room temperature thereby precipitating white solids. The reaction was monitored by thin-layer chromatography (TLC). After filtered and dried by an oil pump, 1 g of 2-((4-fluoropiperidin-4-yl)methyl)-5,6-dimethoxy-2,3-dihydro-1H-inden-1-one as white solids was obtained.

1.7 Synthesis of Final Product DC1

1 eq of 4-nitrobenzyl bromide, 150 mg of anhydrous sodium carbonate and 5 mL of anhydrous ethanol were added to 50 mg of 2-((4-fluoropiperidin-4-yl)methyl)-5,6-dimethoxy-2,3-dihydro-1H-inden-1-one and stirred at room temperature for 12-24 hours. The reaction was completed. The reaction mixture was dried by a rotatory evaporator and 5 mL water was added. The mixture was extracted by EA, then dried by a rotator evaporator and purified to obtain about 20-40 mg of DC1 as colorless and transparent solids. 1H NMR (CDCl3, 400 MHz) δ 8.18 (d, J=8.4, 2H), 7.52 (d, J=8.4, 2H), 7.17 (s, 1H), 6.86 (s, 1H), 3.96 (s, 3H), 3.90 (s, 3H), 3.63 (s, 2H), 3.30-3.36 (m, 1H), 2.86-2.91 (m, 4H), 2.37-2.44 (m, 3H), 1.91-2.02 (m, 1H), 1.75-1.90 (m, 2H), 1.64-1.67 (m, 2H); LRMS (EI) m/z 442 (M+).

Example 2

Preparation of 2-((4-((5,6-dimethoxy-1-oxo-2,3-dihydro-1H-inden-2-yl)methyl)-4-fluoropiperidin-1-yl)methyl)benzonitrile (DC3)

4-nitrobenzyl bromide was replaced by 2-cyanobenzyl bromide and the rest of raw materials, reagents and the preparation were identical with those in example 1. DC3 was obtained in 80% yield. $^1$H NMR (CDCl$_3$, 400 MHz) δ 7.65 (m, 1H), 7.55 (m, 2H), 7.36 (m, 1H), 7.17 (s, 1H), 6.86 (s, 1H), 3.98 (s, 3H), 3.89 (s, 3H), 3.65 (s, 2H), 3.28-3.34 (m, 1H), 2.67-2.91 (m, 4H), 2.39-2.51 (m, 3H), 1.91-2.02 (m, 1H), 1.62-2.03 (m, 4H); LRMS (EI) m/z 422 (M$^+$).

Example 3

Preparation of 2-((1-(3,5-dimethylbenzyl)-4-fluoropiperidin-4-yl)methyl)-5,6-dimethoxy-2,3-dihydro-1H-inden-1-one (DC4)

4-nitrobenzyl bromide was replaced by 3,5-dimethylbenzyl bromide and the rest of raw materials, reagents and the preparation were identical with those in example 1. DC4 was obtained in 80% yield. $^1$H NMR (CDCl$_3$, 400 MHz) δ7.17 (s, 1H), 6.95 (s, 2H), 6.90 (s, 1H), 6.86 (s, 1H), 3.96 (s, 3H), 3.90 (s, 3H), 3.48 (s, 2H), 3.30-3.36 (m, 1H), 2.80-2.91 (m, 4H), 2.39-2.45 (m, 3H), 3.33 (s, 6H), 1.91-2.02 (m, 1H), 1.75-1.90 (m, 3H), 1.62-1.65 (m, 1H); LRMS (EI) m/z 425 (M$^+$).

Example 4

Preparation of 2-((4-fluoro-1-(4-fluorobenzyl)piperidin-4-yl)methyl)-5,6-dimethoxy-2,3-dihydro-1H-inden-1-one (DC5)

4-nitrobenzyl bromide was replaced by 4-fluorobenzyl bromide and the rest of raw materials, reagents and the preparation were identical with those in example 1. DC5 was obtained in 80% yield. $^1$H NMR (CDCl$_3$, 400 MHz) δ 7.29 (t, 2H), 7.17 (s, 1H), 7.00 (t, 2H), 6.86 (s, 1H), 3.96 (s, 3H), 3.90 (s, 3H), 3.50 (s, 2H), 3.30-3.36 (m, 1H), 2.80-2.91 (m, 4H), 2.30-2.39 (m, 3H), 1.82-1.84 (m, 1H), 1.62-1.80 (m, 4H); LRMS (EI) m/z 415 (M$^+$).

Example 5

Preparation of 2-((4-fluoro-1-(4-(trifluoromethoxy)benzyl)piperidin-4-yl)methyl)-5,6-dimethoxy-2,3-dihydro-1H-inden-1-one (DC6)

4-nitrobenzyl bromide was replaced by 4-trifluoromethoxybenzyl bromide and the rest of raw materials, reagents and the preparation were identical with those in example 1. DC6 was obtained in 80% yield. $^1$H NMR (CDCl$_3$, 400 MHz) δ 7.36 (d, J=8.4, 2H), 7.25 (d, J=8.40, 2H), 7.17 (s, 1H), 6.86 (s, 1H), 3.96 (s, 3H), 3.91 (s, 3H), 3.53 (s, 2H), 3.28-3.34 (m, 1H), 2.80-2.92 (m, 4H), 2.32-2.40 (m, 3H), 1.91-2.02 (m, 1H), 1.75-1.90 (m, 2H), 1.63-1.65 (m, 2H); LRMS (EI) m/z 481 (M$^+$).

Example 6

Preparation of 2-((1-(4-(tert-butyl)benzyl)-4-fluoropiperidin-4-yl)methyl)-5,6-dimethoxy-2,3-dihydro-1H-inden-1-one (DC7)

4-nitrobenzyl bromide was replaced by 4-tert-butylbenzyl bromide and the rest of raw materials, reagents and the preparation were identical with those in example 1. DC7 was obtained in 80% yield. $^1$H NMR (CDCl$_3$, 400 MHz) δ 7.35 (d, J=8.0, 2H), 7.25 (d, J=8.40, 2H), 7.17 (s, 1H), 6.86 (s, 1H), 3.96 (s, 3H), 3.91 (s, 3H), 3.55 (s, 2H), 3.30-3.36 (m, 1H), 2.80-2.92 (m, 4H), 2.39-2.45 (m, 3H), 1.91-2.02 (m, 1H), 1.75-1.90 (m, 2H), 1.62-1.65 (m, 2H); LRMS (EI) m/z 453 (M$^+$).

Example 7

Preparation of 2-((4-fluoro-1-(2-fluoro-6-nitrobenzyl)piperidin-4-yl)methyl)-5,6-dimethoxy-2,3-dihydro-1H-inden-1-one (DC8)

4-nitrobenzyl bromide was replaced by 2-fluoro-6-nitrobenzyl bromide and the rest of raw materials, reagents and the preparation were identical with those in example 1. DC8 was obtained in 80% yield. $^1$H NMR (CDCl$_3$, 400 MHz) δ 7.51 (m, 1H), 7.38 (m, 1H), 7.29 (m, 1H); 7.17 (s, 1H), 6.86 (s, 1H), 3.96 (s, 3H), 3.89 (s, 3H), 3.85 (s, 2H), 3.27-3.36 (m, 1H), 2.75-2.87 (m, 4H), 2.39-2.41 (m, 3H), 1.91-2.02 (m, 1H), 1.55-1.63 (m, 4H); LRMS (EI) m/z 460 (M$^+$).

Example 8

Preparation of 2-((1-((6-bromobenzo[d][1,3]dioxol-5-yl)methyl)-4-fluoropiperidin-4-yl)methyl)-5,6-dimethoxy-2,3-dihydro-1H-inden-1-one (DC9)

4-nitrobenzyl bromide was replaced by 6-bromo-3,4-methyldioxobenzyl bromide and the rest of raw materials, reagents and the preparation were identical with those in example 1. DC9 was obtained in 80% yield. $^1$H NMR (CDCl$_3$, 400 MHz) δ 7.17 (s, 1H), 7.00 (m, 1H), 6.98 (s, 1H), 6.86 (s, 1H), 5.97 (s, 2H), 3.96 (s, 3H), 3.90 (s, 3H), 3.57 (s, 2H), 3.28-3.34 (m, 1H), 2.82-2.91 (m, 4H), 2.39-2.45 (m, 3H), 1.91-2.02 (m, 1H), 1.75-1.90 (m, 2H), 1.62-1.65 (m, 2H); LRMS (EI) m/z 520 (M$^+$).

Example 9

Preparation of 2-((1-(2,4-difluorobenzyl)-4-fluoropiperidin-4-yl)methyl)-5,6-dimethoxy-2,3-dihydro-1H-inden-1-one (DC10)

4-nitrobenzyl bromide was replaced by 6-bromo-3,4-methyldioxobenzyl bromide and the rest of raw materials, reagents and the preparation were identical with those in example 1. DC10 was obtained in 80% yield. $^1$H NMR (CDCl$_3$, 400 MHz) δ 7.28 (s, 1H), 7.17 (s, 1H), 6.86 (s, 1H), 6.79 (m, 2H), 3.96 (s, 3H), 3.91 (s, 3H), 3.65 (s, 2H), 3.29-3.36 (m, 1H), 2.74-2.90 (m, 4H), 2.39-2.42 (m, 3H), 1.91-2.02 (m, 1H), 1.75-1.90 (m, 2H), 1.61-1.65 (m, 2H); LRMS (EI) m/z 433 (M$^+$).

Example 10

Preparation of 2-((1-(3-bromobenzyl)-4-fluoropiperidin-4-yl)methyl)-5,6-dimethoxy-2,3-dihydro-1H-inden-1-one (DC11)

4-nitrobenzyl bromide was replaced by 3-bromobenzyl bromide and the rest of raw materials, reagents and the preparation were identical with those in example 1. DC11 as target product was obtained in 80% yield. $^1$H NMR (CDCl$_3$, 400 MHz) δ 7.50 (s, 1H), 7.39 (d, 1H), 7.28 (m, 1H); 7.17 (m, 2H), 6.86 (s, 1H), 3.97 (s, 3H), 3.90 (s, 3H), 3.52 (s, 2H), 3.30-3.36 (m, 1H), 2.80-2.90 (m, 4H), 2.33-2.40 (m, 3H), 1.90-2.00 (m, 1H), 1.75-1.90 (m, 2H), 1.62-1.65 (m, 2H); LRMS (EI) m/z 476 (M$^+$).

Example 11

Preparation of 2-((4-fluoro-1-(2,3,4-trifluorobenzyl)piperidin-4-yl)methyl)-5,6-dimethoxy-2,3-dihydro-1H-inden-1-one (DC12)

4-nitrobenzyl bromide was replaced by 2,3,4-trifluorobenzyl bromide and the rest of raw materials, reagents and the preparation were identical with those in example 1. DC12 as target product was obtained in 80% yield. $^1$H NMR (CDCl$_3$, 400 MHz) δ 7.17 (s, 1H), 7.15 (m, 1H), 6.95 (m, 1H), 6.86 (s, 1H), 3.96 (s, 3H), 3.90 (s, 3H), 3.60 (s, 2H), 3.29-3.35 (m, 1H), 2.80-2.92 (m, 4H), 2.39-2.42 (m, 3H), 1.89-2.01 (m, 2H), 1.62-1.85 (m, 3H); LRMS (EI) m/z 451 (M$^+$).

Example 12

Preparation of 3-((4-((5,6-dimethoxy-1-oxo-2,3-dihydro-1H-inden-2-yl)methyl)-4-fluoropiperidin-1-yl)methyl)benzonitrile (DC13)

4-nitrobenzyl bromide was replaced by 3-cyanobenzyl bromide and the rest of raw materials, reagents and the preparation were identical with those in example 1. DC13 as target product was obtained in 80% yield. $^1$H NMR (CDCl$_3$, 400 MHz) δ 7.66 (s, 1H), 7.56 (m, 2H), 7.44 (m, 1H), 7.17 (s, 1H), 6.86 (s, 1H), 3.98 (s, 3H), 3.96 (s, 3H), 3.58 (s, 2H), 3.29-3.38 (m, 1H), 2.83-2.90 (m, 4H), 2.39-2.45 (m, 3H), 1.65-1.99 (m, 2H), 1.59-1.65 (m, 3H); LRMS (EI) m/z 422 (M$^+$).

Example 13

Preparation of 2-((1-(2-bromobenzyl)-4-fluoropiperidin-4-yl)methyl)-5,6-dimethoxy-2,3-dihydro-1H-inden-1-one (DC14)

4-nitrobenzyl bromide was replaced by 2-bromobenzyl bromide and the rest of raw materials, reagents and the preparation were identical with those in example 1. DC14 as target product was obtained in 80% yield. $^1$H NMR (CDCl$_3$, 400 MHz) δ 7.56 (m, 2H), 7.28 (m, 1H), 7.17 (s, 1H), 7.12 (m, 1H), 6.86 (s, 1H), 3.96 (s, 3H), 3.90 (s, 3H), 3.65 (s, 2H), 3.31-3.37 (m, 1H), 2.79-2.92 (m, 4H), 2.39-2.45 (m, 3H), 1.91-2.02 (m, 1H), 1.75-1.90 (m, 2H), 1.60-1.67 (m, 2H); LRMS (EI) m/z 476 (M$^+$).

Example 14

Preparation of 2-((1-(4-bromo-2-fluorobenzyl)-4-fluoropiperidin-4-yl)methyl)-5,6-dimethoxy-2,3-dihydro-1H-inden-1-one (DC15)

4-nitrobenzyl bromide was replaced by 2-fluoro-4-bromobenzyl bromide and the rest of raw materials, reagents and the preparation were identical with those in example 1. DC15 as target product was obtained in 80% yield. $^1$H NMR (CDCl$_3$, 300 MHz) δ 7.27 (m, 2H), 7.25 (m, 1H), 7.17 (s, 1H), 6.86 (s, 1H), 3.96 (s, 3H), 3.91 (s, 3H), 3.56 (s, 2H), 3.28-3.37 (m, 1H), 2.79-2.92 (m, 4H), 2.30-2.41 (m, 3H), 1.91-2.02 (m, 1H), 1.76-1.90 (m, 2H), 1.61-1.67 (m, 2H); LRMS (EI) m/z 494 (M$^+$).

Example 15

Preparation of 2-((4-fluoro-1-(4-(trifluoromethyl)benzyl)piperidin-4-yl)methyl)-5,6-dimethoxy-2,3-dihydro-1H-inden-1-one (DC16)

4-nitrobenzyl bromide was replaced by 4-trifluoromethylbenzyl bromide and the rest of raw materials, reagents and the preparation were identical with those in example 1. DC16 as target product was obtained in 80% yield. $^1$H NMR (CDCl$_3$, 300 MHz) δ 7.57 (d, J=8.1, 2H), 7.45 (d, J=8.1, 2H), 7.17 (s, 1H), 6.86 (s, 1H), 3.96 (s, 3H), 3.91 (s, 3H), 3.59 (s, 2H), 3.29-3.37 (m, 1H), 2.69-2.92 (m, 4H), 2.31-2.41 (m, 3H), 1.91-2.01 (m, 1H), 1.76-1.90 (m, 2H), 1.61-1.67 (m, 2H); LRMS (EI) m/z 465 (M$^+$).

Example 16

Preparation of 2-((4-fluoro-1-(2,4,5-trifluorobenzyl)piperidin-4-yl)methyl)-5,6-dimethoxy-2,3-dihydro-1H-inden-1-one (DC17)

4-nitrobenzyl bromide was replaced by 2,4,5-trifluorobenzyl bromide and the rest of raw materials, reagents and the preparation were identical with those in example 1. DC17 as target product was obtained in 80% yield. $^1$H NMR (CDCl$_3$, 300 MHz) δ 7.27 (m, 1H), 7.17 (s, 1H), 6.91 (m, 1H), 6.86 (s, 1H), 3.96 (s, 3H), 3.90 (s, 3H), 3.54 (s, 2H), 3.29-3.54 (m, 1H), 2.66-2.92 (m, 4H), 2.40-2.45 (m, 3H), 1.91-2.02 (m, 1H), 1.76-1.90 (m, 2H), 1.62-1.67 (m, 2H); LRMS (EI) m/z 451 (M$^+$).

Example 17

Preparation of 2-((4-fluoro-1-(2-(trifluoromethyl)benzyl)piperidin-4-yl)methyl)-5,6-dimethoxy-2,3-dihydro-1H-inden-1-one (DC18)

4-nitrobenzyl bromide was replaced by 2-trifluoromethylbenzyl bromide and the rest of raw materials, reagents and the preparation were identical with those in example 1. DC18 as target product was obtained in 80% yield. $^1$H NMR (CDCl$_3$, 400 MHz) δ 7.79 (d, 2H), 7.62 (d, 2H), 7.51 (t, 1H), 7.32 (t, 1H), 7.17 (s, 1H), 6.86 (s, 1H), 3.96 (s, 3H), 3.91 (s, 3H), 3.69 (s, 2H), 3.31-3.37 (m, 1H), 2.82-2.92 (m, 4H), 2.39-2.45 (m, 3H), 1.91-2.02 (m, 1H), 1.76-1.90 (m, 2H), 1.60-1.67 (m, 2H); LRMS (EI) m/z 465 (M$^+$).

Example 18

Preparation of 2-((l-benzyl-4-fluoropiperidin-4-yl)methyl)-5,6-dimethoxy-2,3-dihydro-1H-inden-1-one (DC19)

4-nitrobenzyl bromide was replaced by 1-benzyl bromide and the rest of raw materials, reagents and the preparation were identical with those in example 1. DC19 as target product was obtained in 80% yield. $^1$H NMR (CDCl$_3$, 400 MHz) δ 7.31-7.33 (m, 5H), 7.17 (s, 1H), 6.86 (s, 1H), 3.96 (s, 3H), 3.90 (s, 3H), 3.59 (s, 2H), 3.29-3.37 (m, 1H), 2.79-2.92 (m, 4H), 2.30-2.41 (m, 3H), 1.91-2.02 (m, 1H), 1.66-2.02 (m, 4H); LRMS (EI) m/z 397 (M$^+$).

Example 19

Preparation of 2-((4-fluoro-1-(2-fluorobenzyl)piperidin-4-yl)methyl)-5,6-dimethoxy-2,3-dihydro-1H-inden-1-one (DC20)

4-nitrobenzyl bromide was replaced by 2-fluorobenzyl bromide and the rest of raw materials, reagents and the preparation were identical with those in example 1. DC20 as target product was obtained in 80% yield. $^1$H NMR (CDCl$_3$, 400 MHz) δ 7.41 (t, 1H), 7.24-7.26 (m, 1H), 7.17 (s, 1H), 7.12 (t, 1H), 7.06 (t, 1H), 6.86 (s, 1H), 3.98 (s, 3H), 3.90 (s, 3H), 3.65 (s, 2H), 3.29-3.34 (m, 1H), 2.80-2.90 (m, 4H), 2.39-2.45 (m, 3H), 1.91-2.02 (m, 1H), 1.75-1.90 (m, 2H), 1.62-1.65 (m, 2H); LRMS (EI) m/z 415 (M$^+$).

Example 20

Preparation of 2-((4-fluoro-1-(3-fluorobenzyl)piperidin-4-yl)methyl)-5,6-dimethoxy-2,3-dihydro-1H-inden-1-one (DC21)

4-nitrobenzyl bromide was replaced by 3-fluorobenzyl bromide and the rest of raw materials, reagents and the preparation were identical with those in example 1. DC21 as target product was obtained in 80% yield. $^1$H NMR (CDCl$_3$, 400 MHz) δ 7.26-7.28 (m, 1H), 7.17 (s, 1H), 7.07 (t, 2H), 6.63 (t, 1H), 6.86 (s, 1H), 3.98 (s, 3H), 3.90 (s, 3H), 3.54 (s, 2H), 3.30-3.36 (m, 1H), 2.80-2.90 (m, 2H), 2.70 (t, 2H), 2.39-2.45 (m, 3H), 1.91-2.02 (m, 1H), 1.75-1.90 (m, 2H), 1.62-1.65 (m, 2H); LRMS (EI) m/z 415 (M$^+$).

Example 21

Preparation of 2-((1-(3,5-bis(trifluoromethyl)benzyl)-4-fluoropiperidin-4-yl)methyl)-5,6-dimethoxy-2,3-dihydro-1H-inden-1-one (DC22)

4-nitrobenzyl bromide was replaced by 3,5-bistrifluoromethylbenzyl bromide and the rest of raw materials, reagents and the preparation were identical with those in example 1. DC22 as target product was obtained in 80% yield. $^1$H NMR (CDCl$_3$, 400 MHz) δ 7.79 (m, 3H), 7.17 (s, 1H), 6.86 (s, 1H), 3.96 (s, 3H), 3.90 (s, 3H), 3.64 (s, 2H), 3.30-3.36 (m, 1H), 2.80-2.90 (m, 2H), 2.68 (t, 2H), 2.39-2.45 (m, 3H), 1.91-2.02 (m, 1H), 1.75-1.90 (m, 2H), 1.62-1.65 (m, 2H); LRMS (EI) m/z 533 (M$^+$).

Example 22

Preparation of 2-((1-(3,5-difluorobenzyl)-4-fluoropiperidin-4-yl)methyl)-5,6-dimethoxy-2,3-dihydro-1H-inden-1-one (DC27)

4-nitrobenzyl bromide was replaced by 3,5-difluorobenzyl bromide and the rest of raw materials, reagents and the preparation were identical with those in example 1. DC27 as target product was obtained in 80% yield. $^1$H NMR (CDCl$_3$, 400 MHz) δ7.17 (s, 1H), 6.91 (s, 2H), 6.86 (s, 1H), 6.70 (t, 1H), 3.96 (s, 3H), 3.90 (s, 3H), 3.64 (s, 2H), 3.30-3.36 (m, 1H), 2.80-2.90 (m, 2H), 2.68 (t, 2H), 2.40-2.45 (m, 3H), 1.90-2.01 (m, 1H), 1.75-1.90 (m, 2H), 1.62-1.65 (m, 2H); LRMS (EI) m/z 433 (M$^+$).

Example 23

Preparation of 2-((4-fluoro-1-((perfluorophenyl)methyl)piperidin-4-yl)methyl)-5,6-dimethoxy-2,3-dihydro-1H-inden-1-one (DC28)

4-nitrobenzyl bromide was replaced by 2,3,4,5,6-pentafluorobenzyl bromide and the rest of raw materials, reagents and the preparation were identical with those in example 1. DC28 as target product was obtained in 80% yield. $^1$H NMR (CDCl$_3$, 400 MHz) δ7.16 (s, 1H), 6.85 (s, 1H), 3.96 (s, 3H), 3.90 (s, 3H), 3.76 (s, 2H), 3.30-3.38 (m, 1H), 2.64-2.88 (m, 4H), 2.39-2.44 (m, 3H), 1.93-2.04 (m, 1H), 1.75-1.84 (m, 2H), 1.60-1.64 (m, 2H); LRMS (EI) m/z 487 (M$^+$).

Example 24

Preparation of 2-((4-fluoro-1-(3-methylbenzyl)piperidin-4-yl)methyl)-5,6-dimethoxy-2,3-dihydro-1H-inden-1-one (DC29)

4-nitrobenzyl bromide was replaced by 3-methylbenzyl bromide and the rest of raw materials, reagents and the preparation were identical with those in example 1. DC29 as target product was obtained in 80% yield. $^1$H NMR (CDCl$_3$, 400 MHz) δ 7.19-7.24 (m, 3H), 7.17 (s, 1H), 7.12 (m, 1H), 6.86 (s, 1H), 3.96 (s, 3H), 3.90 (s, 3H), 3.66 (s, 2H), 3.31-3.37 (m, 1H), 2.78-2.88 (m, 4H), 2.35-2.51 (m, 3H), 2.36 (s, 3H), 1.85-2.01 (m, 3H), 1.53-1.74 (m, 2H); LRMS (EI) m/z 411 (M$^+$).

Example 25

Preparation of 2-((4-fluoro-1-(3-(trifluoromethyl)benzyl)piperidin-4-yl)methyl)-5,6-dimethoxy-2,3-dihydro-1H-inden-1-one (DC30)

4-nitrobenzyl bromide was replaced by 3-trifluoromethylbenzyl bromide and the rest of raw materials, reagents and the preparation were identical with those in example 1. DC30 as target product was obtained in 80% yield. $^1$H NMR (CDCl$_3$, 400 MHz) δ 7.61 (s, 1H), 7.52 (m, 2H), 7.49 (m, 1H), 7.17 (s, 1H), 6.86 (s, 1H), 3.96 (s, 3H), 3.90 (s, 3H), 3.60 (s, 2H), 3.30-3.36 (m, 1H), 2.80-2.91 (m, 4H) 2.38-2.41 (m, 3H), 1.90-2.01 (m, 1H), 1.75-1.90 (m, 2H), 1.62-1.65 (m, 2H); LRMS (EI) m/z 465 (M$^+$).

Example 26

Preparation of 2-((1-(cyclobutylmethyl)-4-fluoropiperidin-4-yl)methyl)-5,6-dimethoxy-2,3-dihydro-1H-inden-1-one (DC31)

4-nitrobenzyl bromide was replaced by cyclobutylmethyl bromide and the rest of raw materials, reagents and the preparation were identical with those in example 1. DC31 as target product was obtained in 80% yield. $^1$H NMR (CDCl$_3$, 400 MHz) δ7.17 (s, 1H), 6.86 (s, 1H), 3.96 (s, 3H), 3.90 (s, 3H), 3.36-3.43 (m, 4H), 2.76-2.86 (m, 4H), 2.48-2.53 (m, 3H), 2.42-2.48 (m, 1H), 2.28-2.31 (m, 3H), 1.93-2.02 (m, 1H), 1.75-1.90 (m, 2H), 1.62-1.65 (s, 2H); LRMS (EI) m/z 375 (M$^+$).

Example 27

Preparation of 2-((1-(cyclopentylmethyl)-4-fluoropiperidin-4-yl)methyl)-5,6-dimethoxy-2,3-dihydro-1H-inden-1-one (DC32)

4-nitrobenzyl bromide was replaced by cyclopentylmethyl bromide and the rest of raw materials, reagents and the preparation were identical with those in example 1. DC32 as target product was obtained in 80% yield. $^1$H NMR (CDCl$_3$, 400 MHz) δ 7.16 (s, 1H), 6.87 (s, 1H), 3.96 (s, 3H), 3.90 (s, 3H), 3.36-3.46 (m, 3H), 2.16-2.26 (m, 1H), 3.03 (t, 2H), 2.76-2.85 (m, 2H), 2.52-2.61 (m, 1H), 2.21-2.47 (m, 2H), 1.02-2.18 (m, 5H), 1.89 (s, 5H), 1.65-1.71 (s, 3H); LRMS (EI) m/z 389 (M$^+$).

Example 28

Preparation of 2-((1-(cyclohexylmethyl)-4-fluoropiperidin-4-yl)methyl)-5,6-dimethoxy-2,3-dihydro-1H-inden-1-one (DC33)

4-nitrobenzyl bromide was replaced by cyclohexylmethyl bromide and the rest of raw materials, reagents and the preparation were identical with those in example 1. DC33 as target product was obtained in 80% yield. $^1$H NMR (CDCl$_3$, 400 MHz) δ 7.17 (s, 1H), 6.87 (s, 1H), 3.97 (s, 3H), 3.91 (s, 3H), 3.36-3.66 (m, 4H), 2.70-2.96 (m, 2H), 2.46-2.55 (m, 1H), 2.02-2.21 (m, 4H), 1.61-1.97 (m, 11H), 1.22-1.28 (m, 3H); LRMS (EI) m/z 403 (M$^+$).

Example 29

Preparation of 2-((1-(cycloheptylmethyl)-4-fluoropiperidin-4-yl)methyl)-5,6-dimethoxy-2,3-dihydro-1H-inden-1-one (DC34)

4-nitrobenzyl bromide was replaced by cycloheptylmethyl bromide and the rest of raw materials, reagents and the preparation were identical with those in example 1. DC34 as target product was obtained in 80% yield. $^1$H NMR (CDCl$_3$, 400 MHz) δ 7.16 (s, 1H), 6.88 (s, 1H), 3.96 (s, 3H), 3.90 (s, 3H), 3.36-3.40 (m, 1H), 3.16-2.28 (m, 5H), 2.76-2.85 (m, 2H), 2.49-2.56 (m, 4H), 2.12-2.17 (m, 4H), 1.80-2.82 (m, 2H), 1.53-1.71 (m, 10H); LRMS (EI) m/z 417 (M$^+$).

Example 30

Preparation of 2-((4-fluoro-1-(2,3,5-trifluorobenzyl)piperidin-4-yl)methyl)-5,6-dimethoxy-2,3-dihydro-1H-inden-1-one (DC35)

4-nitrobenzyl bromide was replaced by 2,3,5-trifluoromethylbenzyl bromide and the rest of raw materials, reagents and the preparation were identical with those in example 1. DC35 as target product was obtained in 80% yield. $^1$H NMR (CDCl$_3$, 400 MHz) δ 7.17 (s, 1H), 7.02 (s, 1H), 6.87 (s, 1H), 6.86 (s, 1H), 3.96 (s, 3H), 3.90 (s, 3H), 3.64 (s, 2H), 3.30-3.37 (m, 1H), 2.79-2.91 (m, 4H) 2.38-2.41 (m, 3H), 1.90-2.01 (m, 1H), 1.75-1.90 (m, 2H), 1.60-1.65 (m, 2H); LRMS (EI) m/z 451 (M$^+$).

Example 31

Preparation of 2-((1-([1,1'-biphenyl]-4-ylmethyl)-4-fluoropiperidin-4-yl)methyl)-5,6-dimethoxy-2,3-dihydro-1H-inden-1-one (DC36)

4-nitrobenzyl bromide was replaced by biphenyl-4-methyl bromide and the rest of raw materials, reagents and the preparation were identical with those in example 1. DC36 as target product was obtained in 80% yield. $^1$H NMR (CDCl$_3$, 400 MHz) 7.55-7.60 (m, 4H), 7.42-7.46 (m, 4H), 7.34-7.36 (m, 1H), 7.17 (s, 1H), 6.86 (s, 1H), 3.96 (s, 3H), 3.90 (s, 3H), 3.64 (s, 2H), 3.30-3.36 (m, 1H), 2.80-2.90 (m, 4H), 2.39-2.45 (m, 3H), 1.93-2.02 (m, 1H), 1.75-1.90 (m, 2H), 1.62-1.65 (m, 2H); LRMS (EI) m/z 473 (M$^+$).

Example 32

Preparation of 2-((3-fluoro-8-(4-nitrobenzyl)-8-azabicyclo[3.2.1]octan-3-yl)methyl)-5,6-dimethoxy-2,3-dihydro-1H-inden-1-one (DC41)

4-Boc-piperidone was replaced by 4-Boc-tropinone and the rest of raw materials, reagents and the preparation were identical with those in example 1. DC41 as target product was obtained in 80% yield. $^1$H NMR (CDCl$_3$, 400 MHz) 8.18 (d, J=8.4, 2H), 7.60 (d, J=8.4, 2H), 7.17 (s, 1H), 6.86 (s, 1H), 3.96 (s, 3H), 3.91 (s, 3H), 3.76 (s, 2H), 3.31-3.36 (m, 1H), 3.22 (s, 2H), 2.85-2.92 (m, 2H), 2.50-2.71 (m, 1H), 2.28-2.48 (m, 1H), 2.19-2.30 (m, 1H), 2.07-2.13 (m, 3H), 1.71-1.82 (m, 4H); LRMS (EI) m/z 468 (M$^+$).

Example 33

Preparation of 2-((3-((5,6-dimethoxy-1-oxo-2,3-dihydro-1H-inden-2-yl)methyl)-3-fluoro-8-azabicyclo[3.2.1]octan-8-yl)methyl)benzonitrile (DC43)

4-nitrobenzyl bromide was replaced by 2-cyanobenzyl bromide and the rest of raw materials, reagents and the preparation were identical with those in example 32. DC43 as target product was obtained in 80% yield. $^1$H NMR (CDCl$_3$, 400 MHz) (57.73 (s, 1H), 7.58-7.65 (m, 2H), 7.35 (m, 1H), 7.17 (s, 1H), 6.86 (s, 1H), 3.96 (s, 3H), 3.91 (s, 3H), 3.83 (s, 2H), 3.26-3.34 (m, 3H), 2.85-2.92 (m, 2H), 2.50-2.71 (m, 1H), 2.28-2.48 (m, 1H), 2.19-2.30 (m, 1H), 2.07-2.13 (m, 3H), 1.71-1.82 (m, 4H); LRMS (EI) m/z 448 (M$^+$).

Example 34

Preparation of 2-((8-(3,5-dimethylbenzyl)-3-fluoro-8-azabicyclo[3.2.1]octan-3-yl)methyl)-5,6-dimethoxy-2,3-dihydro-1H-inden-1-one (DC44)

4-nitrobenzyl bromide was replaced by 3,5-dimethylbenzyl bromide and the rest of raw materials, reagents and the preparation were identical with those in example 32. DC44 as target product was obtained in 80% yield. $^1$H NMR (CDCl$_3$, 400 MHz) δ7.17 (s, 1H), 7.05 (s, 2H), 6.91 (t, 2H), 6.86 (s, 1H), 3.96 (s, 3H), 3.91 (s, 3H), 3.64 (s, 2H), 3.29-3.36 (m, 3H), 2.86-2.93 (m, 2H), 2.50-2.71 (m, 1H), 2.32 (s, 6H), 2.28-2.48 (m, 1H), 2.19-2.30 (m, 1H), 2.05-2.13 (m, 3H), 1.72-1.82 (m, 4H); LRMS (EI) m/z 451 (M$^+$).

Example 35

Preparation of 2-((3-fluoro-8-(4-fluorobenzyl)-8-azabicyclo[3.2.1]octan-3-yl)methyl)-5,6-dimethoxy-2,3-dihydro-1H-inden-1-one (DC45)

4-nitrobenzyl bromide was replaced by 4-fluorobenzyl bromide and the rest of raw materials, reagents and the preparation were identical with those in example 32. DC45 as target product was obtained in 80% yield. $^1$H NMR (CDCl$_3$, 400 MHz) δ 7.39 (m, 2H), 7.17 (s, 1H), 7.01 (t, 2H), 6.86 (s, 1H), 3.96 (s, 3H), 3.91 (s, 3H), 3.65 (s, 2H), 3.31-3.36 (m, 1H), 3.26 (s, 2H), 2.85-2.93 (m, 2H), 2.50-2.71 (m, 1H), 2.28-2.48 (m, 1H), 2.19-2.30 (m, 1H), 2.05-2.13 (m, 3H), 1.72-1.82 (m, 4H); LRMS (EI) m/z 441 (M$^+$).

Example 36

Preparation of 2-((8-(4-(tert-butyl)benzyl)-3-fluoro-8-azabicyclo[3.2.1]octan-3-yl)methyl)-5,6-dimethoxy-2,3-dihydro-1H-inden-1-one (DC47)

4-nitrobenzyl bromide was replaced by 4-tert-butylbenzyl bromide and the rest of raw materials, reagents and the preparation were identical with those in example 32. DC47 as target product was obtained in 80% yield. $^1$H NMR (CDCl$_3$, 400 MHz) δ 7.36 (s, 4H), 7.17 (s, 1H), 6.86 (s, 1H), 3.96 (s, 3H), 3.91 (s, 3H), 3.68 (s, 2H), 3.30-3.36 (m, 3H), 2.86-2.93 (m, 2H), 2.50-2.71 (m, 1H), 2.28-2.48 (m, 1H), 2.19-2.30 (m, 1H), 2.07-2.13 (m, 3H), 1.71-1.82 (m, 4H), 1.31 (s, 9H); LRMS (EI) m/z 479 (M$^+$).

Example 37

Preparation of 2-((3-fluoro-8-(2-fluoro-6-nitrobenzyl)-8-azabicyclo[3.2.1]octan-3-yl)methyl)-5,6-dimethoxy-2,3-dihydro-1H-inden-1-one (DC48)

4-nitrobenzyl bromide was replaced by 2-fluoro-6-nitrobenzyl bromide and the rest of raw materials, reagents and the preparation were identical with those in example 32. DC48 as target product was obtained in 80% yield. $^1$H NMR (CDCl$_3$, 400 MHz) δ 7.53 (m, 1H), 7.38 (m, 1H), 7.25 (m, 1H), 7.17 (s, 1H), 6.86 (s, 1H), 3.96 (s, 5H), 3.12-3.14 (m, 1H), 3.11 (s, 2H), 2.86-2.93 (m, 2H), 2.50-2.71 (m, 1H), 2.28-2.48 (m, 1H), 1.96-2.13 (m, 4H), 1.71-1.82 (m, 4H); LRMS (EI) m/z 486 (M$^+$).

Example 38

Preparation of methyl 4-((3-((5,6-dimethoxy-1-oxo-2,3-dihydro-1H-inden-2-yl)methyl)-3-fluoro-8-azabicyclo[3.2.1]octan-8-yl)methyl)benzoate (DC50)

4-nitrobenzyl bromide was replaced by 4-methoxycarbonylbenzyl bromide and the rest of raw materials, reagents and the preparation were identical with those in example 32. DC50 as target product was obtained in 80% yield. $^1$H NMR (CDCl$_3$, 400 MHz) δ 8.00 (d, J=8.0, 2H), 7.53 (d, J=8.4, 2H), 7.17 (s, 1H), 6.86 (s, 1H), 3.96 (s, 3H), 3.91 (s, 6H), 3.74 (s, 2H), 3.32-3.41 (m, 3H), 2.85-2.92 (m, 2H), 2.52-2.71 (m, 1H), 2.28-2.48 (m, 1H), 2.19-2.30 (m, 1H), 2.07-2.14 (m, 3H), 1.70-1.82 (m, 4H); LRMS (EI) m/z 481 (M$^+$).

Example 39

Preparation of 2-((8-(3-bromobenzyl)-3-fluoro-8-azabicyclo[3.2.1]octan-3-yl)methyl)-5,6-dimethoxy-2,3-dihydro-1H-inden-1-one (DC51)

4-nitrobenzyl bromide was replaced by 3-bromobenzyl bromide and the rest of raw materials, reagents and the preparation were identical with those in example 32. DC51 as target product was obtained in 80% yield. $^1$H NMR (CDCl$_3$, 400 MHz) δ 7.59 (s, 1H), 7.37 (m, 2H), 7.21 (m, 1H), 7.17 (s, 1H), 6.86 (s, 1H), 3.96 (s, 3H), 3.90 (s, 3H), 3.65 (s, 2H), 3.30-3.36 (m, 1H), 3.20 (s, 2H), 2.83-2.92 (m, 2H), 2.50-2.71 (m, 1H), 2.28-2.48 (m, 1H), 2.19-2.30 (m, 1H), 2.07-2.13 (m, 3H), 1.72-1.82 (m, 4H); LRMS (EI) m/z 476 (M$^+$).

Example 40

Preparation of 2-((3-fluoro-8-(2-nitrobenzyl)-8-azabicyclo[3.2.1]octan-3-yl)methyl)-5,6-dimethoxy-2,3-dihydro-1H-inden-1-one (DC52)

4-nitrobenzyl bromide was replaced by 2-nitrobenzyl bromide and the rest of raw materials, reagents and the preparation were identical with those in example 32. DC52 as target product was obtained in 80% yield. $^1$H NMR (CDCl$_3$, 400 MHz) δ 7.80-7.86 (m, 2H), 7.57 (t, 1H), 7.39 (t, 1H), 7.17 (s, 1H), 6.86 (s, 1H), 3.96 (s, 3H), 3.90 (s, 5H), 3.30-3.36 (m, 1H), 3.20 (s, 2H), 2.82-2.92 (m, 2H), 2.50-2.71 (m, 1H), 2.28-2.48 (m, 1H), 2.19-2.30 (m, 1H), 2.07-2.13 (m, 3H), 1.68-1.82 (m, 4H); LRMS (EI) m/z 468 (M$^+$).

Example 41

Preparation of 2-((8-(2-bromobenzyl)-3-fluoro-8-azabicyclo[3.2.1]octan-3-yl)methyl)-5,6-dimethoxy-2,3-dihydro-1H-inden-1-one (DC54)

4-nitrobenzyl bromide was replaced by 2-bromobenzyl bromide and the rest of raw materials, reagents and the preparation were identical with those in example 32. DC54 as target product was obtained in 80% yield. $^1$H NMR (CDCl$_3$, 400 MHz) δ 7.73 (s, 1H), 7.53 (d, 1H), 7.32 (t, 1H), 7.17 (s, 1H), 7.11 (t, 1H), 6.86 (s, 1H), 3.96 (s, 3H), 3.91 (s, 5H), 3.70 (s, 2H), 3.28-3.37 (m, 3H), 2.86-2.94 (m, 2H), 2.50-2.71 (m, 1H), 2.28-2.48 (m, 1H), 2.19-2.30 (m, 1H), 2.07-2.13 (m, 3H), 1.68-1.82 (m, 4H); LRMS (EI) m/z 476 (M$^+$).

Example 42

Preparation of 2-((3-fluoro-8-(2,4,5-trifluorobenzyl)-8-azabicyclo[3.2.1]octan-3-yl)methyl)-5,6-dimethoxy-2,3-dihydro-1H-inden-1-one (DC57)

4-nitrobenzyl bromide was replaced by 2,4,5-trifluorobenzyl bromide and the rest of raw materials, reagents and the preparation were identical with those in example 32. DC57 as target product was obtained in 80% yield. $^1$H NMR (CDCl$_3$, 400 MHz) δ 7.51 (s, 1H), 7.17 (s, 1H), 6.88 (m, 1H), 6.86 (s, 1H), 3.96 (s, 3H), 3.91 (s, 3H), 3.63 (s, 2H), 3.30-3.36 (m, 1H), 3.20 (s, 2H), 2.82-2.92 (m, 2H), 2.50-2.71 (m, 1H), 2.26-2.45 (m, 1H), 2.15-2.27 (m, 1H), 2.07-2.13 (m, 3H), 1.68-1.82 (m, 4H); LRMS (EI) m/z 451 (M$^+$).

Example 43

Preparation of 2-((8-benzyl-3-fluoro-8-azabicyclo[3.2.1]octan-3-yl)methyl)-5,6-dimethoxy-2,3-dihydro-1H-inden-1-one (DC59)

4-nitrobenzyl bromide was replaced by benzyl bromide and the rest of raw materials, reagents and the preparation were identical with those in example 32. DC59 as target product was obtained in 80% yield. $^1$H NMR (CDCl$_3$, 400 MHz) δ 7.44 (s, 2H), 7.33 (t, 2H), 7.25 (m, 1H), 7.17 (s, 1H), 6.86 (s, 1H), 3.96 (s, 3H), 3.91 (s, 3H), 3.70 (s, 2H), 3.28-3.33 (m, 3H), 2.87-2.92 (m, 2H), 2.50-2.71 (m, 1H), 2.15-2.47 (m, 2H), 2.03-2.13 (m, 3H), 1.68-1.82 (m, 4H); LRMS (EI) m/z 423 (M$^+$).

Example 44

Preparation of 2-((3-fluoro-8-(2-fluorobenzyl)-8-azabicyclo[3.2.1]octan-3-yl)methyl)-5,6-dimethoxy-2,3-dihydro-1H-inden-1-one (DC60)

4-nitrobenzyl bromide was replaced by 2-fluorobenzyl bromide and the rest of raw materials, reagents and the preparation were identical with those in example 32. DC60 as target product was obtained in 80% yield. $^1$H NMR (CDCl$_3$, 400 MHz) δ 7.64 (s, 1H), 7.23 (m, 1H), 7.15-7.18 (m, 2H), 6.99 (t, 1H), 6.86 (s, 1H), 3.96 (s, 3H), 3.91 (s, 3H), 3.71 (s, 2H), 3.31-3.35 (m, 3H), 2.85-2.93 (m, 2H), 2.52-2.71 (m, 1H), 2.15-2.47 (m, 2H), 2.03-2.13 (m, 3H), 1.72-1.88 (m, 4H); LRMS (EI) m/z 441 (M$^+$).

Example 45

Preparation of 2-((3-fluoro-8-(3-fluorobenzyl)-8-azabicyclo[3.2.1]octan-3-yl)methyl)-5,6-dimethoxy-2,3-dihydro-1H-inden-1-one (DC61)

4-nitrobenzyl bromide was replaced by 3-fluorobenzyl bromide and the rest of raw materials, reagents and the preparation were identical with those in example 32. DC61 as target product was obtained in 80% yield. $^1$H NMR (CDCl$_3$, 400 MHz) δ 7.28 (m, 1H), 7.17-7.24 (m, 3H), 6.96 (m, 1H), 6.86 (s, 1H), 3.96 (s, 3H), 3.91 (s, 3H), 3.67 (s, 2H), 3.25-3.37 (m, 3H), 2.83-2.93 (m, 2H), 2.53-2.71 (m, 1H), 2.28-2.48 (m, 1H), 2.10-2.26 (m, 1H), 2.07-2.13 (m, 3H), 1.71-1.86 (m, 4H); LRMS (EI) m/z 441 (M$^+$).

Example 46

Preparation of 2-((3-fluoro-8-((perfluorophenyl)methyl)-8-azabicyclo[3.2.1]octan-3-yl)methyl)-5,6-dimethoxy-2,3-dihydro-1H-inden-1-one (DC68)

4-nitrobenzyl bromide was replaced by 2,3,4,5,6-pentafluorobenzyl bromide and the rest of raw materials, reagents and the preparation were identical with those in example 32. DC68 as target product was obtained in 80% yield. $^1$H NMR (CDCl$_3$, 400 MHz) δ 7.17 (s, 1H), 6.86 (s, 1H), 3.96 (s, 3H), 3.91 (s, 3H), 3.71 (s, 2H), 3.32-3.36 (m, 3H), 2.84-2.91 (m, 2H), 2.54-2.71 (m, 1H), 2.09-2.26 (m, 4H), 1.71-1.86 (m, 4H); LRMS (EI) m/z 513 (M$^+$).

Example 47

Preparation of 2-((3-fluoro-8-(3-methylbenzyl)-8-azabicyclo[3.2.1]octan-3-yl)methyl)-5,6-dimethoxy-2,3-dihydro-1H-inden-1-one (DC69)

4-nitrobenzyl bromide was replaced by 3-methylbenzyl bromide and the rest of raw materials, reagents and the preparation were identical with those in example 32. DC69 as target product was obtained in 80% yield. $^1$H NMR (CDCl$_3$, 400 MHz) δ 7.17-7.26 (m, 3H), 7.17 (s, 1H), 7.10 (m, 1H), 6.87 (s, 1H), 3.96 (s, 3H), 3.91 (s, 3H), 3.67 (s, 2H), 3.28-3.33 (m, 3H), 2.88-2.94 (m, 2H), 2.52-2.71 (m, 1H), 2.18-2.48 (m, 1H), 2.36 (s, 3H), 2.18-2.35 (m, 1H), 2.07-2.13 (m, 3H), 1.71-1.79 (m, 4H); LRMS (EI) m/z 437 (M$^+$).

Example 48

Preparation of 2-((3-fluoro-8-(3-(trifluoromethyl)benzyl)-8-azabicyclo[3.2.1]octan-3-yl)methyl)-5,6-dimethoxy-2,3-dihydro-1H-inden-1-one (DC70)

4-nitrobenzyl bromide was replaced by 3-trifluoromethylbenzyl bromide and the rest of raw materials, reagents and the preparation were identical with those in example 32. DC70 as target product was obtained in 80% yield. $^1$H NMR (CDCl$_3$, 400 MHz) δ 7.68 (s, 1H), 7.61 (m, 1H), 7.49 (m, 1H), 7.44 (m, 1H), 7.17 (s, 1H), 6.87 (s, 1H), 3.96 (s, 3H), 3.91 (s, 3H), 3.73 (s, 2H), 3.31-3.33 (m, 1H), 3.25 (s, 2H), 2.86-2.93 (m, 2H), 2.52-2.71 (m, 1H), 2.18-2.48 (m, 1H), 2.18-2.35 (m, 1H), 2.07-2.13 (m, 3H), 1.71-1.79 (m, 4H); LRMS (EI) m/z 491 (M$^+$).

Example 49

Preparation of 2-((3-fluoro-8-(2,3,5-trifluorobenzyl)-8-azabicyclo[3.2.1]octan-3-yl)methyl)-5,6-dimethoxy-2,3-dihydro-1H-inden-1-one (DC75)

4-nitrobenzyl bromide was replaced by 2,3,5-trifluorobenzyl bromide and the rest of raw materials, reagents and the preparation were identical with those in example 32. DC75 as target product was obtained in 80% yield. $^1$H NMR (CDCl$_3$, 400 MHz) δ 7.28 (s, 1H), 7.17 (s, 1H), 6.95 (m, 1H), 6.86 (s, 1H), 3.96 (s, 3H), 3.91 (s, 3H), 3.66 (s, 2H), 3.25-3.37 (m, 1H), 3.25 (s, 2H), 2.53-2.68 (m, 2H), 2.50-2.71 (m, 1H), 2.28-2.48 (m, 1H), 2.19-2.30 (m, 1H), 2.07-2.13 (m, 3H), 1.71-1.86 (m, 4H); LRMS (EI) m/z 477 (M$^+$).

Example 50

Preparation of 2-((8-([1,1'-biphenyl]-4-ylmethyl)-3-fluoro-8-azabicyclo[3.2.1]octan-3-yl)methyl)-5,6-dimethoxy-2,3-dihydro-1H-inden-1-one (DC76)

4-nitrobenzyl bromide was replaced by biphenyl-4-methyl bromide and the rest of raw materials, reagents and the preparation were identical with those in example 32. DC76 as target product was obtained in 80% yield. $^1$H NMR (CDCl$_3$, 400 MHz) δ 7.52-7.61 (m, 4H), 7.52-7.56 (m, 2H), 7.44 (t, 2H), 7.34 (t, 2H), 7.17 (s, 1H), 6.86 (s, 1H), 3.96 (s, 3H), 3.91 (s, 3H), 3.76 (s, 2H), 3.32-3.37 (m, 3H), 2.88-2.98 (m, 2H), 2.50-2.71 (m, 1H), 2.28-2.48 (m, 1H), 2.19-2.30 (m, 1H), 2.07-2.13 (m, 3H), 1.71-1.86 (m, 4H); LRMS (EI) m/z 411 (M$^+$).

Example 51

Preparation of 2-((1-benzoyl-4-fluoropiperidin-4-yl)methyl)-5,6-dimethoxy-2,3-dihydro-1H-inden-1-one (DC23)

4-nitrobenzyl bromide was replaced by benzoyl chloride and the rest of raw materials, reagents and the preparation were identical with those in example 1 to obtain DC23 as target product. $^1$H NMR (CDCl$_3$, 400 MHz) δ 8.03 (m, 2H), 7.63-7.70 (m, 3H), 7.54 (s, 1H), 7.04 (s, 1H), 3.83 (s, 6H), 3.34-3.67 (m, 5H), 2.58-2.83 (m, 2H), 1.56-1.62 (m, 6H); LRMS (EI) m/z 499 (M$^+$).

Example 52

Preparation of 2-((4-((5,6-dimethoxy-1-oxo-2,3-dihydro-1H-inden-2-yl)methyl)-4-fluoropiperidin-1-yl)methyl)benzonitrile hydrochloride (DC37)

Compound DC3 was dissolved in small amount of dioxane and dioxane hydrochloric acid solution was added and stirred to precipitate white solids. After filtered by suction and dried, the product DC37 was obtained. $^1$H NMR (CDCl$_3$, 400 MHz) δ 7.65 (m, 1H), 7.55 (m, 2H), 7.36 (m, 1H), 7.17 (s, 1H), 6.86 (s, 1H), 3.98 (s, 3H), 3.89 (s, 3H), 3.65 (s, 2H), 3.28-3.34 (m, 1H), 2.67-2.91 (m, 4H), 2.39-2.51 (m, 3H), 1.91-2.02 (m, 1H), 1.62-2.03 (m, 4H); LRMS (EI) m/z 422 (M$^+$).

Example 53

Preparation of 2-((4-fluoro-1-(3-fluorobenzyl)piperidin-4-yl)methyl)-5,6-dimethoxy-2,3-dihydro-1H-inden-1-one hydrochloride (DC38)

Compound DC21 was dissolved in small amount of dioxane and dioxane hydrochloric acid solution was added and stirred to precipitate white solids. After filtered by suction and dried, the product DC38 was obtained. $^1$H NMR (CDCl$_3$, 400 MHz) δ 7.26-7.28 (m, 1H), 7.17 (s, 1H), 7.07 (t, 2H), 6.63 (t, 1H), 6.86 (s, 1H), 3.98 (s, 3H), 3.90 (s, 3H), 3.54 (s, 2H), 3.30-3.36 (m, 1H), 2.80-2.90 (m, 2H), 2.70 (t, 2H), 2.39-2.45 (m, 3H), 1.91-2.02 (m, 1H), 1.75-1.90 (m, 2H), 1.62-1.65 (m, 2H); LRMS (EI) m/z 415 (M$^+$).

Example 54

Preparation of 5,6-diethoxy-2-((4-fluoro-1-(2-fluorobenzyl)piperidin-4-yl)methyl)-2,3-dihydro-1H-inden-1-one (DC77)

4-nitrobenzyl bromide was replaced by 2-fluorobenzyl bromide, 5,6-dimethoxyindanone was replaced by 5,6-diethoxyindanone and the rest of raw materials, reagents and the preparation were identical with those in example 1 to obtain DC77 as target product. $^1$H NMR (CDCl$_3$, 400 MHz) 7.48-7.56 (m, 3H), 7.04-7.28 (m, 3H), 4.09 (m, 4H), 3.66 (s, 2H), 3.37 (m, 1H), 2.58 (m, 2H), 1.72-2.14 (m, 4H), 1.52-1.64 (m, 6H), 1.32 (m, 6H); LRMS (EI) m/z 443 (M$^+$).

Example 55

Preparation of 2-((4-fluoro-1-(2-fluorobenzyl)piperidin-4-yl)methyl)-5,6-dipropoxy-2,3-dihydro-1H-inden-1-one (DC78)

4-nitrobenzyl bromide was replaced by 2-fluorobenzyl bromide, 5,6-dimethoxyindanone was replaced by 5,6-dipropoxyindanone and the rest of raw materials, reagents and the preparation were identical with those in example 1 to obtain DC78 as target product. $^1$H NMR (CDCl$_3$, 400 MHz) 7.48-7.56 (m, 3H), 7.04-7.25 (m, 3H), 4.03 (m, 4H), 3.66 (s, 2H), 3.37 (m, 1H), 2.58 (m, 2H), 1.82-2.14 (m, 4H), 1.62-1.74 (m, 10H), 0.90 (m, 6H); LRMS (EI) m/z 471 (M$^+$).

Example 56

Preparation of 5,6-bis(ethoxymethoxy)-2-((4-fluoro-1-(2-fluorobenzyl)piperidin-4-yl)methyl)-2,3-dihydro-1H-inden-1-one (DC79)

4-nitrobenzyl bromide was replaced by 2-fluorobenzyl bromide, 5,6-dimethoxyindanone was replaced by 5,6-di (ethoxymethoxy)indanone and the rest of raw materials, reagents and the preparation were identical with those in example 1 to obtain DC79 as target product. $^1$H NMR (CDCl$_3$, 400 MHz) δ 7.48-7.56 (m, 3H), 7.04-7.21 (m, 3H), 6.03 (s, 4H), 3.66 (s, 2H), 3.37-3.50 (m, 5H), 2.58 (m, 2H), 1.62-2.14 (m, 4H), 1.62-1.74 (m, 4H), 1.10 (m, 6H); LRMS (EI) m/z 503 (M$^+$).

Example 80

Preparation of 2-((4-fluoro-1-(2-fluorobenzyl)piperidin-4-yl)methyl)-5,6-bis(2,2,2-trifluoroethoxy)-2,3-dihydro-1H-inden-1-one (DC103)

4-nitrobenzyl bromide was replaced by 2-fluorobenzyl bromide, 5,6-dimethoxyindanone was replaced by 5,6-di(trifluoroethoxy)indanone and the rest of raw materials, reagents and the preparation were identical with those in example 1 to obtain DC103 as target product. $^1$H NMR (CDCl$_3$, 400 MHz) δ 7.48-7.56 (m, 3H), 7.04-7.21 (m, 3H), 4.46 (m, 4H), 3.66 (s, 2H), 3.37 (m, 1H), 2.58-2.83 (m, 2H), 1.62-2.24 (m, 4H), 1.56-1.62 (m, 6H); LRMS (EI) m/z 551 (M$^+$).

Example 81

Preparation of 5,6-bis(difluoromethoxy)-2-((4-fluoro-1-(2-fluorobenzyl)piperidin-4-yl)methyl)-2,3-dihydro-1H-inden-1-one (DC104)

4-nitrobenzyl bromide was replaced by 2-fluorobenzyl bromide, 5,6-dimethoxyindanone was replaced by 5,6-di(trifluoromethoxy)indanone and the rest of raw materials, reagents and the preparation were identical with those in example 1 to obtain DC104 as target product. $^1$H NMR (CDCl$_3$, 400 MHz) δ 7.48-7.56 (m, 3H), 7.36 (m, 2H), 7.04-7.21 (m, 3H), 3.66 (s, 2H), 3.37 (m, 1H), 2.58-2.83 (m, 2H), 1.62-2.24 (m, 4H), 1.56-1.62 (m, 6H); LRMS (EI) m/z 487 (M$^+$).

Example 82

Preparation of 5,6-bis(2,2-difluoroethoxy)-2-((4-fluoro-1-(2-fluorobenzyl)piperidin-4-yl)methyl)-2,3-dihydro-1H-inden-1-one (DC105)

4-nitrobenzyl bromide was replaced by 2-fluorobenzyl bromide, 5,6-dimethoxyindanone was replaced by 5,6-di(2,2-difluoroethoxy)indanone and the rest of raw materials, reagents and the preparation were identical with those in example 1 to obtain DC105 as target product. $^1$H NMR (CDCl$_3$, 400 MHz) δ 7.48-7.56 (m, 3H), 7.04-7.21 (m, 3H), 5.56 (m, 2H), 4.46 (m, 4H), 3.66 (s, 2H), 3.37 (m, 1H), 2.58-2.83 (m, 2H), 1.62-2.24 (m, 4H), 1.56-1.62 (m, 6H); LRMS (EI) m/z 515 (M$^+$).

Example 83

Preparation of 5,6-dichloro-2-((4-fluoro-1-(2-fluorobenzyl)piperidin-4-yl)methyl)-2,3-dihydro-1H-inden-1-one (DC106)

4-nitrobenzyl bromide was replaced by 2-fluorobenzyl bromide, 5,6-dimethoxyindanone was replaced by 5,6-dichloroindanone and the rest of raw materials, reagents and the preparation were identical with those in example 1 to obtain DC106 as target product. $^1$H NMR (CDCl$_3$, 400 MHz) δ 7.78 (s, 1H), 7.48-7.56 (m, 3H), 7.10-7.21 (m, 2H), 3.66 (s, 2H), 3.37 (m, 1H), 2.58-2.83 (m, 2H), 2.24 (m, 4H), 1.56-1.62 (m, 6H); LRMS (EI) m/z 423 (M$^+$).

Example 84

Preparation of 4-((5,6-dimethoxy-1-oxo-2,3-dihydro-1H-inden-2-yl)methyl)-4-fluoro-1-(2-fluorobenzyl)piperidine-2-carboxylate (DC107)

Boc-piperidone was replaced by 2-methoxycarbonyl-Boc-piperidone, 4-nitrobenzyl bromide was replaced by 2-fluorobenzyl bromide and the rest of raw materials, reagents and the preparation were identical with those in example 1 to obtain DC107 as target product. $^1$H NMR (CDCl$_3$, 400 MHz) δ 7.48-7.56 (m, 3H), 7.04-7.21 (m, 3H), 3.83 (s, 6H), 3.68 (s, 3H), 3.62 (s, 2H), 3.37 (m, 1H), 3.07 (m, 1H), 2.41-2.83 (m, 4H), 1.56-1.85 (m, 6H); LRMS (EI) m/z 473 (M$^+$).

Example 85

Preparation of 4-((5,6-dimethoxy-1-oxo-2,3-dihydro-1H-inden-2-yl)methyl)-4-fluoro-1-(2-fluorobenzyl)piperidine-2-carboxylic acid (DC108)

Compound DC107 was dissolved in tetrahydrofuran and water (1:1, v/v) and 2 eq of aqueous NaOH solution was added and refluxed overnight. After acidized, extracted by ethyl acetate, dried and purified, the target product DC108 was obtained. $^1$H NMR (CDCl$_3$, 400 MHz) δ 7.48-7.56 (m, 3H), 7.04-7.21 (m, 3H), 3.83 (s, 6H), 3.62 (s, 2H), 3.37 (m, 1H), 3.07 (m, 1H), 2.41-2.83 (m, 4H), 1.56-1.85 (m, 6H); LRMS (EI) m/z 459 (M$^+$).

Example 86

Preparation of 2-((4-fluoro-1-(2-fluorobenzyl)-2-methylpiperidin-4-yl)methyl)-5,6-dimethoxy-2,3-dihydro-1H-inden-1-one (DC109)

Boc-piperidone was replaced by 2-methyl-Boc-piperidone, 4-nitrobenzyl bromide was replaced by 2-fluorobenzyl bromide and the rest of raw materials, reagents and the preparation were identical with those in example 1 to obtain DC109 as target product. $^1$H NMR (CDCl$_3$, 400 MHz) 7.48-7.56 (m, 3H), 7.10-7.12 (m, 3H), 3.83 (s, 6H), 3.62 (s, 2H), 3.37 (m, 1H), 2.41-2.83 (m, 5H), 1.46-1.56 (m, 6H), 1.12 (m, 3H); LRMS (EI) m/z 473 (M$^+$).

Example 87

Preparation of 2-((4-fluoro-1-phenethylpiperidin-4-yl)methyl)-5,6-dimethoxy-2,3-dihydro-1H-inden-1-one (DC110)

4-nitrobenzyl bromide was replaced by 2-fluorophenethyl bromide and the rest of raw materials, reagents and the preparation were identical with those in example 1 to obtain DC110 as target product. $^1$H NMR (CDCl$_3$, 400 MHz) 7.54-7.57 (m, 3H), 7.04-7.27 (m, 3H), 3.83 (s, 6H), 3.37 (m, 1H), 2.58-2.69 (m, 6H), 2.24 (m, 4H), 1.56-1.62 (m, 6H); LRMS (EI) m/z 429 (M$^+$).

Example 88

Preparation of 2-((4-fluoro-1-(2-fluorophenethyl)piperidin-4-yl)methyl)-5,6-dimethoxy-2,3-dihydro-1H-inden-1-one (DC111)

4-nitrobenzyl bromide was replaced by phenethyl bromide and the rest of raw materials, reagents and the preparation were identical with those in example 1 to obtain DC111 as target product. $^1$H NMR (CDCl$_3$, 400 MHz) 7.54 (s, 1H), 7.27-7.40 (m, 5H), 7.04 (s, 1H), 3.83 (s, 6H), 3.37 (m, 1H), 2.58-2.69 (m, 6H), 2.24 (m, 4H), 1.56-1.62 (m, 6H); LRMS (EI) m/z 411 (M$^+$).

Pharmacological Activity Assay Example

Experimental Example 1

The inhibition effects of compounds as shown in general formula I on acetylcholinesterase and butyrylcholinesterase were determined by tests, according to Biochem. Pharmacol. 1961, 7, 88-95 and Acta pharmacologica Sinica 1999, 20, 141-5. The experimental data were shown in Table 1.

Sample processing: All samples were formulated as 10-2 mol/L solution by using 100% DMSO. 10-2 mol/L solution was used in microdetermination. 1 µL was taken to use in single tube experiment. The final concentration of the reaction was 4×10−5 mol/L.

Solvent control: 0.4% DMSO was used in microdetermination. The inhibition ratio of the sample was obtained wherein the effect of solvent was deducted.

Positive control: Huperzine A, the final concentration of the reaction was 1.65×10-6 mol/L.

Acetylcholinesterase: rat cortex

Butyrylcholinesterase: rat serum

TABLE 1

The inhibition effects of compounds on acetylcholinesterase and butyrylcholinesterase

| No. | acetylcholinesterase inhibitory activity | | butyrylcholinesterase inhibitory activity | | chemical property | | |
|---|---|---|---|---|---|---|---|
| | inhibition ratio (%) | IC$_{50}$ (nmol) | inhibition ratio (%) | IC$_{50}$ (nmol) | LogP | CLogP | tPSA |
| E2020 | 77.05 | 2.00 | 72.82 | — | 4.01 | 4.60 | 38.77 |
| DC1 | 72.85 | 8780 | 46.68 | — | 4.12 | 4.18 | 90.58 |
| DC3 | 80.04 | — | 36.42 | — | 3.40 | 4.01 | 62.56 |
| DC4 | 75.65 | — | 72.82 | — | 4.34 | 5.44 | 38.77 |
| DC5 | 82.04 | 2.67 | 0.00 | — | 3.53 | 4.58 | 38.77 |
| DC6 | 51.7 | — | 1.24 | — | 4.9 | 5.47 | 48.00 |
| DC7 | 69.06 | — | 8.40 | — | 5.07 | 6.26 | 38.77 |
| DC8 | 76.05 | 27100 | 49.48 | — | 4.25 | 4.24 | 90.58 |
| DC9 | 97.34 | — | 33.79 | — | 3.98 | 5.34 | 57.23 |
| DC10 | 97.34 | — | 83.11 | — | 3.69 | 4.73 | 38.77 |
| DC11 | 84.63 | 4.33 | 12.76 | — | 4.2 | 5.30 | 38.77 |
| DC12 | 98.08 | — | 38.15 | — | 3.84 | 4.73 | 38.77 |
| DC13 | 97.19 | — | 29.25 | — | 3.40 | 3.87 | 62.56 |
| DC14 | 85.03 | 4.00 | 54.77 | — | 4.2 | 5.30 | 38.77 |
| DC15 | 72.65 | 7040 | 0.31 | — | 4.36 | 5.44 | 38.77 |
| DC16 | 75.25 | — | 0.00 | — | 4.29 | 5.32 | 38.77 |
| DC17 | 81.84 | 2.00 | 49.79 | — | 3.84 | 4.80 | 38.77 |
| DC18 | 93.80 | — | 14.99 | — | 4.29 | 5.32 | 38.77 |
| DC19 | 82.44 | 0.96 | 71.58 | — | 3.37 | 4.44 | 38.77 |
| DC20 | 82.04 | 0.86 | 71.58 | — | 3.53 | 4.58 | 38.77 |
| DC21 | 82.24 | — | 75.02 | — | 3.83 | 4.58 | 38.77 |
| DC22 | 58.49 | — | 4.36 | — | 5.21 | 6.21 | 38.77 |
| DC23 | 57.09 | — | 0.00 | — | 2.81 | 3.19 | 55.84 |
| DC27 | 97.34 | — | 18.07 | — | 3.69 | 4.73 | 38.27 |
| DC28 | 96.5 | — | — | — | 4.16 | 4.95 | 38.77 |
| DC29 | 97.78 | — | 64.92 | — | 3.86 | 4.94 | 38.77 |
| DC30 | 97.49 | — | 5.18 | — | 4.29 | 5.32 | 38.77 |
| DC31 | 85.82 | — | 35.06 | — | 2.78 | 4.01 | 38.77 |
| DC32 | 90.10 | — | 46.68 | — | 3.20 | 4.57 | 38.77 |
| DC33 | 90.10 | — | 0.36 | — | 3.61 | 5.13 | 38.77 |
| DC34 | 95.57 | — | 68.48 | — | 4.03 | 5.69 | 38.77 |
| DC35 | 94.39 | — | 10.08 | — | 3.84 | 4.79 | 38.77 |
| DC36 | 90.25 | — | 5.18 | — | 5.05 | 6.33 | 38.77 |
| DC37 | 81.98 | — | 20.80 | — | 3.4 | 4.01 | 62.56 |
| DC38 | 96.90 | — | 72.57 | — | 3.53 | 4.58 | 38.77 |
| DC41 | 56.8 | — | — | — | 4.85 | 4.49 | 90.58 |
| DC43 | 88.9 | — | — | — | 3.68 | 4.33 | 62.59 |
| DC44 | 95.27 | — | 34.15 | — | 4.62 | 5.75 | 38.77 |
| DC45 | 97.19 | — | 82.56 | — | 3.80 | 4.89 | 38.77 |
| DC47 | 75.33 | — | 7.63 | — | 5.35 | 6.58 | 38.77 |
| DC48 | 77.3 | — | — | — | 4.98 | 4.56 | 90.58 |
| DC50 | 83.75 | — | 0.00 | — | 3.47 | 4.72 | 65.07 |
| DC51 | 85.08 | — | 15.26 | — | 4.48 | 5.62 | 38.77 |
| DC52 | 93.80 | — | 0.73 | — | 4.85 | 4.42 | 90.58 |
| DC54 | 90.3 | — | — | — | 4.48 | 5.62 | 38.77 |
| DC57 | 96.75 | — | 1017 | — | 4.12 | 5.11 | 38.77 |
| DC59 | 86.12 | — | 69.03 | — | 3.65 | 4.75 | 38.77 |
| DC60 | 95.13 | — | 64.31 | — | 3.80 | 4.89 | 38.77 |
| DC61 | 96.75 | — | 61.04 | — | 3.80 | 4.89 | 38.77 |

TABLE 1-continued

The inhibition effects of compounds on acetylcholinesterase and butyrylcholinesterase

| No. | acetylcholinesterase inhibitory activity | | butyrylcholinesterase inhibitory activity | | chemical property | | |
|---|---|---|---|---|---|---|---|
| | inhibition ratio (%) | IC$_{50}$ (nmol) | inhibition ratio (%) | IC$_{50}$ (nmol) | LogP | CLogP | tPSA |
| DC68 | 93.80 | — | 4.0 | — | 4.44 | 5.26 | 38.77 |
| DC69 | 97.49 | — | 58.86 | — | 4.13 | 5.25 | 38.77 |
| DC70 | 76.51 | — | 0.09 | — | 4.57 | 5.64 | 38.77 |
| DC75 | 72.53 | — | 13.53 | — | 4.12 | 5.11 | 38.77 |
| DC76 | 85.3 | — | — | — | 5.32 | 6.64 | 38.77 |
| DC77 | 97.09 | 0.90 | 72.0 | — | 4.2 | 5.64 | 38.77 |
| DC78 | 95.04 | 0.96 | 71.0 | — | 5.18 | 6.70 | 38.77 |
| DC79 | 93.05 | 1.86 | 75.0 | — | 4.45 | 4.77 | 57.23 |
| DC103 | 92.04 | 0.86 | 70.0 | — | 5.49 | 6.17 | 38.77 |
| DC104 | 98.02 | 0.76 | 71.8 | — | 4.95 | 5.48 | 38.77 |
| DC105 | 98.14 | 0.99 | 61.5 | — | 4.18 | 5.73 | 38.77 |
| DC106 | 70.05 | 500.02 | 88.0 | — | 4.9 | 6.09 | 20.31 |
| DC107 | 76.03 | 23.0 | 75.6 | — | 3.21 | 4.39 | 65.07 |
| DC108 | 82.49 | 9.96 | 71.58 | — | 2.95 | 2.50 | 76.07 |
| DC109 | 88.44 | 10.90 | 76.62 | — | 3.85 | 5.10 | 38.77 |
| DC110 | 88.55 | 12.32 | 66.30 | — | 3.65 | 4.58 | 38.77 |
| DC111 | 92.44 | 1.96 | 71.58 | — | 3.81 | 4.72 | 38.77 | note:
The Physical and chemical properties of the compounds (LogP, CLogP and tPSA values) were values predicted by Chemdraw software in ChemOffice package. "—" represents "undetermined".

Conclusion:

Drug E2020 on the market was used as positive control in the evaluation of biological activity. The acetylcholinesterase inhibition ratio thereof was 77% and IC$_{50}$ value was 2.0 nM. It can be seen from the data obtained from the above table that the percent inhibition rates of majority of newly synthesized compounds were superior to that of the positive control compound E2020, wherein nearly 30 compounds can achieve more than 90% of inhibition ratio which is much higher than that of E2020. IC$_{50}$ values of many compounds on acetylcholinesterase were less than 1 nM and significantly better than that of the positive control drug E2020 (2 nM of IC$_{50}$). Moreover, the physical and chemical properties (Log P, CLog P and tPSA, etc.) of these compounds are comparable to those of positive drug and also have good druggability.

Experimental Example 2

Acute toxicities of some compounds as shown in general formula I on mice were determined and the data were shown in Table 2.

Sample processing: When getting samples, they were undissolved. 5% DMSO was added and shaken sufficiently to dissolve the samples. Then 1% cosolvent EL (polyoxyethylated castor oil) was added and water was used to make up the remaining volumn to obtain 10 mg/mL of the sample. The samples were suspensions. Experimental animals: KM mice, 22-29 g, half male and half female.

Experimental method: Mice were randomly divided into groups. 100 mg/kg of test compounds DC19 and DC20 were administered orally, respectively. An equal amount of 5% DMSO and 1% EL solution were administered to the solvent control group. After administration, mice was observed for the presence or absence of significant adverse effects or death.

TABLE 2

Acute toxicities of compounds on mice

| group | sex | number of animals | dosage (mg/kg) | response symptoms |
|---|---|---|---|---|
| solvent control | male | 1 | / | normal |
| | female | 1 | / | normal |
| DC19 | male | 1 | 100 | 7 min, myasthenia, reduction in autonomic activity; 30 min, lacrimal secretion, immobility; 3 h after administration, death |
| | female | 1 | 100 | 30 min squint |
| DC20 | male | 1 | 100 | 6 min, myasthenia, reduction in autonomic activity; 15 min, lacrimal secretion, salivary secretion, immobility; 24 h, death |
| | female | 1 | 100 | 8 min, myasthenia, lacrimal secretion, salivary secretion; 20 min, muscular fibrillation, immobility |

Experimental Conclusion

After high doses of samples were administrated, some phenomenons such as myasthenia, lacrimal secretion and salivary secretion etc. caused by acetylcholinesterase inhibitor in mice of each group were appeared. The results showed that the compounds of the present invention can pass through the blood-brain barrier and act on the acetylcholinesterase in the brain, thereby playing a role in the treatment of senile dementia.

Experimental Example 3

In vivo inhibition effects of some compounds as shown in general formula I and donepezil (Donepezil, positive control, purchased from sigma company) on cortex and hippocampus acetylcholinesterase of mice were determined.

Sample processing: When getting samples, they were undissolved. 5% DMSO was added and shaken sufficiently to dissolve the samples. Then 1% cosolvent EL (polyoxyethylated castor oil) was added and water was used to make up the remaining volumn to obtain 10 mg/mL sample. The samples were diluted gradually to 0.3 mg/mL, 1 mg/mL and 3 mg/mL. The samples were suspensions. The samples were administrated orally according to 0.1~mL/10 g of volumn to weight ratio. An equal amount of 5% DMSO and 1% EL solution was administered orally to the solvent control group.

Experiment Methods and Materials (1) Acetylcholinesterase: mouse cortex and hippocampus. 1 h after orally administrated, the mice were decapitated. After the brains were taken out, the hippocampus and cortex were quickly stripped on the ice. To the cortex was added ice-cold 75 mM PBS, and homogenated to form 30× tissue homogenate and to the hippocampus was added ice-cold 75 mM PBS and homogenated to form 40× tissue homogenate. And finally 1/10 by volumn of OMPA was added and placed on the ice to be tested.

(2) Test Method: To the samples were added a reaction system containing PBS, H$_2$O, S-Ach and DTNB. Except for the blank tube, to the rest of the tubes were added an appropriate amount of enzyme. The reaction was carried out at room temperature for 20 minutes. SDS was added to each tube to quench the reaction. An appropriate amount of enzyme was added to the blank tube. Absorbance of each tube was determined by UV-visible spectrophotometer (OD440 nm).

TABLE 3

The results of acetylcholinesterase acvitity in vivo

| group | Dosage (mg/kg) | number of animals | Acetylcholinesterase activity (%) | |
|---|---|---|---|---|
| | | | cortex | hippocampus |
| solvent control | / | 4 | 100.00 ± 4.73 | 100.00 ± 4.72 |
| Donepezil | 10 | 4 | 73.50 ± 7.50* | 64.91 ± 6.82** |
| DC20 | 0.3 | 4 | 85.33 ± 2.72* | 84.53 ± 5.98 |
| | 1 | 4 | 77.98 ± 4.67* | 80.24 ± 1.90** |
| | 3 | 4 | 57.05 ± 8.04** | 49.88 ± 6.53** |
| | 10 | 4 | 33.98 ± 4.88 | 34.38 ± 2.48 | note:
The values in the table showed the activities of cortex and hippocampus acetylcholinesterase. The activity of the solvent control group was set as 100%. The activities of the rest groups (Mean ± SEM) were percentage obtained from the the rest groups compared with the solvent control group.
*P < 0.05 (compared with the solvent control group),
**P < 0.01 (compared with the solvent control group).

Experimental Conclusion

The activities of 0.3 mg/kg, 1 mg/kg, 3 mg/kg and 10 mg/kg of compound DC20 on the cortex acetylcholinesterase were 85.33%, 77.98%, 57.05% and 33.98%, respectively and compound DC20 achieved 14.67%, 22.02%, 42.95% and 66.02% of inhibition compared with the solvent control group. The activities of 0.3 mg/kg, 1 mg/kg, 3 mg/kg and 10 mg/kg of compound DC20 on the hippocampus acetylcholinesterase were 84.53%, 80.24%, 49.88% and 34.38%, respectively and compound DC20 achieved 15.47%, 19.76%, 50.12% and 65.62% of inhibition compared with the solvent control group.

1 mg/kg, 3 mg/kg and 10 mg/kg of DC20 showed significant inhibition effects on both mouse cortex acetylcholinesterase and mouse hippocampus acetylcholinesterase.

Wherein, the inhibition effects of 1 mg/kg of DC20 on mouse cortex and hippocampus AChE were comparable to those of 10 mg/kg of positive control drug Donepezil. Therefore, the overall activity of compound DC20 was better than that of Donepezil.

Experimental Example 4

The inhibition effects of the monomers of some compounds as shown in general formula I (R-isomer, S-isomer) and donepezil (positive control) on cortex and hippocampus acetylcholinesterase of mice were determined.

Sample processing: 5% DMSO was added and shaken sufficiently to dissolve the samples. Then 1% cosolvent EL (polyoxyethylated castor oil) was added and water was used to make up the remaining volumn to obtain 10 mg/mL sample. The samples were diluted gradually to 1 mg/mL and 0.1 mg/mL. The samples were administrated orally according to 0.1 mL/10 g of volumn to weight. An equal amount of 5% DMSO and 1% EL solution were administered orally to the solvent control group.

Experiment Methods and Materials (1) Acetylcholinesterase: mouse cortex and hippocampus. 1 h after orally administrated, the mice were decapitated. After the brains were taken out, the hippocampus and cortex were quickly stripped on the ice. To the cortex was added ice-cold 75 mM PBS and homogenated to form 30× tissue homogenate and to the hippocampus was added ice-cold 75 mM PBS and homogenated to form 40× tissue homogenate. And finally 1/10 by volumn of OMPA was added and placed on the ice to be tested.

(2) Test Method: To the samples were added a reaction system containing PBS, H2O, S-ACh and DTNB. Except for the blank tube, the rest of the tubes were added with an appropriate amount of enzyme. The reaction was carried out at room temperature for 20 minutes. SDS was added to each tube to quench the reaction. An appropriate amount of enzyme was added to the blank tube. Absorbance of each tube was determined by UV-visible spectrophotometer (OD440 nm).

The experiment results were as follows.

TABLE 4

| group | dosage (mg/kg) | number of animals | acetylcholinesterase activity (%) | |
|---|---|---|---|---|
| | | | cortex-R | hippocampus-R |
| solvent control | / | 4 | 100.00 ± 0.81 | 100.00 ± 6.11 |
| Donepezil | 10 | 4 | 78.06 ± 6.01* | 76.81 ± 4.22* |
| DC20-R | 10 | 4 | 38.36 ± 11.44** | 36.66 ± 6.23** |
| | 1 | 4 | 66.30 ± 7.81** | 63.84 ± 5.76** |
| DC20-S | 10 | 4 | 68.94 ± 8.94* | 65.94 ± 5.02** |
| | 1 | 4 | 94.51 ± 10.03 | 86.19 ± 4.84 | note:
The values in the table showed the activities of cortex and hippocampus acetylcholinesterase. The activity of the solvent control group was set as 100%. The activities of the rest groups (Mean ± SEM) were percentage obtained from the the rest groups compared with the solvent control group.
*P < 0.05 (compared with the solvent control group),
**P < 0.01 (compared with the solvent control group).

Experimental Conclusion

The activities of 10 mg/kg and 1 mg/kg of compound DC20-R on the cortex acetylcholinesterase were 38.36% and 66.30%, respectively and compound DC20-R achieved 61.64% and 33.70% of inhibition compared with the solvent control group. The activities of 10 mg/kg and 1 mg/kg of compound DC20-R on the hippocampus acetylcholinesterase were 36.66% and 63.84%, respectively and the compound achieved 63.34% and 36.16% of inhibition compared with the solvent control group. 10 mg/kg and 1 mg/kg of DC20-R showed significant inhibition effects on both of mouse cortex acetylcholinesterase and mouse hippocampus acetylcholinesterase.

The activities of 10 mg/kg and 1 mg/kg of compound DC20-S on the cortex acetylcholinesterase were 68.94% and 94.51%, respectively and compound DC20-S achieved 31.06% and 5.49% of inhibition compared with the solvent control group. The activities of 10 mg/kg and 1 mg/kg of compound DC20-S on the hippocampus acetylcholinesterase were 65.94% and 86.19%, respectively and the compound achieved 34.06% and 13.81% of inhibition compared with the solvent control group. 10 mg/kg of DC20-S showed significant inhibition effects on both of mouse cortex acetylcholinesterase and mouse hippocampus acetylcholinesterase.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:
1. A fluoro-substituted cyclic amine compound as shown in general formula I, or a racemate, a R-isomer, a S-isomer, a pharmaceutically acceptable salt thereof or a mixture thereof:

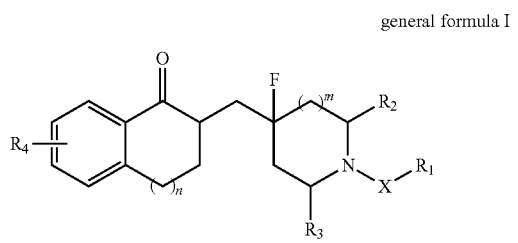

general formula I wherein
m is 1;
n is 0;
X is $(CH_2)_p$ or CO, wherein p is an integer of 0-3;
$R_1$ is a substituted or unsubstituted $C_3$-$C_{10}$ cycloalkyl or a substituted $C_6$-$C_{12}$ aryl, wherein the substituent(s) of $R_1$ is 1, 2, 3, 4 or 5 same or different substituents independently selected from the group consisting of a halogen, a $C_1$-$C_6$ alkyl, a halogen substituted $C_1$-$C_6$ alkyl, a $C_1$-$C_6$ alkoxy, a $C_1$-$C_6$ alkoxycarbonyl, a halogen substituted $C_1$-$C_6$ alkoxy, a $C_2$-$C_6$ alkenyl, a $C_2$-$C_6$ alkynyl, a $C_3$-$C_8$ cycloalkyl, a cyano, a nitro, an amino, a hydroxyl, a hydroxymethyl, a carboxyl, a mercapto, a sulfonyl, a $C_6$-$C_{10}$ aryl and a 3-12 membered heterocyclic radical; or two adjacent substituents of the $C_6$-$C_{12}$ aryl and carbon atom(s) of adjacent aromatic ring together form a $C_3$-$C_7$ cycloalkyl, a $C_3$-$C_7$ cycloalkenyl or a 3-7 membered heterocyclic radical; and each heterocyclic radical independently contains 1-4 heteroatoms selected from the group consisting of O, S and N; provided that when the $C_6$-$C_{12}$ aryl is substituted with one halogen, then the halogen is F;

each of $R_2$ and $R_3$ is independently selected from the group consisting of a hydrogen, a carboxyl, a $C_1$-$C_4$ alkoxycarbonyl and a $C_1$-$C_4$ alkyl; or $R_2$ and $R_3$ together form a $C_1$-$C_4$ alkylidene;
$R_4$ is 1-4 same or different substituents selected from the group consisting of a hydrogen, a halogen, a $C_1$-$C_6$ alkyl, a halogen substituted $C_1$-$C_6$ alkyl, a $C_1$-$C_6$ alkoxy, a halogen substituted $C_1$-$C_6$ alkoxy, a $C_2$-$C_6$ alkenyl, a $C_2$-$C_6$ alkynyl, a cyano, a nitro, an amino, a hydroxyl, a hydroxymethyl, a carboxyl, a mercapto, a sulfonyl, —O[(CH$_2$)$_q$O]$_r$R$_5$, a phenyl and a 3-12 membered heterocyclic radical; wherein the heterocyclic radical contains 1-3 heteroatoms selected from the group consisting of O, S and N; $R_5$ is selected from the group consisting of a hydrogen, a halogen, a $C_1$-$C_6$ alkyl, a halogen substituted $C_1$-$C_6$ alkyl, a $C_2$-$C_6$ alkenyl, a $C_2$-$C_6$ alkynyl and a hydroxymethyl; q is 1, 2, 3 or 4; and r is 1, 2, 3 or 4; and
said halogen is F, Cl, Br or I.

2. The fluoro-substituted cyclic amine compound according to claim 1, or the racemate, R-isomer, S-isomer, pharmaceutically acceptable salt thereof or mixture thereof, wherein,
X is $(CH_2)_p$, p is 1 or 2;
$R_1$ is a substituted or unsubstituted $C_3$-$C_8$ cycloalkyl or a substituted $C_6$-$C_{12}$ aryl, wherein the substituent(s) of $R_1$ is 1-5 same or different substituents independently selected from the group consisting of a halogen, a $C_1$-$C_6$ alkyl, a halogen substituted $C_1$-$C_6$ alkyl, a $C_1$-$C_6$ alkoxy, a $C_1$-$C_6$ alkoxycarbonyl, a halogen substituted $C_1$-$C_6$ alkoxy, a $C_2$-$C_6$ alkenyl, a $C_2$-$C_6$ alkynyl, a $C_3$-$C_8$ cycloalkyl, a cyano, a nitro, an amino, a hydroxyl, a hydroxymethyl, a carboxyl, a mercapto, a sulfonyl, a phenyl, a naphthyl and 3-12 membered heterocyclic radical; or two adjacent substituents of the $C_6$-$C_{12}$ aryl and carbon atom(s) of adjacent aromatic ring together form a 3-7 membered heterocyclic radical, wherein the heterocyclic radical contains 1-3 oxygen atoms; provided that when the $C_6$-$C_{12}$ aryl is substituted with one halogen, then the halogen is F;
each of $R_2$ and $R_3$ is independently selected from the group consisting of a hydrogen, a carboxyl, a methoxycarbonyl, an ethoxycarbonyl, a propoxycarbonyl, a methyl, an ethyl, a propyl, an isopropyl, a butyl and a 2-methylpropyl; or $R_2$ and $R_3$ together form a methylene, an ethylene or a propylene;
$R_4$ is 1-3 same or different substituents selected from the group consisting of a hydrogen, a halogen, a $C_1$-$C_6$ alkyl, a halogen substituted $C_1$-$C_6$ alkyl, a $C_1$-$C_6$ alkoxy, a halogen substituted $C_1$-$C_6$ alkoxy, a $C_2$-$C_6$ alkenyl, a $C_2$-$C_6$ alkynyl, a cyano, a nitro, an amino, a hydroxyl, a carboxyl and —O[(CH$_2$)$_q$O]$_r$R$_5$; $R_5$ is selected from the group consisting of a hydrogen, a halogen, a $C_1$-$C_6$ alkyl and a halogen substituted $C_1$-$C_6$ alkyl; q is 1, 2 or 3; and r is 1, 2 or 3.

3. The fluoro-substituted cyclic amine compound according to claim 2, or the racemate, R-isomer, S-isomer, pharmaceutically acceptable salt thereof or mixture thereof, wherein
$R_1$ is a substituted phenyl, wherein the phenyl is substituted with 1-5 same or different substituents independently selected from the group consisting of a halogen, a $C_1$-$C_6$ alkyl, a $C_1$-$C_6$ alkoxy, a halogen substituted $C_1$-$C_6$ alkoxy, a $C_1$-$C_6$ alkoxycarbonyl, a $C_2$-$C_6$ alkenyl, a $C_2$-$C_6$ alkynyl, a cyano, a nitro, an amino, a hydroxyl, a hydroxymethyl, a trifluoromethyl, a trifluoromethoxy, a carboxyl, a mercapto, a sulfonyl and a phenyl, or two adjacent substituents of the phenyl and carbon atoms of adjacent benzene ring together form

provided that when the phenyl is substituted with one halogen, then the halogen is F;

$R_4$ is 1-2 same or different substituents selected from the group consisting of a hydrogen, a halogen, a $C_1$-$C_6$ alkyl, a $C_1$-$C_6$ alkoxy, a halogen substituted linear or branched $C_1$-$C_6$ alkoxy, a hydroxyl and —O[CH$_2$)$_q$O]$_r$-$R_5$; $R_1$ is selected from a $C_1$-$C_6$ alkyl or a halogen substituted $C_1$-$C_6$ alkyl; q is 1, 2 or 3; and r is 1, 2 or 3.

4. The fluoro-substituted cyclic amine compound according to claim 3, or the racemate, R-isomer, S-isomer, pharmaceutically acceptable salt thereof or mixture thereof, wherein, $R_1$ is a cyclobutyl, a cyclopentyl, a cyclohexyl, a cycloheptyl or a substituted phenyl, wherein the phenyl is substituted with 1-5 same or different substituents independently selected from the group consisting of a halogen, a nitro, a cyano, a trifluoromethyl, a tritluoroethyl, a trifluoropropyl, a trifluoromethoxy, a methyl, an ethyl, a propyl, an isopropyl, a butyl, a tert-butyl, a 2-methylpropyl, a phenyl, a methoxycarbonyl, an ethoxycarbonyl and a propoxycarbonyl, or two adjacent substituents of the phenyl and carbon atoms of adjacent benzene ring together form

provided that when the phenyl is substituted with one halogen then the halogen is F.

5. The fluoro-substituted cyclic amine compound according to claim 1, being a compound of general formula (II), or a racemate, R-isomer, S-isomer, pharmaceutically acceptable salt thereof or mixture thereof:

general formula II

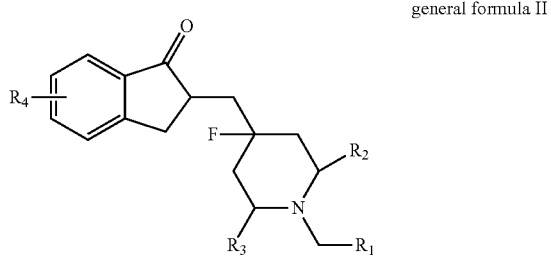

wherein,
$R_1$ is

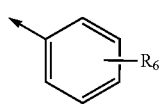

or a C3-C10 cycloalkyl, $R_6$ represents 1, 2, 3, 4 or 5 substituents, the substituent is independently selected from the group consisting of a halogen, a nitro, a cyano, a C1-C6 alkyl, a halogen substituted $C_1$-$C_6$ alkyl, a $C_1$-$C_6$ alkoxy, a halogen substituted $C_1$-$C_6$ alkoxy, a phenyl and a $C_1$-$C_6$ alkoxycarbonyl, or two adjacent $R_6$ and carbon atoms of adjacent benzene ring together form

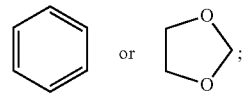 [SMILES: c1ccccc1 ; C1COCO1]

provided that when $R_1$ is substituted with one $R_6$ and $R_6$ is halogen, then the halogen is F;

each of $R_2$ and $R_3$ is independently selected from the group consisting of a hydrogen, a carboxyl, a $C_1$-$C_4$ alkoxycarbonyl and a $C_1$-$C_1$ alkyl; or $R_2$ and $R_3$ together form a $C_1$-$C_4$ alkylidene;

$R_4$ represents 1-4 substituents, and the substituent is independently selected from the group consisting of a hydrogen, a halogen, a $C_1$-$C_6$ alkyl, a halogen substituted $C_1$-$C_6$ alkyl, a $C_1$-$C_6$ alkoxy, a halogen substituted $C_1$-$C_6$ alkoxy, a $C_2$-$C_6$ alkenyl, a $C_2$-$C_6$ alkynyl, a cyano, a nitro, an amino, a hydroxy, an carboxyl and —O[(CH$_2$)$_q$O]$_r$R$_5$; wherein, $R_5$ is selected from the group consisting of a hydrogen, a halogen, a $C_1$-$C_6$ alkyl and a halogen substituted $C_1$-$C_6$ alkyl; q is 1, 2 or 3; and r is 1, 2 or 3.

6. The fluoro-substituted cyclic amine compound according to claim 1, or the racemate, R-isomer, S-isomer, pharmaceutically acceptable salt thereof or mixture thereof, wherein the fluoro-substituted cyclic amine compound is selected from the group consisting of:

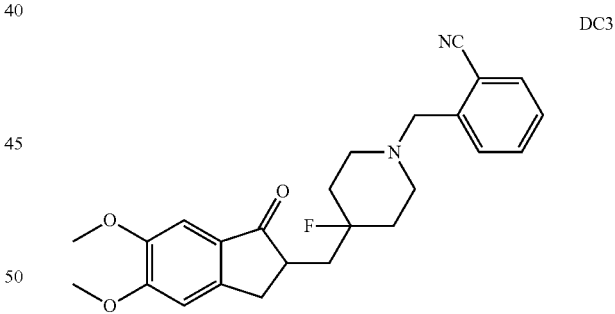

DC3

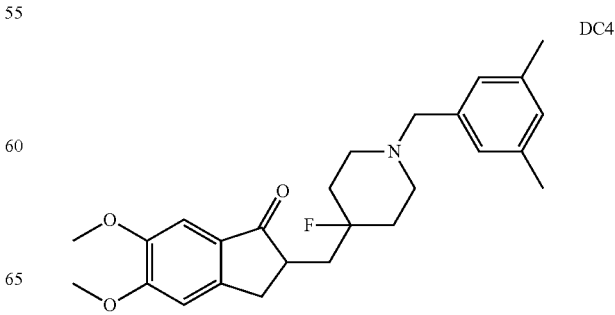

DC4

-continued
DC6
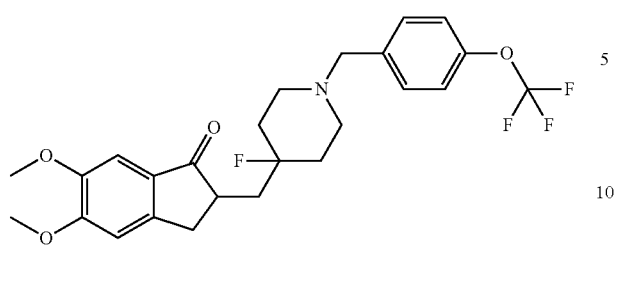
DC7
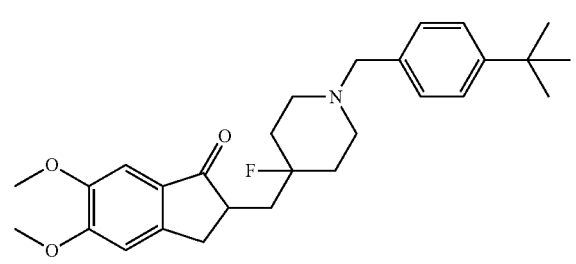
DC8
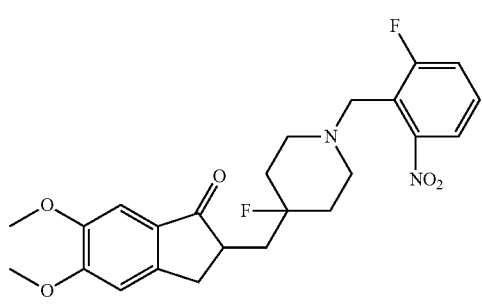
DC9
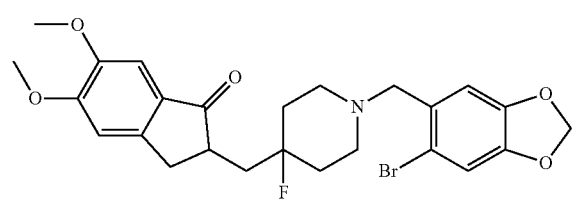
DC10
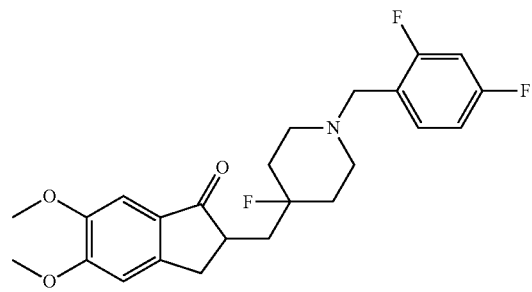
-continued
DC12
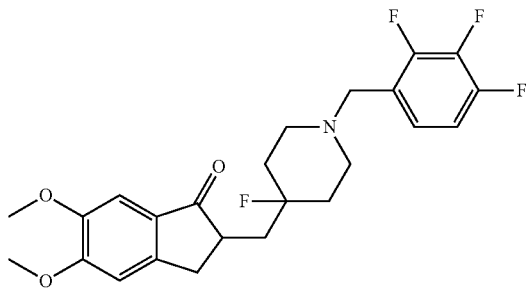
DC13
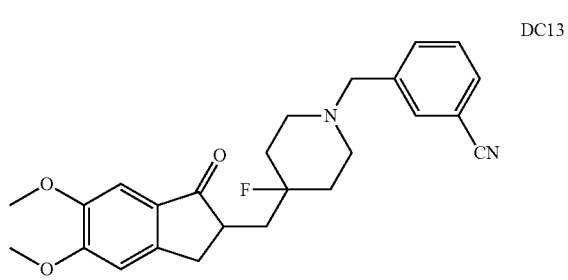
DC15
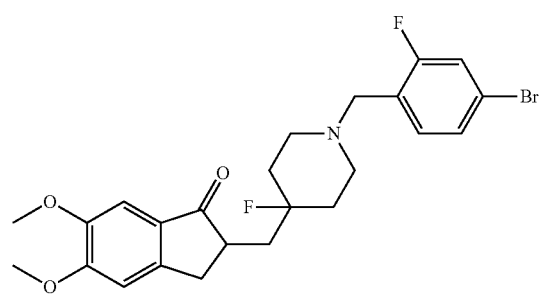
DC16
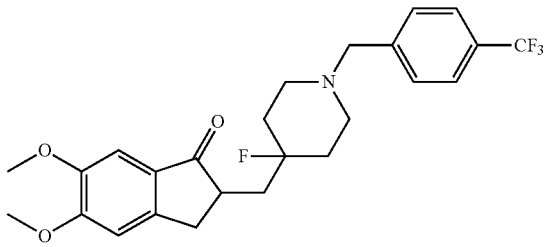
DC17
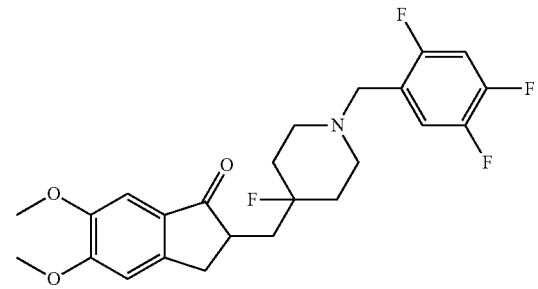

DC18
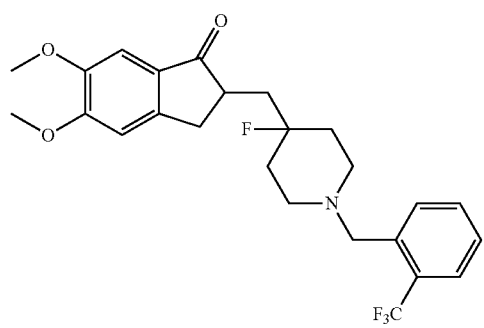
DC20
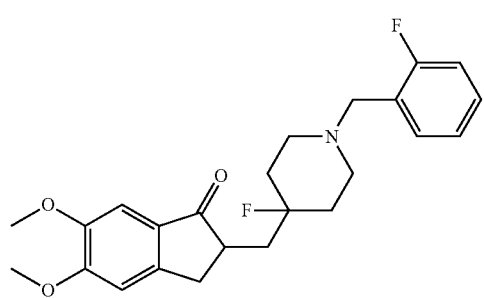
DC21
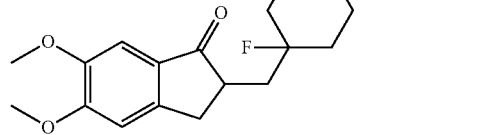
DC22
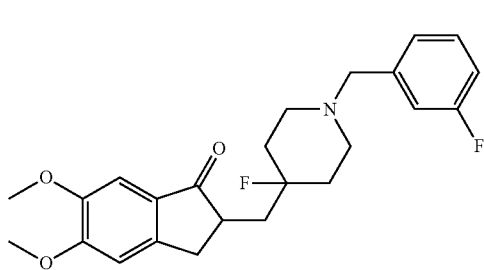
DC27
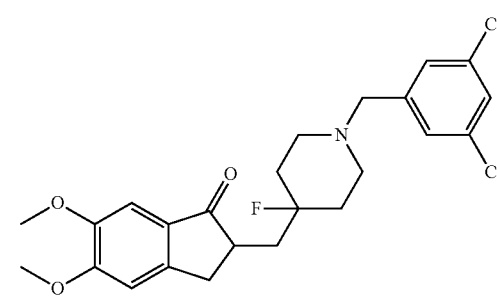
DC28
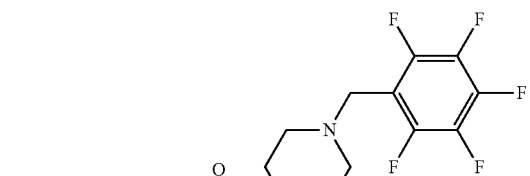
DC30
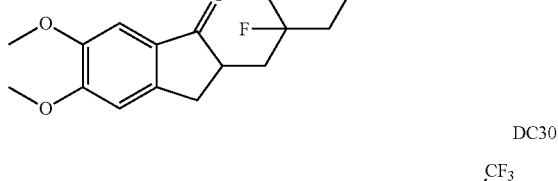
DC31
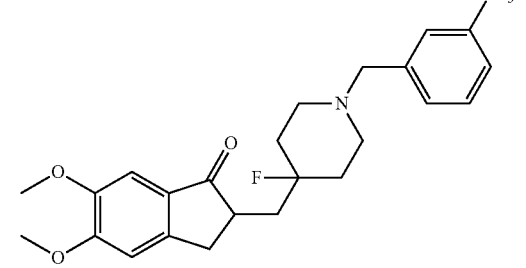
DC32
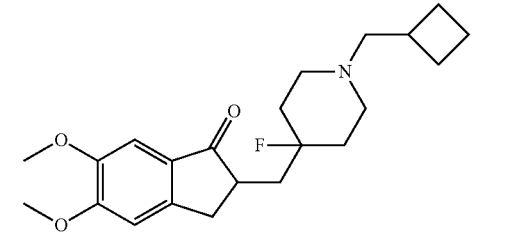
DC33
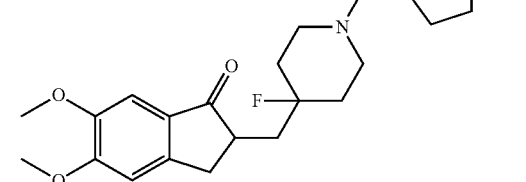
DC34
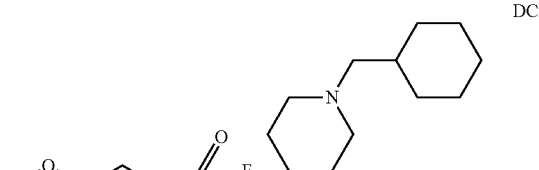

-continued
DC35
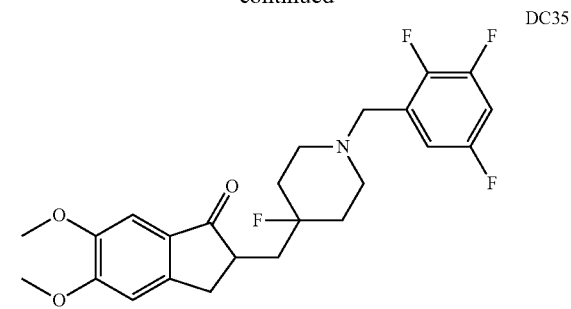
DC36
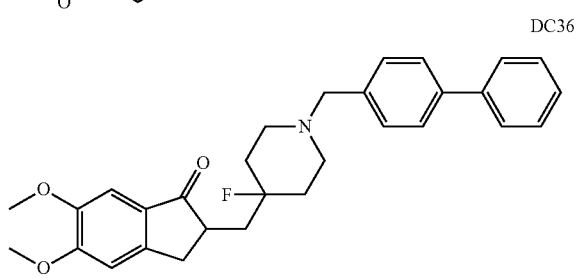
DC41
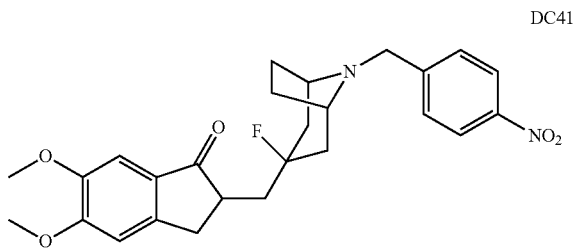
DC43
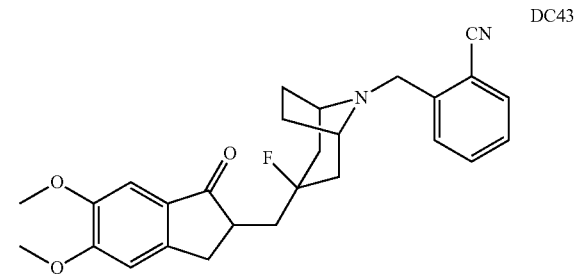
DC44
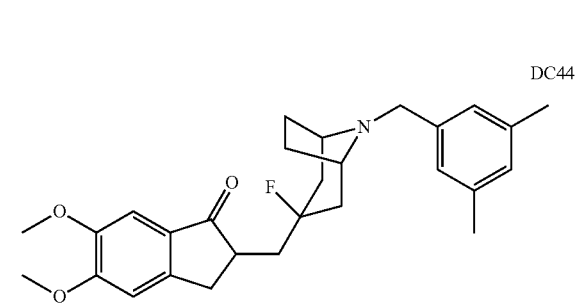
DC45
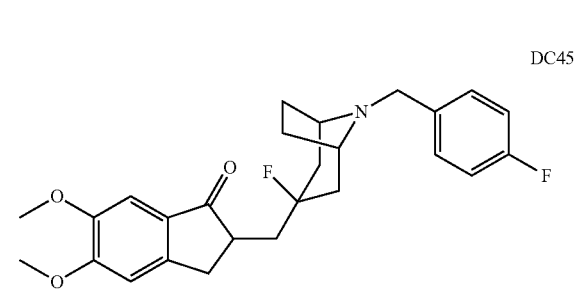
-continued
DC47
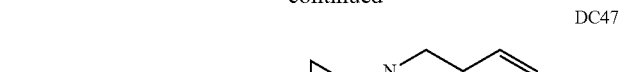
DC48
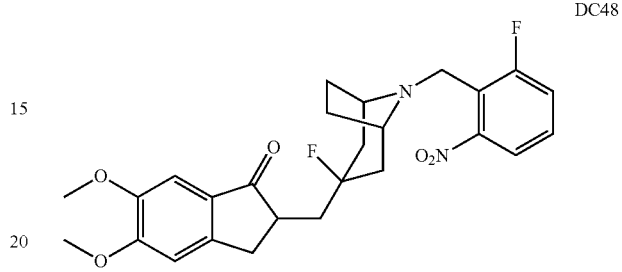
DC50
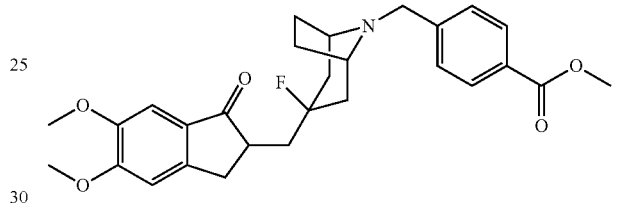
DC52
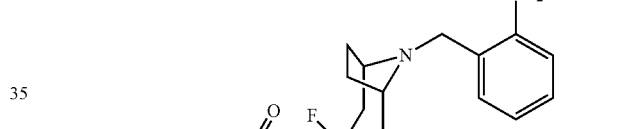
DC57
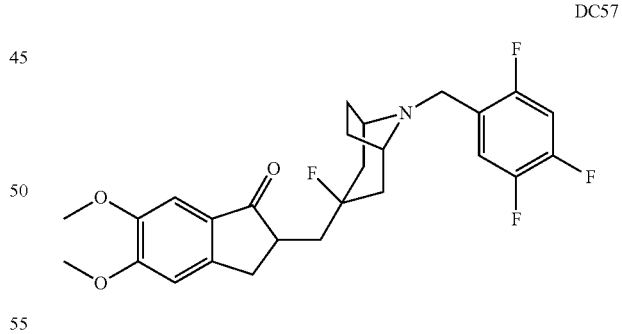
DC60
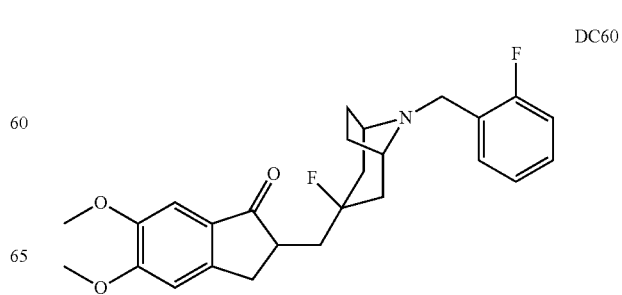

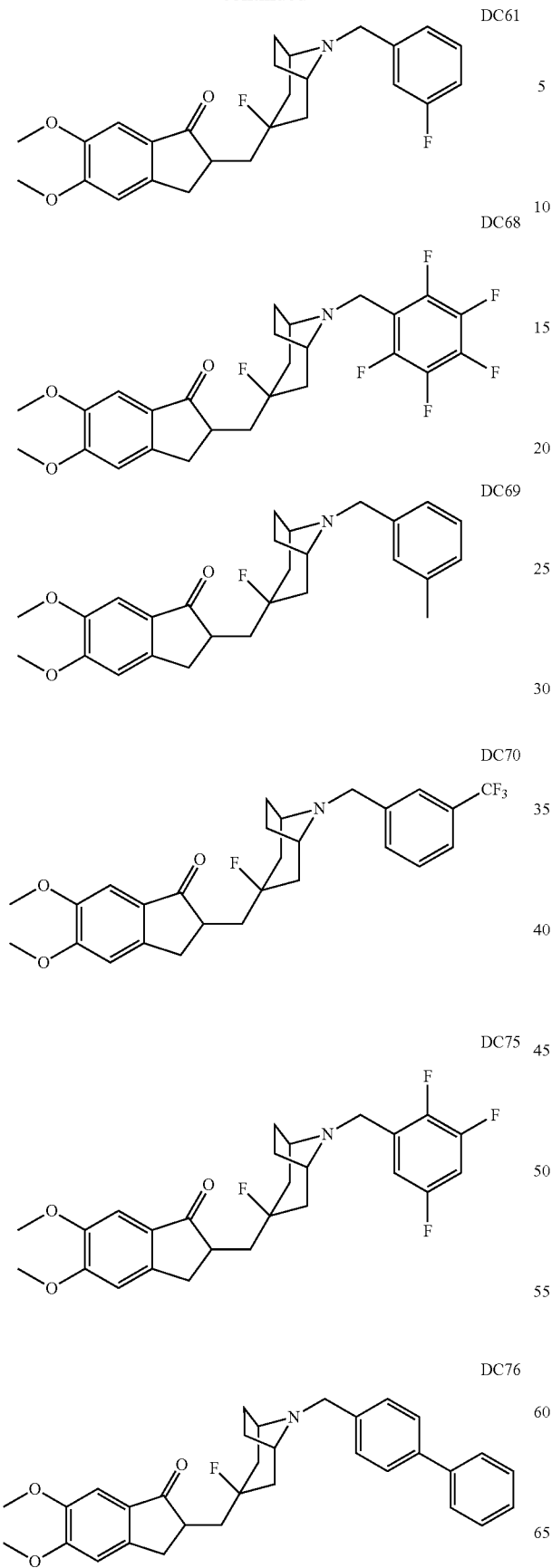
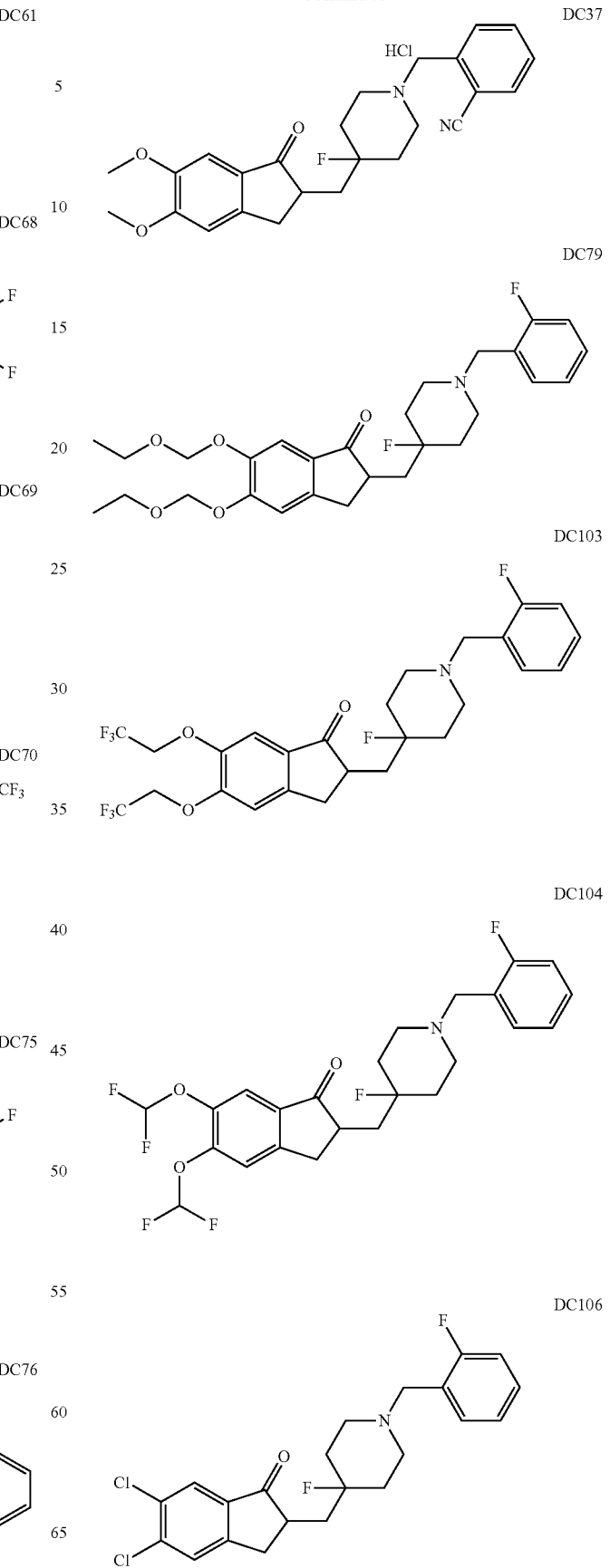

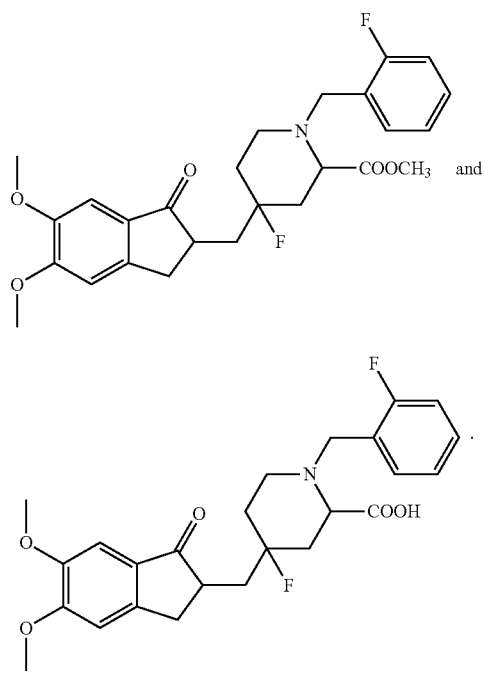

7. The fluoro-substituted cyclic amine compound according to claim 1, or the racemate, R-isomer, S-isomer, pharmaceutically acceptable salt thereof or mixture thereof, wherein
the pharmaceutically acceptable salt is obtained from a reaction of the fluoro-substituted cyclic amine compound with inorganic acid or organic acid; wherein the inorganic acid is hydrochloric acid, hydrobromic acid, sulfuric acid, nitric acid, amino sulfoacid or phosphoric acid, and the organic acid includes citric acid, tartaric acid, lactic acid, pyruvic acid, acetic acid, benzenesulfonic acid, p-toluenesulfonic acid, methanesulfonic acid, naphthalenesulfonic acid, ethanesulfonic acid, naphthalene disulfonic acid, maleic acid, malic acid, malonic acid, fumaric acid, succinic acid, propionic acid, oxalic acid, trifluoroacetic acid, stearic acid, pamoic acid, hydroxy maleic acid, phenylacetic acid, benzoic acid, salicylic acid, glutamic acid, ascorbic acid, p-amino benzenesulfonic acid, 2-acetoxy-benzoic acid or isethionic acid.

8. The fluoro-substituted cyclic amine compound according to claim 5, or the racemate, R-isomer, S-isomer, pharmaceutically acceptable salt thereof or mixture thereof, wherein $R_1$ is

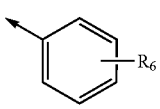

or a $C_3$-$C_7$ cycloalkyl, $R_6$ represents 1-5 substituents, and the substituent is independently selected from the group consisting of a halogen, a nitro, a cyano, a $C_1$-$C_4$ alkyl, a halogen substituted $C_1$-$C_4$ alkyl, a $C_1$-$C_4$ alkoxy, a halogen substituted $C_1$-$C_4$ alkoxy, a phenyl and a $C_1$-$C_4$ alkoxycarbonyl, or two adjacent $R_6$ and carbon atoms of the adjacent benzene ring together form

provided that when $R_1$ is substituted with one $R_6$ and $R_6$ is halogen, then the halogen is F.

9. The fluoro-substituted cyclic amine compound according to claim 5, or the racemate, R-isomer, S-isomer, pharmaceutically acceptable salt thereof or mixture thereof, wherein $R_1$ is

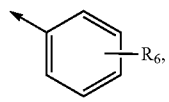

a cyclobutyl, a cyclopentyl, a cyclohexyl or a cycloheptyl, $R_6$ represents 1-5 substituents, and the substituent is independently selected from the group consisting of a nitro, a cyano, —F, a trifluoromethyl, a trifluoroethyl, a trifluoropropyl, a methyl, an ethyl, a propyl, an isopropyl, a butyl, a 2-methylpropyl, a phenyl, a methoxycarbonyl, an ethoxycarbonyl and a propoxycarbonyl, or two adjacent $R_6$ and carbon atoms of the adjacent benzene ring together form

provided that when $R_6$ is F, $R_1$ is substituted with one F.

10. The fluoro-substituted cyclic amine compound according to claim 5, or the racemate, R-isomer, S-isomer, pharmaceutically acceptable salt thereof or mixture thereof, wherein each of $R_2$ and $R_3$ is independently selected from the group consisting of a hydrogen, a carboxyl, a methoxycarbonyl, an ethoxycarbonyl, a propoxycarbonyl, a methyl, an ethyl, a propyl, an isopropyl, a butyl and a 2-methylpropyl; or $R_2$ and $R_3$ together form a methylene, an ethylene or a propylene.

11. The fluoro-substituted cyclic amine compound according to claim 5, or the racemate, R-isomer, S-isomer, pharmaceutically acceptable salt thereof or mixture thereof, wherein $R_4$ represents 1-2 substituents, and the substituent is independently selected from the group consisting of a hydrogen, a halogen, a $C_1$-$C_6$ alkyl, a $C_1$-$C_6$ alkoxy, a halogen substituted $C_1$-$C_6$ alkoxy, a hydroxyl and —O[($CH_2$)$_q$O]$_r$$R_5$, $R_5$; wherein $R_5$ is selected from the group consisting of $C_1$-$C_6$ alkyl and a halogen substituted $C_1$-$C_6$ alkyl; q is 1, 2 or 3; and r is 1, 2 or 3.

12. A fluoro-substituted cyclic amine compound, racemate, a R-isomer, a S-isomer, a pharmaceutically acceptable salt thereof or a mixture thereof selected from the group consisting of:

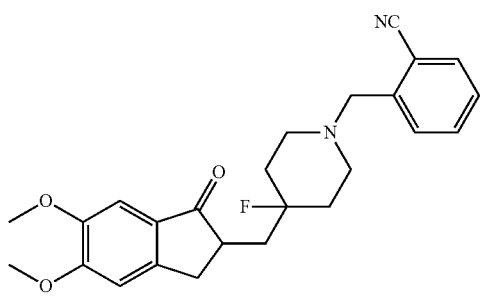

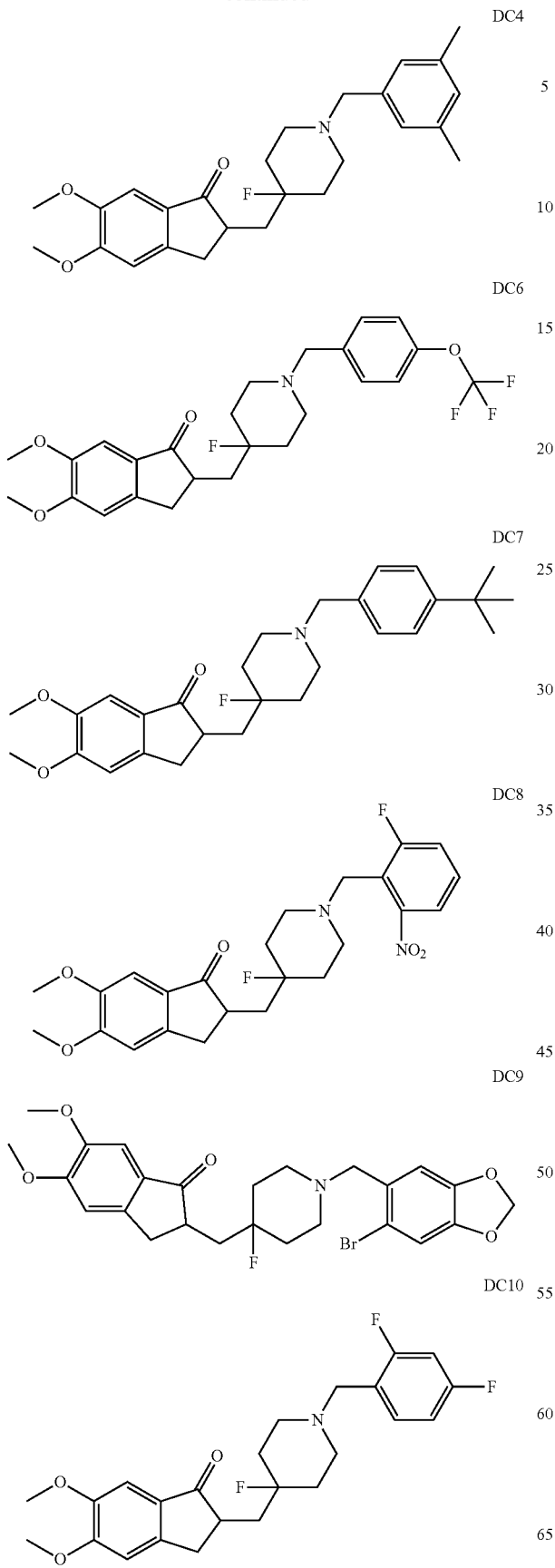
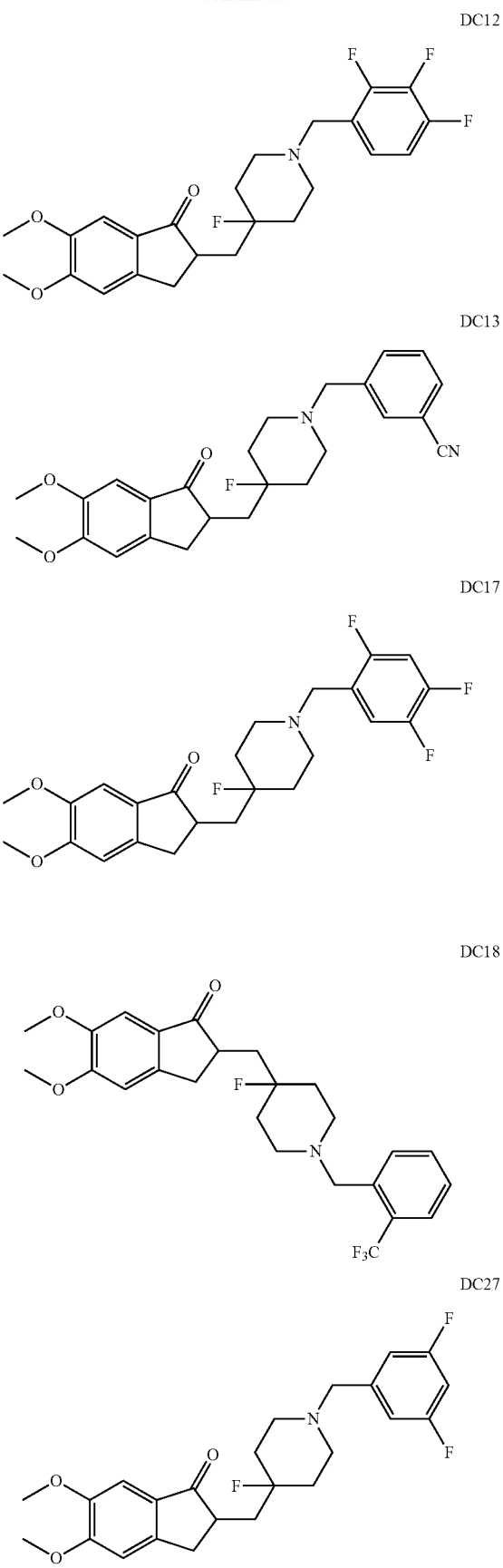

DC28
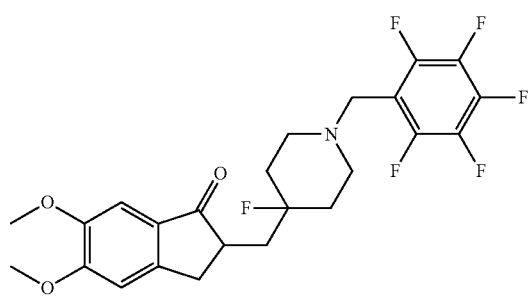
DC34
DC30
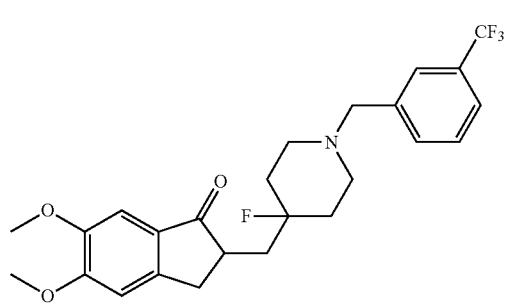
DC35
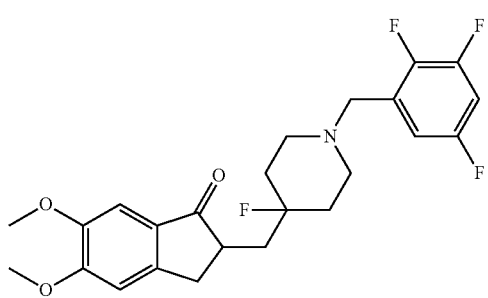
DC31
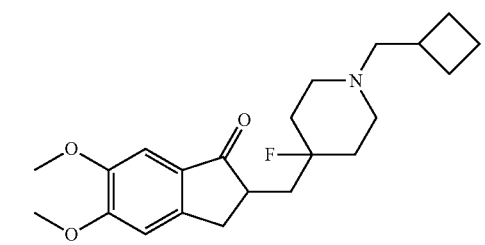
DC22
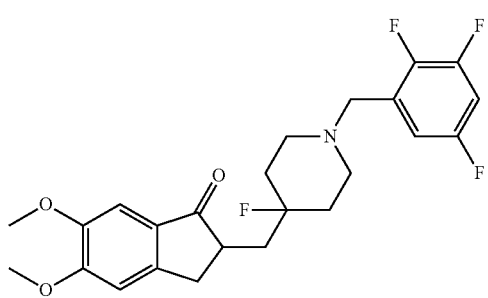
DC32
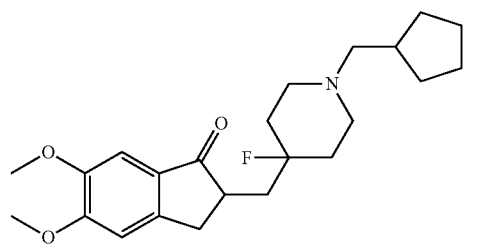
DC36
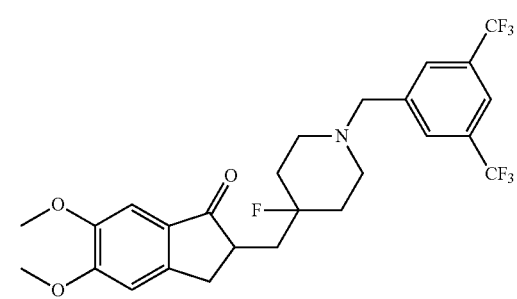
DC33
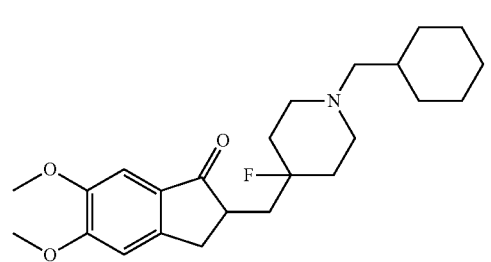
DC37
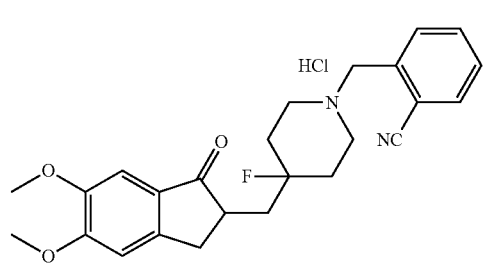

-continued

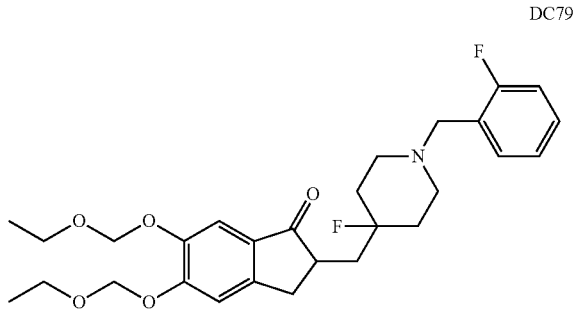
DC79

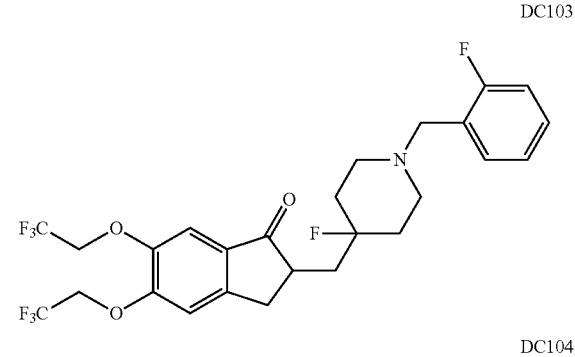
DC103

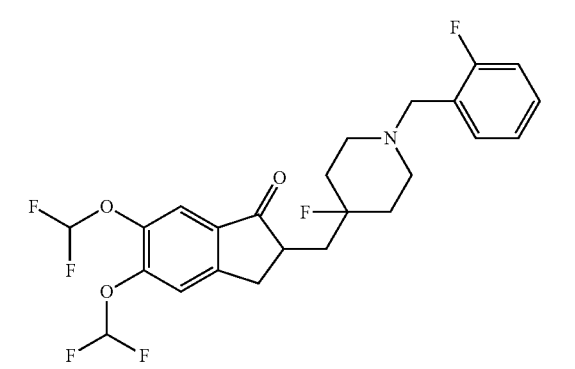
DC104

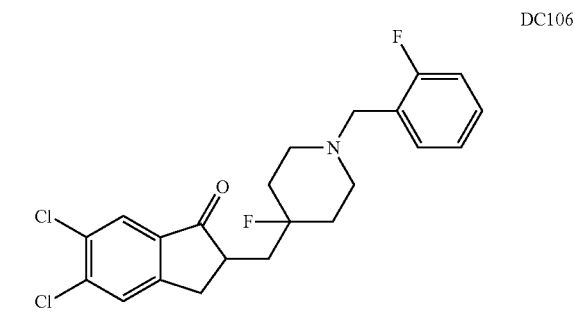
DC106

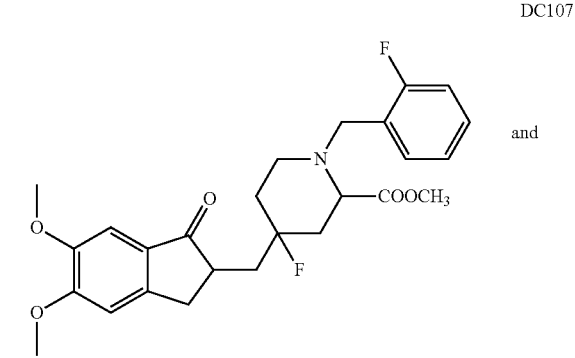
DC107 and

-continued

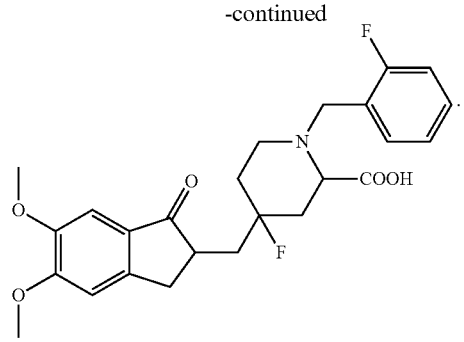

13. A fluoro-substituted cyclic amine compound, racemate, a R-isomer, a S-isomer, a pharmaceutically acceptable salt thereof or a mixture thereof, wherein the compound is

DC20

14. A pharmaceutical composition comprising a therapeutically effective amount of one or more of the fluoro-substituted cyclic amine compounds of claim 1, or the pharmaceutically acceptable salts, racemates, R-isomers or S-isomers thereof, and optionally one or more pharmaceutically acceptable carriers, excipients, adjuvants, auxiliary materials or diluents.

15. An acetylcholinesterase inhibitor comprising a therapeutically effective amount of one or more of the fluoro-substituted cyclic amine compounds of claim 1, or the pharmaceutically acceptable salts, racemates, R-isomers or S-isomers thereof.

16. A pharmaceutical composition comprising a therapeutically effective amount of one or more of the fluoro-substituted cyclic amine compounds of claim 6, or the pharmaceutically acceptable salts, racemates, R-isomers or S-isomers thereof, and optionally one or more pharmaceutically acceptable carriers, excipients, adjuvants, auxiliary materials or diluents.

17. A method of treating an acetyleholinesterase-related nerve system disease selected from the group consisting of Alzheimer's disease, Parkinson's disease, epilepsy, and schizophrenia, comprising administering to the subject the pharmaceutical composition of claim 14.

18. A method of treating an acetylcholinesterase-related nerve system disease selected from the group consisting of Alzheimer's disease, Parkinson's disease, epilepsy, and schizophrenia, comprising administering to the subject the pharmaceutical composition of claim 16.

19. A preparation method for the fluoro-substituted cyclic amine compound according to claim 1, or the racemate, R-isomer, S-isomer, pharmaceutically acceptable salt thereof or mixture thereof, wherein the preparation method is carried out according to the following scheme 1 or scheme 2:

Scheme 1:
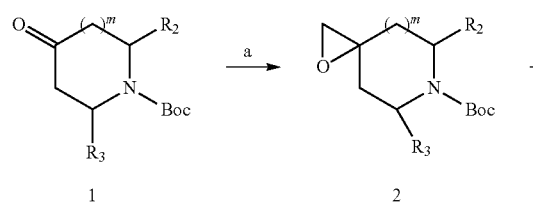
1
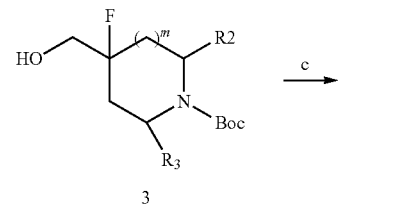
3
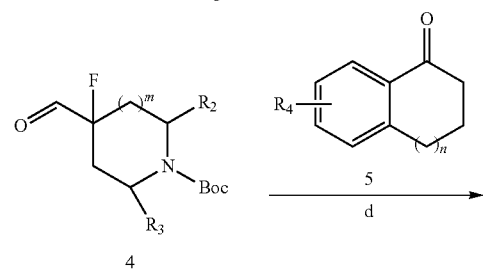
4
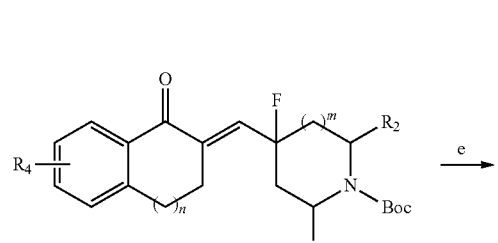
6
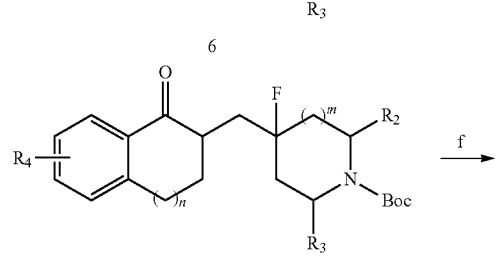
7
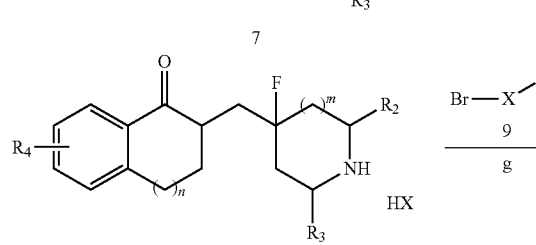
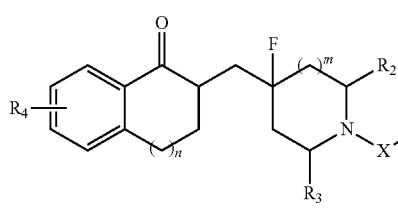
(I)
Scheme 2:
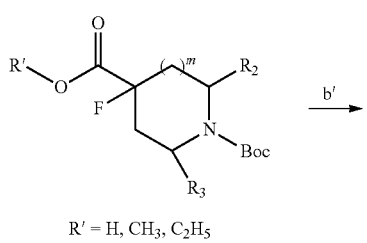
R' = H, CH₃, C₂H₅
1'
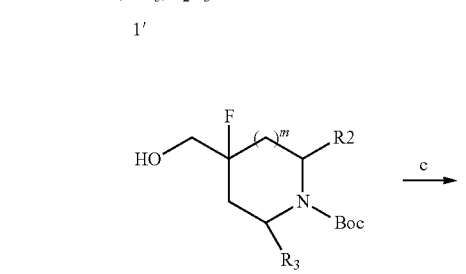
3
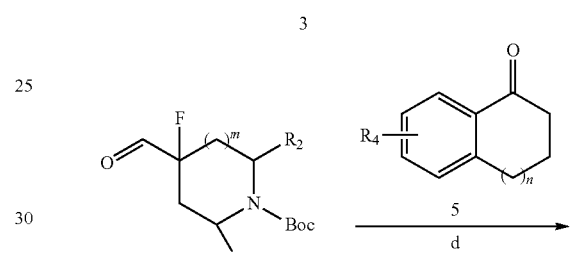
4
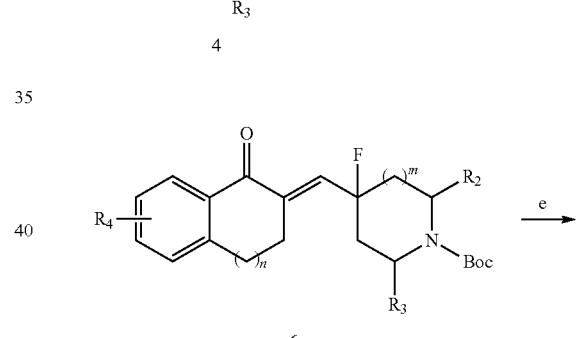
6
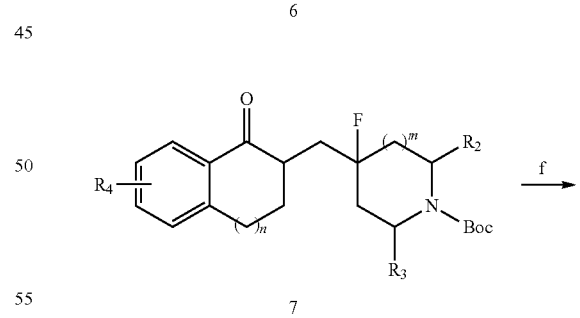
7
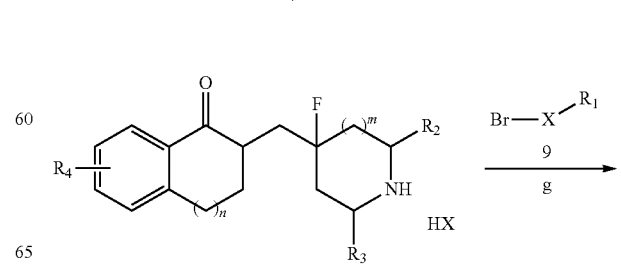
8

-continued

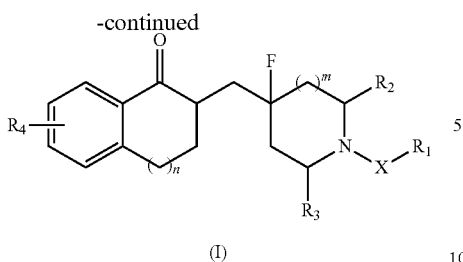

(I)

wherein the definitions of $R_1$, $R_2$, $R_3$, $R_4$, X, m, and n are the same as those defined in general formula I of claim 1; and
wherein:

Step a comprises heating dimethylsulfoxide with stirring and adding NaH to the dimethylsulfoxide to obtain a first reaction solution; cooling the first reaction solution; adding trimethylsulfoxonium iodide and compound 1 to the first reaction solution; and heating the first reaction solution at a temperature of 60° C. to 100° C., thereby obtaining intermediate 2;

Step b comprises dissolving intermediate 2 in a first organic solvent to obtain a second reaction solution and cooling the second reaction solution to a temperature of −10° C. to 40° C.; adding 1-10 equivalents of hydrogen fluoride solution in pyridine to the second reaction solution, thereby obtaining intermediate 3; and isolating intermediate 3 from the second reaction solution, wherein the first organic solvent is tetrahydrofuran, diethyl ether, dimethylformamide, glycol dimethyl ether, glycol diethyl ether, dioxane, ethanol, methanol, ethyl acetate, dichloromethane, or a mixture thereof;

Step c comprises dissolving intermediate 3 in a second organic solvent to obtain a third reaction solution; and adding an oxidant to the third reaction solution, thereby oxidizing intermediate 3 to obtain intermediate 4, wherein the second organic solvent is tetrahydrofuran, diethyl ether, dimethylformamide, glycol dimethyl ether, glycol diethyl ether, dioxane, ethanol, methanol, ethyl acetate, dichloromethane, or a mixture thereof, and the oxidant is selected from the group consisting of pyridinium chlorochromate (PCC), pyridinium dichromate (PDC), Dess-Martin periodinane, Swern oxidant, $H_2O_2$, potassium permanganate, and manganese dioxide;

Step d comprises dissolving intermediate 4 in a third organic solvent to obtain a fourth reaction solution; adding intermediate 5 and a strong base to the fourth reaction solution, thereby obtaining intermediate 6; and isolating intermediate 6 from the fourth reaction solution, wherein the third organic solvent is tetrahydrofuran, diethyl ether, dimethylformamide, glycol dimethyl ether, glycol diethyl ether, dioxane, ethanol, methanol, ethyl acetate, dichloromethane, or a mixture thereof, and the strong base is NaOH, KOH, sodium ethoxide, or sodium methoxide;

Step e comprises dissolving intermediate 6 in a fourth organic solvent to obtain a fifth reaction solution; and adding palladium on carbon and hydrogen gas to the fifth reaction solution, thereby reducing intermediate 6 to obtain intermediate 7, wherein the fourth organic solvent is tetrahydrofuran, diethyl ether, dimethylformamide, glycol dimethyl ether, glycol diethyl ether, dioxane, ethanol, methanol, ethyl acetate, dichloromethane, or a mixture thereof;

Step f comprises dissolving intermediate 7 in a fifth organic solvent to obtain a sixth reaction solution: adding trifluoroacetic acid (TFA) or hydrochloric acid (HCl) to the sixth reaction solution, thereby removing the BOC protecting group of intermediate 7 to obtain intermediate 8, wherein the fifth organic solvent is tetrahydrofuran, diethyl ether, dimethylformamide, glycol dimethyl ether, glycol diethyl ether, dioxane, ethanol, methanol, ethyl acetate, dichloromethane, or a mixture thereof;

Step g comprises dissolving intermediate 8 in a sixth organic solvent to obtain a seventh reaction solution, adding intermediate 9 and a base to the seventh reaction solution; and stirring the seventh reaction solution, thereby obtaining the compound of formula (I), wherein the sixth organic solvent is tetrahydrofuran, diethyl ether, dimethylformamide, glycol dimethyl ether, glycol diethyl ether, dioxane, ethanol, methanol, ethyl acetate, dichloromethane, or a mixture thereof; and the base is sodium acetate, NaOH, KOH, sodium ethoxide, sodium methoxide, sodium carbonate, potassium carbonate, triethylamine, or diisopropylamine; and Step b' comprises reacting compound 1' with a reducing agent, thereby obtaining intermediate 2, wherein the reducing agent is selected from the group consisting of sodium borohydride, potassium borohydride, lithium borohydride, and lithium aluminum hydride ($LiAlH_4$).

* * * * *